(12) United States Patent
Phillips et al.

(10) Patent No.: US 6,489,307 B1
(45) Date of Patent: *Dec. 3, 2002

(54) ANTISENSE COMPOSITIONS TARGETED TO β1-ADRENOCEPTOR-SPECIFIC MRNA AND METHODS OF USE

(75) Inventors: M. Ian Phillips; Yuan Zhang, both of Gainesville, FL (US)

(73) Assignee: University of Florida, Gainesville, FL (US)

( * ) Notice: Subject to any disclaimer, the term of this patent is extended or adjusted under 35 U.S.C. 154(b) by 1 day.

This patent is subject to a terminal disclaimer.

(21) Appl. No.: 09/614,034

(22) Filed: Jul. 11, 2000

Related U.S. Application Data

(63) Continuation-in-part of application No. PCT/US99/21007, filed on Sep. 14, 1999, and a continuation-in-part of application No. 09/152,717, filed on Sep. 14, 1998, now Pat. No. 6,087,343.

(51) Int. Cl.$^7$ .............................................. A01N 43/04
(52) U.S. Cl. ........................... 514/44; 435/6; 435/375; 435/377; 435/320.1; 536/24.1; 536/24.5; 536/23.1
(58) Field of Search ............................... 536/23.1, 24.1, 536/24.5; 514/44; 435/375, 377, 320.1

(56) References Cited

PUBLICATIONS

Frielle et al., PNAS vol. 84: 7920–7924, Nov. 1987.*

* cited by examiner

*Primary Examiner*—Sean McGarry
(74) *Attorney, Agent, or Firm*—Williams, Morgan & Amerson, P.C.

(57) ABSTRACT

Disclosed are antisense oligonucleotide, polynucleotide, and peptide nucleic acid compounds that specifically bind to mammalian mRNA encoding a $\beta_1$-adrenoceptor polypeptide and that are useful in the control and/or treatment of cardiac dysfunction, hypertension, hypertrophy, myocardial ischemia, and other cardiovascular diseases in an affected mammal, and preferably, in a human subject. The antisense compounds disclosed herein, and pharmaceutical formulations thereof, provide sustained control of $\beta_1$-adrenoceptor expression over prolonged periods, and achieve therapeutic effects from as little as a single dose. Administration of these antisense compositions to approved animal models resulted in a decrease in blood pressure, but no significant change in heart rate. Use of such antisense compositions in the reduction of $\beta_1$-adrenoceptor polypeptides in a host cell expressing $\beta_1$-adrenoceptor-specific mRNA, and in the preparation of medicaments for treating human and animal diseases, and in particular, hypertension and other cardiac dysfunction is also disclosed.

65 Claims, 13 Drawing Sheets

SEQUENCE LISTING

<160> NUMBER OF SEQ ID NOS: 204

<210> SEQ ID NO 1
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 1
ccgcgcccat gccga                                                                 15

<210> SEQ ID NO 2
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 2
ggccgacgac aggtt                                                                 15

<210> SEQ ID NO 3
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 3
atgagcagca cgatg                                                                 15

<210> SEQ ID NO 4
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 4
gggcgctcgc cctggcgcct ccgaaccctg caacc                                           35

<210> SEQ ID NO 5
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 5
atgggcgcgg gggcgctcgc cctggcgcct ccgaa                                           35

<210> SEQ ID NO 6
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 6
gcctccgaat cggcatgggc gcggggcgc tcgcc                                            35

<210> SEQ ID NO 7
<211> LENGTH: 35

```
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 7 acccccgcg cccggcctcc gaatcggcat gggcg                          35

<210> SEQ ID NO 8
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 8
gggtgctcgt cctgggcgcc tccgagcccg gtaac                         35

<210> SEQ ID NO 9
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 9
atgggcgcgg gggtgctcgt cctgggcgcc tccga                         35

<210> SEQ ID NO 10
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 10
gcagctcggc atgggcgcgg gggtgctcgt cctgg                         35

<210> SEQ ID NO 11
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 11
cccggcctcc gcagctcggc atgggcgcgg gggtg                         35

<210> SEQ ID NO 12
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 12 ccgccccgg cctccgcagc tcggcatggg cgcgg                          35

<210> SEQ ID NO 13
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 13
``` acccccgcc cccggcctcc gcagctcggc atggg            35

<210> SEQ ID NO 14
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 14
gggcgctcgc cctgggcgcc tccgaaccct gcaac            35

<210> SEQ ID NO 15
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 15
atgggcgcgg gggcgctcgc cctgggcgcc tccga            35

<210> SEQ ID NO 16
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 16
gcagctcggc atgggcgcgg gggcgctcgc cctgg            35

<210> SEQ ID NO 17
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 17
cccggcctcc gcagctcggc atgggcgcgg gggcg            35

<210> SEQ ID NO 18
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 18
gggcgctcgc cctgggcgcc tccgagccct gcaac            35

<210> SEQ ID NO 19
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 19
atgggcgcgg gggcgctcgc cctgggcgcc tccga            35

<210> SEQ ID NO 20
<211> LENGTH: 35
<212> TYPE: DNA
<213> ORGANISM: UNKNOWN

```
<220> FEATURE:
<223> OTHER INFORMATION: SYNTHETIC OLIGONUCLEOTIDE

<400> SEQUENCE: 20
gcagctcggc atgggcgcgg gggcgctcgc cctgg                           35

<210> SEQ ID NO 21
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 21
cccggcctcc gcagctcggc atgggcgcgg gggcg                           35

<210> SEQ ID NO 22
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 22 gcggggcgt cgccctgggt gcctccgagc cctgc                            35

<210> SEQ ID NO 23
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 23
atggggcggg ggcgtcgccc tgggtgcctc cgagc                           35

<210> SEQ ID NO 24
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 24
cgcagccggt atggggcggg ggcgtcgccc tgggt                           35

<210> SEQ ID NO 25
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 25
cccccgcctc cgcagccggt atggggcggg ggcgt                           35

<210> SEQ ID NO 26
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 26
gggcgctcgt cctgggcgcc tccgagcccg gtaac                           35
```

<210> SEQ ID NO 27
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 27
atgggcgcgg gggcgctcgt cctgggcgcc tccga       35

<210> SEQ ID NO 28
<211> LENGTH: 35
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 28
gcaactcggc atgggcgcgg gggcgctcgt cctgg       35

<210> SEQ ID NO 29
<211> LENGTH: 34
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 29
cagctcggca tgggcgcggg ggtgctcgtc ctgg        34

<210> SEQ ID NO 30
<211> LENGTH: 34
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 30
gcagctcggc atgggcgcgg gggtgctcgt cctg        34

<210> SEQ ID NO 31
<211> LENGTH: 33
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 31
agctcggcat gggcgcgggg gtgctcgtcc tgg         33

<210> SEQ ID NO 32
<211> LENGTH: 33
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 32
gcagctcggc atgggcgcgg gggtgctcgt cct         33

<210> SEQ ID NO 33
<211> LENGTH: 32
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 33
gctcggcatg ggcgcggggg tgctcgtcct gg          32

<210> SEQ ID NO 34
<211> LENGTH: 32
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 34
gcagctcggc atgggcgcgg gggtgctcgt cc          32

<210> SEQ ID NO 35
<211> LENGTH: 31
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 35
ctcggcatgg gcgcgggggt gctcgtcctg g           31

<210> SEQ ID NO 36
<211> LENGTH: 31
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 36
gcagctcggc atgggcgcgg gggtgctcgt c           31

<210> SEQ ID NO 37
<211> LENGTH: 30
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 37
tcggcatggg cgcggggtg ctcgtcctgg             30

<210> SEQ ID NO 38
<211> LENGTH: 30
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 38
gcagctcggc atgggcgcgg gggtgctcgt             30

<210> SEQ ID NO 39
<211> LENGTH: 29
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 39
cggcatgggc gcggggtgc tcgtcctgg              29

<210> SEQ ID NO 40

```
<211> LENGTH: 29
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 40
gcagctcggc atgggcgcgg gggtgctcg                              29

<210> SEQ ID NO 41
<211> LENGTH: 28
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 41
ggcatgggcg cggggtgct cgtcctgg                                28

<210> SEQ ID NO 42
<211> LENGTH: 28
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 42
gcagctcggc atgggcgcgg gggtgctc                               28

<210> SEQ ID NO 43
<211> LENGTH: 27
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 43
gcatgggcgc ggggtgctc gtcctgg                                 27

<210> SEQ ID NO 44
<211> LENGTH: 27
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 44
gcagctcggc atgggcgcgg gggtgct                                27

<210> SEQ ID NO 45
<211> LENGTH: 26
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 45
catgggcgcg ggggtgctcg tcctgg                                 26

<210> SEQ ID NO 46
<211> LENGTH: 26
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 46
```
gcagctcggc atgggcgcgg gggtgc    26

<210> SEQ ID NO 47
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 47
atgggcgcgg gggtgctcgt cctgg    25

<210> SEQ ID NO 48
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 48
gcagctcggc atgggcgcgg gggtg    25

<210> SEQ ID NO 49
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 49
tgggcgcggg ggtgctcgtc ctgg    24

<210> SEQ ID NO 50
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 50
gcagctcggc atgggcgcgg gggt    24

<210> SEQ ID NO 51
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 51
gggcgcgggg gtgctcgtcc tgg    23

<210> SEQ ID NO 52
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 52
gcagctcggc atgggcgcgg ggg    23

<210> SEQ ID NO 53
<211> LENGTH: 22
<212> TYPE: DNA

<213> ORGANISM: UNKNOWN
<220> FEATURE:
<223> OTHER INFORMATION: SYNTHETIC OLIGONUCLEOTIDE

<400> SEQUENCE: 53
ggcgcggggg tgctcgtcct gg        22

<210> SEQ ID NO 54
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 54
gcagctcggc atgggcgcgg gg        22

<210> SEQ ID NO 55
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 55 gcgcggggt gctcgtcctg g        21

<210> SEQ ID NO 56
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 56
gcagctcggc atgggcgcgg g        21

<210> SEQ ID NO 57
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 57 cgcggggtg ctcgtcctgg        20

<210> SEQ ID NO 58
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 58
gcagctcggc atgggcgcgg        20

<210> SEQ ID NO 59
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 59 gcggggtgc tcgtcctgg        19

```
<210> SEQ ID NO 60
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 60
gcagctcggc atgggcgcg                                                        19

<210> SEQ ID NO 61
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 61 cggggtgct cgtcctgg                                                          18

<210> SEQ ID NO 62
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 62
gcagctcggc atgggcgc                                                         18

<210> SEQ ID NO 63
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 63
gggggtgctc gtcctgg                                                          17

<210> SEQ ID NO 64
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 64
gcagctcggc atgggcg                                                          17

<210> SEQ ID NO 65
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 65
ggggtgctcg tcctgg                                                           16

<210> SEQ ID NO 66
<211> LENGTH: 16
<212> TYPE: DNA
<213> ORGANISM: UNKNOWN
<220> FEATURE:
```

```
<223> OTHER INFORMATION: SYNTHETIC OLIGONUCLEOTIDE

<400> SEQUENCE: 66
gcagctcggc atgggc                                                    16

<210> SEQ ID NO 67
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 67
gggtgctcgt cctgg                                                     15

<210> SEQ ID NO 68
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 68
gcagctcggc atggg                                                     15

<210> SEQ ID NO 69
<211> LENGTH: 14
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 69
ggtgctcgtc ctgg                                                      14

<210> SEQ ID NO 70
<211> LENGTH: 14
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 70
gcagctcggc atgg                                                      14

<210> SEQ ID NO 71
<211> LENGTH: 14
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 71
ggtgctcgtc ctgg                                                      14

<210> SEQ ID NO 72
<211> LENGTH: 13
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 72
gcagctcggc atg                                                       13
```

<210> SEQ ID NO 73
<211> LENGTH: 13
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 73
gtgctcgtcc tgg                                              13

<210> SEQ ID NO 74
<211> LENGTH: 12
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 74
gcagctcggc at                                               12

<210> SEQ ID NO 75
<211> LENGTH: 12
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 75
tgctcgtcct gg                                               12

<210> SEQ ID NO 76
<211> LENGTH: 11
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 76
gcagctcggc a                                                11

<210> SEQ ID NO 77
<211> LENGTH: 11
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 77
gctcgtcctg g                                                11

<210> SEQ ID NO 78
<211> LENGTH: 10
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 78
gcagctcggc                                                  10

<210> SEQ ID NO 79
<211> LENGTH: 10
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 79
ctcgtcctgg                                                                    10

<210> SEQ ID NO 80
<211> LENGTH: 9
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 80 gcagctcgg                                                                      9

<210> SEQ ID NO 81
<211> LENGTH: 14
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 81
cgcgcccatg ccga                                                               14

<210> SEQ ID NO 82
<211> LENGTH: 14
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 82
ccgcgcccat gccg                                                               14

<210> SEQ ID NO 83
<211> LENGTH: 13
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 83
gcgcccatgc cga                                                                13

<210> SEQ ID NO 84
<211> LENGTH: 13
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 84
ccgcgcccat gcc                                                                13

<210> SEQ ID NO 85
<211> LENGTH: 12
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 85
cgcccatgcc ga                                                                 12

<210> SEQ ID NO 86
<211> LENGTH: 12

```
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 86
ccgcgcccat gc                                                            12

<210> SEQ ID NO 87
<211> LENGTH: 11
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 87
gcccatgccg a                                                             11

<210> SEQ ID NO 88
<211> LENGTH: 11
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 88
ccgcgcccat g                                                             11

<210> SEQ ID NO 89
<211> LENGTH: 10
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 89
cccatgccga                                                               10

<210> SEQ ID NO 90
<211> LENGTH: 10
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 90
ccgcgcccat                                                               10

<210> SEQ ID NO 91
<211> LENGTH: 9
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 91 ccatgccga                                                                 9

<210> SEQ ID NO 92
<211> LENGTH: 9
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 92
```

```
                                -continued ccgcgccca                                                           9

<210> SEQ ID NO 93
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 93 caccccgcg cccat                                                    15

<210> SEQ ID NO 94
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 94 accccgcgc ccatg                                                    15

<210> SEQ ID NO 95
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 95
cgcgcccatg ccgag                                                   15

<210> SEQ ID NO 96
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 96
gcgcccatgc cgagc                                                   15

<210> SEQ ID NO 97
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 97
cgcccatgcc gagct                                                   15

<210> SEQ ID NO 98
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 98
gcccatgccg agctg                                                   15

<210> SEQ ID NO 99
<211> LENGTH: 15
<212> TYPE: DNA
<213> ORGANISM: UNKNOWN
```

<220> FEATURE:
<223> OTHER INFORMATION: SYNTHETIC OLIGONUCLEOTIDE

<400> SEQUENCE: 99
cccatgccga gctgc                                                    15

<210> SEQ ID NO 100
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 100
ccatgccgag ctgcg                                                    15

<210> SEQ ID NO 101
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 101
catgccgagc tgcgg                                                    15

<210> SEQ ID NO 102
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 102
atgccgagct gcgga                                                    15

<210> SEQ ID NO 103
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 103
gcgcccatgc cgagct                                                   16

<210> SEQ ID NO 104
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 104
cgcccatgcc gagctg                                                   16

<210> SEQ ID NO 105
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 105
gcccatgccg agctgc                                                   16

```
<210> SEQ ID NO 106
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 106
cccatgccga gctgcg                                                    16

<210> SEQ ID NO 107
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 107
ccatgccgag ctgcgg                                                    16

<210> SEQ ID NO 108
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 108
catgccgagc tgcgga                                                    16

<210> SEQ ID NO 109
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 109
atgccgagct gcggag                                                    16

<210> SEQ ID NO 110
<211> LENGTH: 16
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 110
tgccgagctg cggagg                                                    16

<210> SEQ ID NO 111
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 111
cgcgcccatg ccgagct                                                   17

<210> SEQ ID NO 112
<211> LENGTH: 17
<212> TYPE: DNA
<213> ORGANISM: UNKNOWN
<220> FEATURE:
<223> OTHER INFORMATION: SYNTHETIC OLIGONUCLEOTIDE
```

<400> SEQUENCE: 112
gcgcccatgc cgagctg                                                17

<210> SEQ ID NO 113
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 113
cgcccatgcc gagctgc                                                17

<210> SEQ ID NO 114
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 114
gcccatgccg agctgcg                                                17

<210> SEQ ID NO 115
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 115
cccatgccga gctgcgg                                                17

<210> SEQ ID NO 116
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 116
ccatgccgag ctgcgga                                                17

<210> SEQ ID NO 117
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 117
catgccgagc tgcggag                                                17

<210> SEQ ID NO 118
<211> LENGTH: 17
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 118
atgccgagct gcggagg                                                17

<210> SEQ ID NO 119

<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 119
ccgcgcccat gccgagct                                                18

<210> SEQ ID NO 120
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 120
cgcgcccatg ccgagctg                                                18

<210> SEQ ID NO 121
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 121
gcgcccatgc cgagctgc                                                18

<210> SEQ ID NO 122
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 122
cgcccatgcc gagctgcg                                                18

<210> SEQ ID NO 123
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 123
gcccatgccg agctgcgg                                                18

<210> SEQ ID NO 124
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 124
cccatgccga gctgcgga                                                18

<210> SEQ ID NO 125
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 125

```
ccatgccgag ctgcggag                                           18

<210> SEQ ID NO 126
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 126
catgccgagc tgcggagg                                           18

<210> SEQ ID NO 127
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 127
acccccgcgc ccatgccga                                          19

<210> SEQ ID NO 128
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 128
cccgcgccca tgccgagct                                          19

<210> SEQ ID NO 129
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 129
ccgcgcccat gccgagctg                                          19

<210> SEQ ID NO 130
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 130
cgcgcccatg ccgagctgc                                          19

<210> SEQ ID NO 131
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 131
gcgcccatgc cgagctgcg                                          19

<210> SEQ ID NO 132
<211> LENGTH: 19
<212> TYPE: DNA
```

```
<213> ORGANISM: UNKNOWN
<220> FEATURE:
<223> OTHER INFORMATION: SYNTHETIC OLIGONUCLEOTIDE

<400> SEQUENCE: 132
cgcccatgcc gagctgcgg                                          19

<210> SEQ ID NO 133
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 133
gcccatgccg agctgcgga                                          19

<210> SEQ ID NO 134
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 134
cccatgccga gctgcggag                                          19

<210> SEQ ID NO 135
<211> LENGTH: 19
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 135
ccatgccgag ctgcggagg                                          19

<210> SEQ ID NO 136
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 136 caccccgcg cccatgccga                                          20

<210> SEQ ID NO 137
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 137 accccgcgc ccatgccgag                                          20

<210> SEQ ID NO 138
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 138 ccccgcgcc catgccgagc                                          20
```

<210> SEQ ID NO 139
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 139
ccccgcgccc atgccgagct                                              20

<210> SEQ ID NO 140
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 140
cccgcgccca tgccgagctg                                              20

<210> SEQ ID NO 141
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 141
ccgcgcccat gccgagctgc                                              20

<210> SEQ ID NO 142
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 142
cgcgcccatg ccgagctgcg                                              20

<210> SEQ ID NO 143
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 143
gcgcccatgc cgagctgcgg                                              20

<210> SEQ ID NO 144
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 144
cgcccatgcc gagctgcgga                                              20

<210> SEQ ID NO 145
<211> LENGTH: 20
<212> TYPE: DNA
<213> ORGANISM: UNKNOWN
<220> FEATURE:

<223> OTHER INFORMATION: SYNTHETIC OLIGONUCLEOTIDE

<400> SEQUENCE: 145
gcccatgccg agctgcggag                 20

<210> SEQ ID NO 146
<211> LENGTH: 20
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 146
cccatgccga gctgcggagg                 20

<210> SEQ ID NO 147
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 147
cacccccgcg cccatgccga g               21

<210> SEQ ID NO 148
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 148
acccccgcgc ccatgccgag c               21

<210> SEQ ID NO 149
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 149
cccccgcgcc catgccgagc t               21

<210> SEQ ID NO 150
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 150
ccccgcgccc atgccgagct g               21

<210> SEQ ID NO 151
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 151
cccgcgccca tgccgagctg c               21

<210> SEQ ID NO 152
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 152
ccgcgcccat gccgagctgc g                                      21

<210> SEQ ID NO 153
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 153
cgcgcccatg ccgagctgcg g                                      21

<210> SEQ ID NO 154
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 154
gcgcccatgc cgagctgcgg a                                      21

<210> SEQ ID NO 155
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 155
cgcccatgcc gagctgcgga g                                      21

<210> SEQ ID NO 156
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 156
gcccatgccg agctgcggag g                                      21

<210> SEQ ID NO 157
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 157 caccccgcg cccatgccga gc                                      22

<210> SEQ ID NO 158
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

-continued

<210> SEQ ID NO 159
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 159
cccccgcgcc catgccgagc tg                                              22

<210> SEQ ID NO 160
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 160
ccccgcgccc atgccgagct gc                                              22

<210> SEQ ID NO 161
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 161
cccgcgccca tgccgagctg cg                                              22

<210> SEQ ID NO 162
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 162
ccgcgcccat gccgagctgc gg                                              22

<210> SEQ ID NO 163
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 163
cgcgcccatg ccgagctgcg ga                                              22

<210> SEQ ID NO 164
<211> LENGTH: 22
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 164
gcgcccatgc cgagctgcgg ag                                              22

<210> SEQ ID NO 165
<211> LENGTH: 22

<400> SEQUENCE: 158 accccgcgc ccatgccgag ct                                               22

```
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 165
cgcccatgcc gagctgcgga gg                                             22

<210> SEQ ID NO 166
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 166 caccccgcg cccatgccga gct                                             23

<210> SEQ ID NO 167
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 167 accccgcgc ccatgccgag ctg                                             23

<210> SEQ ID NO 168
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 168 ccccgcgcc catgccgagc tgc                                             23

<210> SEQ ID NO 169
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 169 cccgcgccc atgccgagct gcg                                             23

<210> SEQ ID NO 170
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 170
cccgcgccca tgccgagctg cgg                                            23

<210> SEQ ID NO 171
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 171
```

```
ccgcgcccat gccgagctgc gga                                          23

<210> SEQ ID NO 172
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 172
cgcgcccatg ccgagctgcg gag                                          23

<210> SEQ ID NO 173
<211> LENGTH: 23
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 173
gcgcccatgc cgagctgcgg agg                                          23

<210> SEQ ID NO 174
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 174 caccccgcg cccatgccga gctg                                          24

<210> SEQ ID NO 175
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 175 accccgcgc ccatgccgag ctgc                                          24

<210> SEQ ID NO 176
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 176 ccccgcgcc catgccgagc tgcg                                          24

<210> SEQ ID NO 177
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 177
ccccgcgccc atgccgagct gcgg                                         24

<210> SEQ ID NO 178
<211> LENGTH: 24
<212> TYPE: DNA
<213> ORGANISM: UNKNOWN
```

```
<220> FEATURE:
<223> OTHER INFORMATION: SYNTHETIC OLIGONUCLEOTIDE

<400> SEQUENCE: 178
cccgcgccca tgccgagctg cgga                                          24

<210> SEQ ID NO 179
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 179
ccgcgcccat gccgagctgc ggag                                          24

<210> SEQ ID NO 180
<211> LENGTH: 24
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 180
cgcgcccatg ccgagctgcg gagg                                          24

<210> SEQ ID NO 181
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 181 caccccgcg cccatgccga gctgc                                          25

<210> SEQ ID NO 182
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 182 accccgcgc ccatgccgag ctgcg                                          25

<210> SEQ ID NO 183
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 183 ccccgcgcc catgccgagc tgcgg                                          25

<210> SEQ ID NO 184
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 184
ccccgcgccc atgccgagct gcgga                                         25
```

<210> SEQ ID NO 185
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 185
cccgcgccca tgccgagctg cggag                                          25

<210> SEQ ID NO 186
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 186
ccgcgcccat gccgagctgc ggagg                                          25

<210> SEQ ID NO 187
<211> LENGTH: 1723
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 187
tgctacccgc gcccgggctt ctggggtgtt ccccaaccac ggcccagccc tgccacaccc     60 cccgccccg gcctccgcag ctcggcatgg gcgcgggggt gctcgtcctg ggcgcctccg     120
agcccggtaa cctgtcgtcg gccgcaccgc tccccgacgg cgcggccacc gcggcgcggc     180
tgctggtgcc cgcgtcgccg cccgcctcgt tgctgcctcc cgccagcgaa agccccgagc     240
cgctgtctca gcagtggaca gcgggcatgg gtctgctgat ggcgctcatc gtgctgctca     300
tcgtggcggg caatgtgctg gtgatcgtgg ccatcgccaa gacgccgcgg ctgcagacgc     360
tcaccaacct cttcatcatg tccctggcca gcgccgacct ggtcatgggg ctgctggtgg     420
tgccgttcgg ggccaccatc gtggtgtggg gccgctggga gtacggctcc ttcttctgcg     480
agctgtggac ctcagtggac gtgctgtgcg tgacggccag catcgagacc ctgtgtgtca     540
ttgccctgga ccgctacctc gccatcacct cgcccttccg ctaccagagc ctgctgacgc     600
gcgcgcgggc gcggggcctc gtgtgcaccg tgtgggccat ctcggccctg gtgtccttcc     660
tgcccatcct catgcactgg tggcgggcgg agagcgacga ggcgcgccgc tgctacaacg     720
accccaagtg ctgcgacttc gtcaccaacc gggcctacgc catcgcctcg tccgtagtct     780
ccttctacgt gcccctgtgc atcatggcct tcgtgtacct gcgggtgttc cgcgaggccc     840
agaagcaggt gaagaagatc gacagctgcg agcgccgttt cctcggcggc cagcgcggc     900 cgccctcgcc ctcgccctcg cccgtccccg cgccgcgcc gcgcccgga ccccgcgcc     960 ccgccgccgc cgccgccacc gccccgctgg ccaacgggcg tgcgggtaag cggcggccct    1020
cgcgcctcgt ggccctacgc gagcagaagg cgctcaagac gctgggcatc atcatgggcg    1080
tcttcacgct ctgctggctg cccttcttcc tggccaacgt ggtgaaggcc ttccaccgcg    1140
agctggtgcc cgaccgcctc ttcgtcttct caactggct gggctacgcc aactcggcct    1200
tcaaccccat catctactgc cgcagccccg acttccgcaa ggccttccag ggactgctct    1260
gctgcgcgcg cagggctgcc cgccggcgcc acgcgaccca cggagaccgg ccgcgcgcct    1320
cgggctgtct ggcccggccc ggaccccgc catcgcccgg ggccgcctcg gacgacgacg    1380

```
acgacgatgt cgtcgggcc acgccgcccg cgcgcctgct ggagccctgg gccggctgca    1440 acggcgggc ggcggcggac agcgactcga gcctggacga gccgtgccgc cccggcttcg    1500
cctcggaatc caaggtgtag ggcccggcgc ggggcgcgga ctccgggcac ggcttcccag    1560
gggaacgagg agatctgtgt ttacttaaga ccgatagcag gtgaactcga agcccacaat    1620
cctcgtctga atcatccgag gcaaagagaa aagccacgga ccgttgcaca aaaaggaaag    1680
tttgggaagg gatgggagag tggcttgctg atgttccttg ttg                     1723
```

<210> SEQ ID NO 188
<211> LENGTH: 1845
<212> TYPE: DNA
<213> ORGANISM: UNKNOWN
<220> FEATURE:
<223> OTHER INFORMATION: SYNTHETIC OLIGONUCLEOTIDE
<221> NAME/KEY: misc_feature
<222> LOCATION: (1828)..(1828)
<223> OTHER INFORMATION: WHERE N = A, T, C OR G

<400> SEQUENCE: 188

```
ccgggtgccg ggcccgcggg ctcggcgcgc tcagaaacat gctgaggtcc cggcggctgt      60
tgcagcagcg gcagcggctc cagcagcggc tccagcagcg gctccggcag cggctccagc     120
ggcggcaact ccggcggcag cagcagcggc ggcggcggcg gcgcagcgc acggctcccg      180 cggggaaggc gccggcgcc catgcctccg gcccgcgcg gcggctgccc tgacccggcc       240
gcgacctccg cgccccacgt cccccggcgt ggtccccggc cacggcccca gcccgccaca     300
ccccccgccc ccggcctccg cagctcggca tgggcgcggg ggcgctggcc ctgggcgcct     360
cggagccctg caacctgtcg tcggccgcgc cgctccccga cggcgcggcc acggcggcga     420
ggctgctggt gccgcgtcg ccgtccgcct cgccgctggc cccgaccagc gagggccccg     480
cgccgctgtc gcagcagtgg acggcgggca tcgggctgct gatggcgctc atcgtgctgc     540
tcatcgtggc gggcaacgtg ctggtgatcg cggccatcgc caagacgccg cggctgcaga     600
cgctcaccaa cctgttcatc atgtccctgg ccagcgccga cctggtcatg gggctgctgg     660
tggtgccctt cggggccacg atcgtcatgc ggggccgctg ggagtacggc tccttcctgt     720
gcgagctctg gacctcggtg gacgtgctgt gcgtgacggc cagcatcgag accctgtgtg     780
tcatcgcgct ggaccgctac ctggccatca ccgcgccctt ccgctaccag agcctgctga     840
cgcgcgcgcg cgcgcgggcc ctcgtgtgca ccgtgtgggc catctcggcg ctcgtgtcct     900
tcctgcccat cctcatgcac tggtggcggg ccggggcgcga cgaggcgcgc cgctgctaca     960
acgaccccaa gtgctgcgac ttcgtcacca accgggccta cgccatcgcc tcgtccgtcg    1020
tctccttcta cgtgccctg tgcatcatgg ccttcgtgta cctgcgggtg ttccgcgagg    1080
cgcagaagca ggtgaagaag atcgacagct gcgagcgccg cttcctgggc ggccccgcgc    1140
ggccccccgc gccccgccc gcgcccgcgc ccgcgccccc gccgcgccc ggctccccgc     1200 gccccgcgc ggccgcccg ctggccaacg ggcgcgtcgg caggcggcgg ccctcgcgcc     1260
tcgtggcgct gcgcgagcag aaggcgctca agacgctggg catcatcatg ggcgtgttca    1320
cgctgtgctg gctgcccttc ttcctggcca acgtggtcaa ggcttccac cgcgacctgg     1380 tgcccgaccg cctcttcgtc ttcttcaact ggctgggcta cgccaactcg gccttcaacc    1440
ccatcatcta ctgccgcagc cccgacttcc gcagggcctt ccagcgcctg ctgtgctgcg    1500
cgcgccgcgc gcccgcggg agccacgggg ccgccgggga ccctcgcgg gcccggccg     1560 cgccgtcccc cggggccgcc tcggacgacg acgacgacga cgaggacgac gccggggccg    1620
```

```
gggccggggc cgcgccgccc gcgcgcctgc tggagccctg ggccggctgc aacggcgggg      1680
cggcggccga cagcgactcc agcctggacg gcgcgggcag ccccgcgggc gcctcggagt      1740
cccgggtgta ggcgcgcggc ctcccggggg gcgcatcggt gtttactcca gacccagagc      1800
aggtgaaccc cgggcccgcg cacccccntc gcattcatcg aggca                     1845
```

<210> SEQ ID NO 189
<211> LENGTH: 4749
<212> TYPE: DNA
<213> ORGANISM: UNKNOWN
<220> FEATURE:
<223> OTHER INFORMATION: SYNTHETIC OLIGONUCLEOTIDE
<221> NAME/KEY: misc_feature
<222> LOCATION: (1223)..(1223)
<223> OTHER INFORMATION: WHERE Y = T OR C
<221> NAME/KEY: misc_feature
<222> LOCATION: (1959)..(2394)
<223> OTHER INFORMATION: WHERE N = A, T, C OR G
<221> NAME/KEY: misc_feature
<222> LOCATION: (3775)..(3775)
<223> OTHER INFORMATION: WHERE M = A OR C

<400> SEQUENCE: 189

```
tccagccccc tctttctagc cctctccttc cctcatttcc ccttctcagg ctccccaact       60
ggcagaacta agctgacaat cctaagccag ggatgcagaa acaagtaatt cacccacatc      120
cacccactga tcatcaagtt tgggcctaaa gcaaatttac atgtttggat aagaaaagt      180 tgggcttccc tagtagctga gacccatctt cagtccttgg atgggggaag atcccctaga      240
gaaggagatg gcaacccact ctagtattct tgcctggaaa atcccatagg cagaggagcc      300
tggtggctac agcccatggg gttgcaagag tcagacacaa cttagctact aaaaccacca      360
cccatggctt atgaatacac attgctgtta gctctcgact tagggagctc tctccaaggt      420
aagaatatga gtttgttcct ttcagaaact attcttttta ttccaatgct agaaggatgt      480
gtgagcatta tgtaacattt tcatgcaccc ttaagtgggt aattagaagc tctttatttc      540
tcaggattca attaaaagct ttttattttc aaggctgagt tgaggaccag tactgtggtg      600
gaattagaca aggggcttgc acacctttgg ctacattgtg tgttgatggg ccaccttcct      660
gtaggtacct cccacacatat agtcacacca ctgcagagct aacgactcac taatttaaa      720 cccattcagt tgccaaccca acagcctttg atataacttt acatgctatt ggattttaat      780 cttttttgagt atttatatat gttttcttct ctcatccctc caaaattaat cctagagttt      840
tgagaatctg ggaacttggg caaaggagaa ggcaacgcag cagaccaaga aatttgaaat      900
ctcagttcac tactgtgtca cccaaagtca atgtaccttt tttgtttgga ccggcccagc      960
tcaagtcata caatcacgtg agtaacagac cacaaaatcc aggtgttatt actgaacatg     1020
acaagtctga aaagtaatta cacgtgttct agcttccgtg gcggtgtcat ttactctaac     1080
atgcctgtcc ttaagcctct ctctctcttt acattaccgg cacacaccgg tgcaccatac     1140
tcacacatcc atcagctggg acctgggagt gtgtattatt ccaactggtc ctcagcatta     1200
gctgtcagat gtcacaaccc ccygccgttt tctgcatctg ctccccgggg aagcgagaag     1260
aagcttgcaa gaatagctcc cgggaacgtt cctgaaagat tggcgctctg ctttagcaag     1320
gcgctcgctg gaaagtttct tctaaccgct cacacccgcc tccgatccga tccccgagct     1380
ggcaggacgc gagctggctg ggactcctct tgacagagga agggcttac acaccaccct     1440 cctaggctgc ccaatacaag aaacagtctt gcagccagac tcctccacac ccagcgaaca     1500
gaccgtccaa ggcgctccgg tgtttcgaga acaccgaagt cccctccctg ctaaagggcg     1560
```

-continued

```
cgtgagctct gctctgcagg aaacctgggc actggaggta gatgggatgg gtggcggcgg      1620
gtagagccgg ggcgcagcgg aaagcaaacg ccggaggcaa acggggcgca ggagagggga      1680
gattgggtgc cgccgtaggg gccagggtga aagccgggcg cggacgggaa ccgaggggaa      1740
ctgggcactg gagccaagcg ggctctggaa gggacgcgcg ggcaggaacc cgcgagcgct      1800
ggggaggggc ttgcttggcg atctgccccg gactccctag agccgcagaa ccgccggtgg      1860
aggcggggtg ctaggagttg gcggggccgg gtgggggtgg gggggaacca gagaggggcg      1920
tgccttcgcc aggattggct gcaggagcct gacgcgagnn nccgggggtt ggctcggggg      1980
agtgggagcc gggtgggggtg ggtgctgggt gccggggctg cgggctccgc gagctcagaa      2040
acatgctgag gtcccggcag ctgttccagc agcgacacca ctccagcagc agccgcggcg      2100
gctgcggcgg cgacaggcac cggctccggc ggggaaggcg cccggcgcca tgcctccggc      2160
cccgcgccgc gctgcgctga cctggccgcg acctccctcc gcgcgcccg ccgttcgggc      2220 ctctgggggg ttccccaacc gcggcccaac tccgccacac ccctctcccc cggcctccgc      2280
agctcggcat gggcgcgggg gcgctcgccc tgggcgcctc cgagccctgc aacctgtcat      2340
tcgccgcgcc ggtccccgac ggcgcggcca cggcggcgcg gctgctagtt cccncgtcgc      2400
cgctccgcct cgctgctgac ctcggccagc gagggacccc gctgctgtcg cagcagtgga      2460
cggtcggcat gggcctgctg atggcattca ttgtgctgct catcgtggcg ggcaacgtgc      2520
tggtgatcgt ggccatcgcc aagactccgg ggctgcagac gctcaccaac ctcttcatca      2580
tgtcgctggc cagcgcagac ctggtcatgg gtctgctggt agtgccgttt ggagccacaa      2640
tcgtggtgtg gggccgctgg gagtatggct ccttcttctg cgagctctgg acctcggtgg      2700
acgtgctgtg cgtgacggcc agcatcgaga ccctgtgtgt catcgccctg accgctacc      2760 tcgccatcac gtcgcccttc cgctaccaga gcctgctgac ccgcgcgcga gcgcgggccc      2820
tcgtgtgcac cgtgtgggcc atctcggcgc tggtgtcctt cctgcccatc ttcatgcagt      2880
ggtgggggga caaggacgcc aaggcgagcc ggtgctacaa cgaccccgag tgctgcgact      2940
tcatcatcaa cgagggctac gcgatcacct cttccgtcgt ctccttctac gtgcccctgt      3000
gcatcatggc cttcgtgtac ctgcgggtgt tccgcgaggc ccagaagcag gtgaagaaga      3060
tcgacagctg cgagcgccgc ttcctcagcg gccccgcgcg gctgccctcg cccgcgctct      3120
cgcccgggcg ccgctccct gccgccgcg tggccaacgg gcgcgccaac aagcggcggc      3180
cctcgcgcct cgtggccctg cgcgagcaaa aggccctcaa gacgctgggc atcatcatgg      3240
gcgtgttcac gctctgctgg ctgcccttct tcctggccaa cgtggtgaag gccttccacc      3300
gcgacctggt gcccgaccgc ctcttcgtct tcttcaactg gctgggctac gccaactcgg      3360
ccttcaaccc catcatctac tgccgcagcc ccgacttccg caaggccttc cagcgcctgc      3420
tctgctgcgc gcgccgggcc gcctgcggga gccacgggc cgccggggac ccgccgcgcg      3480
ccgcgggctg cctggcggtg gcccggccgt cgccgtctcc cggggccgcc tcggacgacg      3540
acgacgacga cgacgaagac gacgtcgggg ccgcccgcc cgtgcgcctg ctgcagcct      3600 gggctggcta caacggcggg gcggcggcga acagcgactc gagcccggac gagccaagcc      3660
gcccgggctg cggctcggaa tccaaggtgt agggacgggc gccctcccc gccttccccg      3720 gcttccccag tccgggagcg ggctgtgcgc tccaggagca agagaacccg ggcgmccctg      3780
aaccgcttcc ccgggaaaga ggtctgtgtt tactcgagac cgtaaagcag gtgaactcga      3840
agcctgcgaa cctcgtctgc atcatccaag ggcaaatagg aaagccacgg accgtcgcac      3900
```

-continued

| | |
|---|---|
| agaaaggaaa gtttggggag aggtgggaga agtttgggga ggggtggaag agtggcttac | 3960 |
| tgattgttct tggggttctt tttcctgttt ctggtccagc cttctgtgtg tgcgtgtgat | 4020 |
| gcatctttag agtccctcct cccccgccc ccccgcgacg tggcttttaa cactttctgc | 4080 |
| gatgactggg aagggaaggg ggaagcgtta ggaggtaaaa gtctctcgac ttagtttcca | 4140 |
| tcccattcct gggaacagaa gcggtcagcc agagagagag gagagagaat gacactttat | 4200 |
| caggacgttg tttcctttg cttttcagag aaataccatt ttaatttctg aggaattatt | 4260 |
| tctcctgttc tgaaagccga gggcaaggat ggatgcaaaa atcgcgtttc aggaagtttt | 4320 |
| atgctcttct tggaacaagc ctcaccttgc ttcccttcg gagggcaagc gggctgtccc | 4380 |
| tgaacgcctc ctcggtggtc aggctgaggg gttcctacct cactcacacg gtgcacattg | 4440 |
| cacggccaga tagagagact tgtttatatt aaacagctta tttatgtatc aatactagtt | 4500 |
| ggaaggacca ggcgctgagc cttcgtgaca tgtgactctg tccattgaag acaggacaga | 4560 |
| aaaggaaaa agaaaaaagg aaaacaattc agattactgc acatgtggta tagacaaaaa | 4620 |
| atcaaaacaa aaagccgtg attcaaagtg gcattttttt tgcacagtat taggaactgt | 4680 |
| aaagtccaca gaaaatgtta tttgcacaaa aagaaatgaa atatttttta atgggagtgg | 4740 |
| ggtggggca | 4749 |

<210> SEQ ID NO 190
<211> LENGTH: 2170
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 190

| | |
|---|---|
| gactccccag agctgctgaa ccgccggggg gaggggtgg gggagttggc ggggggggg | 60 |
| ggggagaacc agatcggggc gtgcttcctc ggattgctgc aatagctgac gcgaggcccc | 120 |
| ggggggttggc tccagggagt gggatgggag cgggtgggt ggtgctgggt gccggggctg | 180 |
| cgggttccgg cgctcagaaa ctgctgaggt cgcagctgtc cagcagcgac accgctccag | 240 |
| cagcagcggc ggcggcgggg cggcgacgcg cacagcctgg cggggaaggc gccctgcgcc | 300 |
| catgcctccg gcccccgccg cggcgccctg accggccgcg acctccctcg tcgcgccccg | 360 |
| ccgcccgggc cttgggggg tcccgaccgc gcccaactcc gccacacccc ccgccccgc | 420 |
| ctccgcagcc ggtatggggc gggggcgtcg ccctgggtgc ctccgagccc tgcaacctgt | 480 |
| catcggcgcg ccgctcccga cggccggcca ccgcggcgcg gctgctggtg cctgcgtccc | 540 |
| ctccgcctcg ctctgacccc accagcgagg gatccgtgca gctgtcgcag cagtggacgg | 600 |
| tggcatgggc tcctgatgcg ctcatcgtgc tgctcatcgt ggcgggcaac gtgctgggat | 660 |
| cgtggcatcg ccaagcgccg aggctgcaga cgctcaccaa cctcttcatc atgtcctggc | 720 |
| caggccgacc tgtcatgggg ctgctggtgg tgccattcgg ggccaccatc gggtgtgggg | 780 |
| cgctgggaga cggctccttc ttctgcgagc tctggacgtc ggtggacgac tgtgcgtacg | 840 |
| gccagttcga gaccctgtgt gtcatcgccc tggaccgcta cctcgcatca cgtccccttt | 900 |
| cgcaccagag cctgctgacc cgcgcggcac gggcctcgt gtcaccgtgt ggccatctcg | 960 |
| ccctggtgtc cttcctgccc atcctcatgc actggtggcg acaagggc cgaggcagcc | 1020 |
| gctgctacaa cgaccccaag tgctgcgatt tcgtcacaac agggctacgc catcctcgt | 1080 |
| ccgtggtctc cttctacgtg cccttgtgca tcaggccttc gttacctgcg gtgttccgcg | 1140 |
| aggcccagaa gcaggtgaag aagatcgaca ctgcgagcgc gctttctcgc agccccgcgc | 1200 |

```
ggccgccctc gcccgcgccc tcgcccggtc cccgctcctg ccgccctgcc gcagccccgg    1260
tagccaacgg gcgcaccagc aagagcggcc ctccgcctcg tgccctgcga gagcagaagg    1320
cgctcaagac gctgggcatc acatggcgt ttcacgctcg ctggctaccc ttcttcctgg     1380
ccaacgtggt gaaggcctcc accgcgactg gtgcccaccg cctcttcgtc ttcttcaact    1440
ggctgggcta cgccactcgg ccttaacccc atctctactc ccgcagccct gacttccgca    1500
aggccttcca gccctgctct gtgcgcgcgc gggtcgcccg cgggagctgc gcggccgccg    1560
gggatgggcg cgcgcctcgg ctgcctgcgg tggcccggcc gccgccgtcg cccggggccg    1620
cctcggcgac gacgagacga agaaacgtcg gggccgcgcc gccggcgccc ctgctggagc    1680
cctggccgga taaacggcgg gcggcacgtg acagcgactc gagcctggac gagcggacgc    1740
cgggggccgg cctcggaacc aaggtgtagg gcccagcgct ccctccccac ctcccagggg    1800
gatgcagctc tgcgcgagag aagagaaccc ggcgccccga aaggcttccc ggggatgagg    1860
agactgtgtt tatcgagacc gaaagcaggt gaactcgcaa acctcgtctg ctcatctaag    1920
caaacagaaa gccggaccgc tgcacagaaa ggaaagtttg ggagggtgg agagtggttg      1980 ctcattttct tgagttcttt tctctgtttg tggtccgtcc tcctttgtgt gtgctgtgat    2040
gcactttaga tttttattcc cccaggtggt ttttaacact tttgcgaaga cagggaaggg    2100
tgggagaagc aggagagttt ttaaaaaggt gtctcaactg gcttccatcc gttcccggga    2160
cggagcagtc                                                          2170
```

<210> SEQ ID NO 191
<211> LENGTH: 3563
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 191

```
ggtaccagag tacaaacgtc ggtgttaagg tgttggtact ggagtcaaaa gtctgaagcg      60
tcattctctg agttctttta cgcggggtgg gggttggggg tgggcgtgt catttactcc      120 ggacttaatg ttgcccaaac ttctccttta tactcagaac tcatccatcc ttttccttag    180
ctgggattgg gaacgtgtgt gtccaactgg tccttggcgt tggagttaca gccacaaacc    240
ttcccttcct tccccatcca ctgcacttga gggagagaga gacagctctg cggaagaaca    300
gcgcccagag gcctttctga cagatggcac tctgctcccc aatccgcctg gctgcaaagt    360
ttcctctata actaacaccc acttcctatt ccccaagtgt cattctggcc gggtcccctc     420
gcgatcggga agagccaggc tgcctgatgg cagaacagtc tcacagctaa attctctaat    480
cccacagata ggctgtccaa ggcatctccg gaagccagca agtttccctt ctagctacca    540
ggaccatgca ctagaggtag aaaggcgagg ggctacgggg cgccgaaggg aaaccggctc    600
tgcgggaggg caaaatgaga gctgggtgca gggcaagcgg acaccacttg ggcggtgggg    660
tgggcacagg aggccggcgg ggcacccaga gggcgcagca gaccagactc tggaagagcc    720
tgagcaggaa agggcgcgct cgctgagccc gtgggtgccg gctgcgtagt ccaccgcaat    780 cttttggagcc tttcaatcgc ggtggagggg gtgctggtg ttgggggtgg ggcaccattg    840
ttcgggggcg tgccttggac gcgattggct gcgggagcct gacgcgcggc ccggggctg    900 gctgggggt agggagcgag tgggggggag gtgctggtg ttggagcccc ggccccgcgc      960
gctcagaaac atgctgagtc ccggcaactc ttccagcagc gacccgtcca gcagcagcgg    1020
```

```
cggcggcggc ggcgggacac ggcttggcta cggaggagaa ggcgccggcg tccatgcctc    1080
cggccccaag ccgggctgcc ctgacctggc cgcgacctcc cccgtccccg cgcgcgcccc    1140
cagccccggc tctggggtgc ttcccaggcg cggcccagtc cgccacaccc cccgcgcccg    1200
gcctccgaat cggcatgggc gcggggggcgc tcgccctggc gcctccgaac cctgcaacct   1260
gtcgtcgccg cgccgctgcc cgacggcgcg gccaccccggc acgactgctg gtgctcgcgt   1320
cgcctccgcc tcgctgctgc tccagccag cgaggctcag cgccgctgtc gcagcagtgg     1380
acccgggtat gggcctactc ctggcgctca tctgctgctc atcgtagtgg gcaacgtgtt    1440
gtgatcgtgg ccatcgccaa gaccccgcgg tgcagacgct caccaacctc ttcatcatgc    1500
cctggccagc gccgatctgg tcatgggatg ctggtggtgc ctttcggggc caccatttgg    1560 tgtgggccg ctgggagtac ggctcctctt ctgtgagctc tggacttcgg tagactgcta     1620
tgtgtgacgg ccagcatcga gacctgtgtg tcatcgccct ggaccgctac ctcccatcac    1680
gtcgcccttt cgctaccaga gctgctgacg cgcgcgcgag cgcgggccct ctgtgcacag    1740
tgtgggccat ctccgcgctg tgtccttcct gcccatcctc atgcactggg gcgggccgag    1800
agcgacgaag cgcgccgcgc tacaacgacc ccaagtgctg cgatttctca ccaaccgggc    1860
ctacgccatc gcctcgccgt cgtctccttc tacgtgcccc tgtgctcatg gccttcgtgt    1920
acctccgggt gttcgcgagg cccagaaaca ggtgaagaag atcacagctg cgagcgccgc    1980
ttcctcagcg gccgccccgg ccgccctcgc ccgcgccctc gcatcaccag gccaccgcg     2040 ccccgcagac cgctggccaa cgggcgctcc agcaagcggg gccgtcgcgc ctcgtggctc    2100
tgcgagagag aaggcgctca agacactggg catcatctgg gtgtgttcac gctctgctgg    2160
ctgccctctt cctggccaac gtggtgaaag ctttcaccgc gacctggtgc cggatcgcct    2220
cttctcttct tcaactggct gggctacgcc aaccggcctt caaccccatc atctactgcc    2280
gcgccccgac ttccgcaagg cttccagcg ctgctttgct gcgcgcgccg ggccgcctgc     2340
gacgccgcgc agcccacggg gaccggccgg cgcctcgggc tgcctggcga gagctgggcg    2400
ccgccgtccc ccggggctcc ttcggacacg acgacgatga cgccggggcc accccaccgc    2460
gcgcctgttg gagccctggg ccggcgcaac ggcgggacga ccactgtgga cagcattcga    2520
gcctggacga gccgggacgc caggcttctc ctccgagtcc aaggtgtaga ggccaggctc    2580
tccgggcgca cggacgccgc tcccatagtc ccgggctgga cacgggctct catccctaga    2640
ggaagagagc ccgcctgggc cctgagccgc tccccagggg agagaggaat ttctgtttac    2700
tcaagaccga aagcagggaa tgcgaagccc acagatcttt tgaatctccg agacgtacag    2760
aaaagccccg gaccggcgtt gcgcaaaaag gaaagtttgg gagtgttggg agagtgtggc    2820
ttagtgtggc ttatggcttg tcttgagttc ctttctctct gagttcggcc tttcgtgtgt    2880
ttaatgcacc ttaggcaccc cccccccgtg ggttttgaca tttctgcaag gacccgagtg    2940
gaaactaggg gggagggggaa gggggagggt ggagtctaca cctgccttct acttcacacc   3000
taggaactaa gtgttcagct ctggtttggg gtgggccagg agcggtgata attagccagg    3060
aagtgtcctt ttgctttcta aagaaattgc atataattcc ggagtattgg tgtctcctta    3120
aagaaggggg ggaaaggtgg ctgagaaaca gacaatctgg tttcgagaaa ctatttgtgg    3180
acacggttca ccttgctttc tcctggaggg aaaccctgtc cctgcgcgcc tcggtggtct    3240
gctgtgggtc ctctacctca ctctgtgcta ttgcacagca agatagaaag acttgttata    3300
ttaaacagct tatttatgta tcaatatagt tggaaggacc aggcgctgag tctcttctgt    3360
gacatgtgat tctgtcaact aaagtaggac agaacaaaag gaaacagttg ggatattgca    3420
```

-continued

| | |
|---|---|
| catgtggcta aaaacaaaga tgcaaaaaaa aaaggcagtg gttgaaaggc cttttgcgca | 3480 |
| gtgttagaca ttgtaaaatc atagaagttg ttaacttgca caaaaaatta atattttaa | 3540 |
| tgggacgggg aggtgggcga tct | 3563 |

<210> SEQ ID NO 192
<211> LENGTH: 4401
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 192

| | |
|---|---|
| ccaaggaatc tgaaatcgca gttcatgacg tcagcataaa ccgacagtac cttttttgttt | 60 |
| gtattgaccc agctcaaatt ataaaatcac atgagtaata aaacacaaaa tacaggtgtt | 120 |
| gtcactgaaa agcctaaaat gtaactaaac gcgttttccc ccctcgcggt ggtatcattt | 180 |
| actctgtatc tcaacgtttc tgtctcccta agactctccc tttatatcgt gagcacacat | 240 |
| ttttgcatca tgctcacaca ttcattagct aggactgagg agtgtgtacg attccaacgg | 300 |
| gccctcagcg ttagctgtta gatgcacaaa ccttcacttc cttccacat ctactgcact | 360 |
| tgaggttcaa cagaggatcc ttgcaagaac agtgcccaga gagcattctt gacagatgcg | 420 |
| cgcttagctc cagcaacccg ctctgctggg aagtttcttc taaccactaa cacccacctc | 480 |
| caatccccca agctgtcacg acgcaggctg gctgggtccc gtcttgacgg gggaagggtt | 540 |
| ttacacacat cctgctaggc tgccccacat cacaaccaag ctcgcagggc aaactcctcc | 600 |
| aagcctggcg gacaagctgt cccaggcgct ctggcgcttc ctgaacacca aggtcccctc | 660 |
| cgcgctcaag ggagctagcg cactgttacg cagggaaccc cggcactgca ggtcgagggg | 720 |
| atgccgaggg agcgggggcg cagcaggcag ccgactgctg taggcaaacg gcgcgcagga | 780 |
| ggcaaacgag gcgcaggagc cggtgcgaga gcgagtgggc gctgagagag ggggcggggc | 840 |
| cccagggggg aggcgagcgc gggaggggggc acgggagaac agggaccagg aaccagcggg | 900 |
| cgcaggaagg ggtgcgtccg caagaacccg cgggcgcacg ggaggcacta gctccacgat | 960 |
| cagctcggga ctctcaggag ccgctcaatt gccaacggga gggggctgcg gggagttgga | 1020 |
| ggttggggg gctgaccaga cggggcgtg cctttgcccg gattggctgc aggaggctga | 1080 |
| cgcgaggccc cggggttgg cttgggagt gggagcgggg tggggtggt gctgggtgcc | 1140 |
| ggagctgcgg gcccggcgcg ctcagaaaca tgctgaggtc ccggcggctc ttccagcagc | 1200 |
| ggcagcggct ccagcagcag cggcggcggc ggcggcggcg gcagcgacag cgctcggctc | 1260 |
| cggcgggaaa ggcgcccggc gcccatgcct ccggcccgg gccgcggctg ccctgacccg | 1320 |
| gccgcgacct ccctctgcgc accccgccgt ccaggcttct ggggtgttcc caaccaagg | 1380 |
| cccagccctg ccacacccc cgcctccggc ctccgcaact cggcatgggc gcgggggcgc | 1440 |
| tcgtcctggg cgcctccgag cccggtaacc tgtcgtcggc cgcaccgctc cccgacggcg | 1500 |
| tggccaccgc ggcgcggctg ctggtgcccg cgtcgccgcc cgcctcgttg ctgcctcccg | 1560 |
| ccagcgaagg ccccgagccg ctgtcgcagc agtggacggc gggcatgggt ctgctgatgg | 1620 |
| cgctcatcgt gctgctcatc gtggcgggca acgtgctggt gatcgtggcc atcgccaaga | 1680 |
| cgccgcggct gcagacgctc accaacctct tcatcatgtc cctggccagc gccgacctgg | 1740 |
| tcatgggct gctggtggtg ccgttcgggg ccaccatcgt ggtgtgggc gctgggagt | 1800 |
| acggctcctt cttctgcgag ctgtggacct cggtggacgt gctgtgcgtg acggccagca | 1860 |

-continued

```
tcgagaccct gtgtgtcatc gccctggacc gctacctcgc catcacctcg cccttccgct    1920
accagagcct gctgacgcgc gcgcgggcgc ggggcctcgt gtgcaccgtg tgggccatct    1980
cagccctggt gtccttcctg cccatcctca tgcattggtg gcgggcggag agcgacgagg    2040
cgcgccgctg ctacaacgac cccaagtgct gcgatttcgt caccaaccgg gcctacgcca    2100
tcgcctcgtc cgtggtctcc ttctacgtgc ccctgtgcat catggccttc gtgtacctgc    2160
gggtgttccg cgaggcccag aagcaggtga agaagatcga cagctgcgag cgccgtttcc    2220
tcggcggccc cgcgcggccg ccctcgccct cgccctcgcc ctcgccctcg ccggtccccg    2280
cgccgccgcc cggacctccg cgccccgccg ccgccgctgc caccaccgcc ccgctggtca    2340
acggacgtgc gggtaagcgg cggccctcgc gcctcgtggc cctgcgcgag cagaaggcgc    2400
tcaagacgct gggcatcatc atgggcgtgt tcacgctctg ttggctgccc ttcttcctgg    2460
ccaacgtggt gaaggccttc caccgcgagc tggtgcccga ccgcctcttc gtcttcttca    2520
actggctggg ctacgccaac tcggccttca accccatcat ctactgccgc agccccgact    2580
tccgcaacgc cttccagcga ctgctctgct gcgcgcgcag ggctgcccgc cggcgccacg    2640
cggcccacgg agaccggccg cgcgcctcgg gctgtctggc ccggcccgga ccccgccgt    2700 cgcccggggc cgcctcggac gacgacgacg acgatgtcgt cggggccacg cagcccgcgc    2760
gcctgctgga gccctgggcc ggctgcaacg gcggggcggc ggcggacagc gactcgagcc    2820
tggacgagcc gtgccgcccc ggattcgcct cggagtccaa ggtgtagggc ccggcgccgg    2880
gcgaggacgc cgggcacccc gggaggagga gagcccgggc gccccggaac gacttccgg    2940 gggaacgagg agatctgtgt ttactcaaga ccgaaagcag gtgaactcga agcccacaat    3000
cctcgtctga atcatccgag gcaaacagaa aagccacgga ccattgcaca aaaaggaaag    3060
tttggggagg gatgggagag tggcttgctg atgttccttg gttttttttc tttctttctt    3120
cctttttttt ttttttttc tgtttgtggt ccggccttct tttgtatgtg cgtgtgatgc    3180
atctttagat tttttttccc ccacgttggt ttttgacact ctctgcgagg accggagtgg    3240
aagttgggtg ggtacgggaa aggaagaagc attaggaggg gattaaaatc gatcagcgtg    3300
gctcctatcc ctttcccagg aacaggagca gtctaccagc cagagggagg agaatgacag    3360
tttgtcaaga cgtatttctt ttgctttcca gataaatttc attttaattt ctaagtaatg    3420
agttctgctg tcatgaaagc aaagagaaag gatggaggca aaaaaaaaa aattcacgtt    3480 tcaagaaatg ttaagctctt cttggaacaa gccccacctt gctttccttg tgtagggcaa    3540
accggccgtc ccccgcgcgc ctgggtggtc aggctgaggg atttctacct cacactgtgc    3600
gtttgcacag cagatagaac gacttgttta tattaaacag cttatttatg tatcaatatt    3660
agttggaagg accaggcgca gagcctctct ctgtgacatg tgactctgtc aattgaagac    3720
aggacattag agagagagaa acagttcaga ttactgcaca tgtggataaa acaaaaaca    3780 acaaaaaaag gagtggttca aaatgccatt tttgcacagt gttaggaatt acaaagtcca    3840
caggagatgt tacttgcaca aaaagaaatt aaatattttt taaggggga ggggctgggc    3900 agatcttaaa aactaaaata aaattcaaac tctacttctg ttgtctagta tgttattgag    3960
ctaatgattt attggggaaa atacctttt atactccttt atcatggtac tgtaactgta    4020
tccatattat aaatataatt atcttaagga tttttattt ttttttttt atgtccaagt    4080 gcccacgtga atttgctggt gaagttagc acttgtgtgt gaactctact tcctcttgtg    4140
tgttttacca agtatttata ctctggtgca actaactact gtgtgaggaa ttggtccatg    4200
tgcaataaat accaatgaag cacaatcaag attatgtact gtgtgtctgt aaagggtcag    4260
```

```
tgataatgaa aaagacagtt tgttttgttc aaaatataga ctggatttcc catagagctc    4320
ttttaataga ctttcatgac tcaataacat agcaaaatgc ctccagacct aaataaggtg    4380
tttacctact gagagctgca g                                              4401
```

<210> SEQ ID NO 193
<211> LENGTH: 1525
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 193

```
gacctccccg cgcgggcccc gcagcccggg ctcctggggt gctccccagg cgcggcccag      60
ccccgccaca cccccgccc cggcctccg cagctcggca tgggcgcggg ggcgctcgcc       120
ctgggcgcct ccgaaccctg caacctgtcg tccgccgcgc cgctgcccga cggtgcggcc    180
accgcggcgc ggctgctggt gctcgcgtcg cctcccgcct cgctgctgcc tccagccagc    240
gagggctcag cgccgctgtc gcagcagtgg accgcgggta tgggcctact cgtggcgctc    300
atcgttctgc tcatcgtggt gggtaacgtg ctggtgatcg tggccatcgc caagaccccg    360
cggctgcaga cgctcaccaa cctcttcatc atgtccctgg ccagcgctga tctggtcatg    420
ggattgctgg tggtgccttt cggggccacc atcgtggtgt ggggccgctg ggagtacggc    480
tccttcttct gcgagctctg gacttcggta gatgtgctgt gtgtgacggc cagcattgag    540
accctgtgtg tcatcgccct ggaccgctac ctcgccatca cgtcgccctt tcgctaccag    600
agtttgctga cgcgcgcgcg agcgcgggcc tcgtgtgca cagtgtgggc catctcggcg    660
ttggtgtcct tcctgcccat cctcatgcac tggtggcggg ccgagagcga cgaagcgcgc    720
cgctgctaca cgaccccaa gtgctgcgat ttcgtcacca acaggccta cgccatcgcc     780 tcgtccgtcg tctccttcta cgtgcccctg tgcatcatgg ccttcgtgta cctgcgggtg    840
ttccgcgagg cccaaaaaca ggtaaagaag atcgacagct gcgagcgccg cttcctcggc    900
ggcccagccc ggccgccctc gcctgagccc tcgccgtcac ctgggccacc gcgccccgca    960
gactcgctgg ccaacgggcg ctccagcaag cggcggccgt cgcgcctcgt ggctctgcgc   1020
gagcagaagg cgctcaagac actgggcatc atcatgggtg tgttcacgct ctgctggctg   1080
cccttcttcc tggccaacgt ggtgaaggct ttccaccgcg acctggtgcc ggatcgcctc   1140
ttcgtcttct tcaactggct gggctacgcc aactcggcct tcaaccccat catctactgc   1200
cgcagccccg acttccgcaa ggcttttcag cgcctgctct gctgcgcgcg ccgggccgcc   1260
tgcagacgcc gcgcagccca cggggaccgg ccgcgcgcct ccggctgcct ggcgagagct   1320
gggccgccgc cgtcccccgg agctccctcg gacgacgacg acgacgacgc cgggaccacc   1380
ccaccggcgc gcctgctgga gccctggacc ggctgcaacg gcgggacaac cactgtggac   1440
agcgattcga gcctggacga gccggggcgc cagggcttct cctcggagtc caaggtgtag   1500
agagccaggc tctctgggcg cacgg                                         1525
```

<210> SEQ ID NO 194
<211> LENGTH: 1584
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 194

| | |
|---|---|
| accaccaacg tggcacctgc agctgaggga ctagaaaact ccatagccca gaggagtcac | 60 |
| tggcagccac aactgtactg aaagtgtagc agctcacaag cccccggctt attcatccag | 120 |
| gagacagaga gactggcaca gtccagccca gtggcacgag agtctgcacc aaccagggqg | 180 |
| agttatagtt tctggacaca agagactacc tggcatcccg ctggcaccga cactttcttt | 240 |
| ctgttctgat attctgttgc ccaaatgatc tgaggctcca ggctaggacc tatgcccatc | 300 |
| atgggagacg gttgggggcc tatggagtgc aggaacaggt ctggtacccc tacaacagtg | 360 |
| cccagcccta tgcacccccct gcccgagctc actcaccagt ggactatggg aatgactatg | 420 |
| ttcatggcgg ccatcatcct cctcatcgtc atgggcaaca tcatggtcat tgtggccatt | 480 |
| gggaggaacc agaggctcca gaccttgacc aacgtcttca tcacgtcctt ggcttgtgcc | 540 |
| gacctcatta tgggtttgtt tgttgtgccc cttggtgcca cgttggtggt gagtggcagg | 600 |
| tggctgtacg ggtcgatatt ctgtgagttc tggacgtcag tggacgtatt gtgcgtcacg | 660 |
| gcgagtatag agaccctgtg cgtcatctcc atcgaccgct acatcgccat cacctcaccc | 720 |
| ttccgctacc agagtctcct gaccaagggc cgtgccaagg aatcgtgtg cagcgtgtgg | 780 |
| ggcatctcag ccctggtctc gttcctgccc atcatgatgc actggtggag ggacactggc | 840 |
| gacccctgg ccatgaaatg ttacgaggat cctgggtgct gtgattttgt caccaacaga | 900 |
| gcttacgcca tcgcctcgtc catcatctcc ttctatttcc cactcatcat catgatcttc | 960 |
| gtctacatca gggtcttcaa ggaggcgcag aagcagatga agaagattga caagtgcgag | 1020 |
| ggcaggttct cccatagcca cgtcctgagc cacggcaggt ccagccggag gatcctctcc | 1080 |
| aaaatcctgg tggccaaaga gcagaaagcc ttgaagaccc tcgggattat catgggcacc | 1140 |
| ttcaccctgt gctggttgcc cttcttcttg gccaacgtgg tcaatgtctt ctacaggaac | 1200 |
| ctgatcccag acaaactctt cctcttcctc aactggctgg gctacgccaa ctccgcgttt | 1260 |
| aaccccatca tctactgcag gagcccagac ttcaggaagg ctttcaagag actcctgtgt | 1320 |
| tgccccaaaa aggcagatcg gcacctccac actactgggg agctctcccg atactcgggg | 1380 |
| ggctttgtta actcttagga caccaatgct ttgggtatgt gttctgaatg taatgggtg | 1440 |
| cggacgtcat tggactgaaa ttaattattt attgtgggtc ggagggagat tgaataagtg | 1500 |
| ggtgcgggc cccaaataac aggtaggttc caggcaacct cactgcagat tcttggaatg | 1560 |
| tagagggttc cccaggatag gagt | 1584 |

<210> SEQ ID NO 195
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 195

| | |
|---|---|
| ccgcgcccat gccga | 15 |

<210> SEQ ID NO 196
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 196

| | |
|---|---|
| agccgtaccc gcgcc | 15 |

```
<210> SEQ ID NO 197
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 197
ccgcgcccat gccga                                                    15

<210> SEQ ID NO 198
<211> LENGTH: 15
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 198
agccgtaccc gcgcc                                                    15

<210> SEQ ID NO 199
<211> LENGTH: 18
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 199
ctccgaagct cggcatgg                                                 18

<210> SEQ ID NO 200
<211> LENGTH: 21
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 200
gcacgtctac cgaagtccag a                                             21

<210> SEQ ID NO 201
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 201
aggcagtgac cctcaacatt accag                                         25

<210> SEQ ID NO 202
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 202
ccagtatgca caggtcatcg ttcct                                         25

<210> SEQ ID NO 203
<211> LENGTH: 25
<212> TYPE: DNA
<213> ORGANISM: UNKNOWN
<220> FEATURE:
<223> OTHER INFORMATION: SYNTHETIC OLIGONUCLEOTIDE
```

```
<400> SEQUENCE: 203
atcaaatggg gtgatgctgg tgctg                                              25

<210> SEQ ID NO 204
<211> LENGTH: 25
<212> TYPE: DNA
<213> ORGANISM: UNKNOWN
<220> FEATURE:
<223> OTHER INFORMATION: SYNTHETIC OLIGONUCLEOTIDE

<400> SEQUENCE: 204
caggtttctc caggcggcat gtcag                                              25
```

ANTISENSE COMPOSITIONS TARGETED TO β1-ADRENOCEPTOR-SPECIFIC MRNA AND METHODS OF USE

The present application is a continuation-in-part of U.S. patent application Ser. No. 09/152,717 filed Sep. 14, 1998, and issued Jul. 11, 2000 as U.S. Pat. No. 6,087,343, and PCT International patent application Serial No. PCT/US99/21007, filed, Sep. 14, 1999, and published Mar. 23, 2000 as WO 00/15783, the entire contents of each of which is specifically incorporated herein by reference in its entirety without disclaimer.

The United States government has certain rights in the present invention pursuant to Grant HL-27334 from the National Institutes of Health.

1.0 BACKGROUND OF THE INVENTION

1. Field of the Invention

The present invention relates generally to the fields of cardiovascular disease and hypertension. More particularly, it concerns antisense oligonucleotide compositions and methods that are useful for reducing hypertension, cardiac hypertrophy, and myocardial ischemia in animals, particularly in mammals such as humans. Specifically, the invention provides antisense oligonucleotide and polynucleotide compositions capable of binding to $\beta_1$-adrenoceptor ($\beta_1$-adrenergic receptor, $\beta_1$-AR)-specific mRNA and inhibiting translation of the $\beta_1$-adrenoceptor mRNA, thereby decreasing the number of $\beta_1$-AR polypeptides in cells capable of expressing this mRNA. Disclosed are antisense oligonucleotide and peptide nucleic acid compositions, pharmaceutical formulations thereof, and vectors encoding antisense oligonucleotides that specifically bind $\beta_1$-AR mRNA and alter expression of the mRNA in a host cell.

2. Description of Related Art

1.2.1 Hypertension

Hypertension is the result of increased arterial resistance to blood flow and left untreated can lead to various pathological consequences. Hypertension affects approximately 40 million people in the United States. Heart attack (Nicholls et al., 1998), kidney damage (Agodoa, 1998), stroke (Chamorro et al., 1998) and loss of vision (Satllworth and Waldron, 1997) are typical conditions that result from high blood pressure. When blood vessels are subjected to high pressure for extended periods of time, they respond by thickening, vasospasm, and internal build-up of lipids and plaques, a condition known as arteriosclerosis. Arteriosclerosis further causes a decreased blood flow to the kidneys, which respond by releasing the protease renin. An overactive renin-angiotensin system is often implicated in the development of hypertension and cardiovascular disease (Nicholls et al., 1998).

Hypertension is often called the "silent killer," since half of the population afflicted with high blood pressure are unaware of the condition. Thus, an initial step in combating hypertension is early detection. Following diagnosis, actions must be taken to control the disorder.

1.2.2 Treatment of Hypertension

Currently, four major categories of hypertensive drugs are administered to treat high blood pressure: (1) Diuretics, typically the drug of choice when the abnormal blood pressure is not very high, increase the rate at which the body eliminates urine and salt, resulting in decreased blood pressure by reducing volume (Moser, 1998); (2) β-adrenergic blockers (β-blockers), typically prescribed in combination with diuretics, lower blood pressure and heart rate (Rodgers, 1998); (3) Calcium channel blockers work by preventing the entry of calcium into cells, which reduces vasoconstriction (Rosenthal, 1993); (4) angiotensin converting enzyme (ACE) inhibitors prevent the narrowing and constriction of blood vessels by blocking the production of the vasoconstrictive peptide angiotensin II (AT-II), a product of ACE (Rosenthal, 1993).

Unfortunately, the short lasting effects of these drugs often require multiple, even daily doses to be therapeutically effective. Poor compliance is a major problem with drug regimens and can lead to a hypertensive crisis if the drug is not taken as scheduled.

The sympathetic nervous system plays a crucial role in the regulation of blood pressure (BP), mainly through activating α- and β-adrenergic receptors $\beta_1$-ARs) in the effector organs, including heart, kidney, and blood vessels. Adrenergic-blocking agents, especially β-blockers, are commonly used in the treatment of hypertension, ischemic heart disease, and arrhythmia (reviewed in Sproat and Lopez, 1991). However, β-blockers cause several side effects, which are usually associated with their central nervous system (CNS) reaction (e.g., sleep disturbance, depression, impotence, dizziness and fatigue) and $\beta_2$-adrenergic antagonistic activity (e.g., increase in peripheral vascular resistance, worsening of asthma symptoms). In addition, because of their short half-life (3 to 10 hrs), β-blockers must be taken daily to be effective. Because a cardiovascular disease such as hypertension is a life-lone disorder, longer-lasting treatment without side effects would be desirable.

Although the precise mechanism underlying the antihypertensive effects of β-blockers remains unclear, it is generally accepted that they antagonize the $\beta_1$-AR activity in heart and kidney, decreasing cardiac output and plasma renin activity (Sproat and Lopez, 1991). A new approach to $\beta_1$-blockade has been designed that reduces the number of receptors. Antisense oligonucleotides (AS-ODN) or antisense DNA designed specifically against $B_1$-ARs might represent a new class of β-blockers. Antisense techniques, through a number of mechanisms (Phillips et al., 1997), can effectively downregulate the expression of target proteins. Clinical trials using antisense in targeting AIDS (Akhtar and Rossi, 1996), cancer (Dachs et al., 1997), and other genetic and acquired diseases (Yla, 1997) indicate their potential clinical usefulness. The antisense approach has several potential advantages over β-blockers. First, the specificity of AS-ODNs is based on DNA sequence. Second, AS-ODNs do not have direct CNS effects, because of the negligible transport of these highly polar molecules through the blood-brain barrier (Agrawal et al., 1991). Third, antisense elements tested in different systems produce long-term effects after single treatment (Gyurko et al., 1997). This prolonged effect can be attributed to 2 features of AS-ODN. One is the extended half-life of chemically modified ODN. The half-life 15–20-mer phosphorothioated ODN is 20 to 50 hrs in rats and mice after intravenous injection (Iversen, 1991; Zhang et al., 1995). The other is associated with the nature of antisense inhibition, which provides a delayed yet prolonged blockade of target proteins distinct from the direct competitive antagonists currently available.

1.2.3 $\beta_1$-Adrenoceptors $\beta_1$-ARs, which are distributed in the heart, kidney and blood vessels, play a role in the physiological control of blood pressure. For many years β-blocker drugs have been used for the treatment of hypertension through a regimen of daily dosing. The mechanism of control of blood pressure is not precisely known but the value of beta-blockers in hypertension control has been underscored by the reports of the Joint National Committee on High Blood Pressure recommending β-blockers as the first line of defense in the treatment of hypertension. Current β-blocker drugs, however, have certain disadvantages, including: (1) they have to be taken daily, or twice a day and compliance is a problem; (2) they have central effects, leading to psychological changes that contribute to the problem of patient compliance; and (3) many of the β-blockers now available are not specific for $β_1$-ARs and, therefore, can have untoward side effects.

1.3 Deficiencies in the Prior Art

As can be understood from the above, there remains a need for an effective $β_1$-AR blocker that is highly specific, nontoxic, produces few side effects and does not cross the blood brain barrier to produce psychological changes. Also, a β-blocker that would last several days or weeks would allow patients more flexibility in the regimen of drug dosage by taking drugs infrequently. Thus, the need exists for an effective treatment of cardiac deficiencies (including hypertension, hypertrophy, ischemias, and the like) that circumvents the toxic side effects of existing therapies and provides more specific $β_1$-AR inhibition with longer acting effects for improved patient compliance. In addition, methods for delivery of antisense oligonucleotides and polynucleotides to a host cell, and in particular, non-invasive administration of specific antisense constructs to a mammal such as a human subject is particularly desirable.

2.0 SUMMARY OF THE INVENTION

The present invention overcomes these and other limitations in the prior art by providing antisense nucleic acid compounds and compositions comprising them that specifically inhibit or reduce the expression of an mRNA encoding a $β_1$-adrenoceptor ($β_1$-AR) polypeptide in a host cell expressing the mRNA. More specifically, the subject invention provides antisense oligonucleotides (AS-ONs) and antisense oligo-peptide nucleic acids (AS-PNAs) that can specifically bind to a mammalian $β_1$-AR mRNA, resulting in the reduction or inhibition of translation of the messenger ribonucleic acid (mRNA) into $β_1$-AR polypeptide. Such oligonucleotides and PNA may be readily formulated in pharmaceutically-acceptable vehicles and provided directly to host cells, or administered systemically to mammals that express $β_1$-AR mRNA to reduce the level of $β_1$-AR produced in such cells and affected mammals.

The invention also provides genetic constructs comprising substantially full-length, antisense polynucleotide (AS-PN) sequences operably linked to a suitable promoter that may be used to transform selected cells to endogenously express "antisense" mRNA sequences that are complementary to the native $β_1$-AR mRNA sequence. When expressed in a suitable host cell, these essentially full length anti-mRNAs specifically bind to the native $β_1$-AR mRNA produced in the same host cell, and effectively reduce the availability of native $β_1$-AR mRNA that can serve as a template for the translation machinery of the host cell to produce $β_1$-AR polypeptide.

The antisense compounds and the genetic constructs of the present invention may be prepared in a variety of compositions, and may also be formulated in appropriate pharmaceutical vehicles for administration to human or animal subjects to inhibit or significantly reduce the expression of $β_1$-AR-specific mRNA, and/or to inhibit or significantly reduce the translation of $β_1$-AR-specific mRNA into functional $β_1$-AR polypeptide. The antisense compounds of the present invention, and compositions comprising them provide new and useful therapeutics for the treatment, control, and amelioration of symptoms of a variety of cardiovascular disorders including hypertension, ischemia, cardiac hypertrophy, myocardial infarction, cardiac dysfunction, and diseases of the heart, that result from, or are exacerbated by, expression of $β_1$-AR-specific mRNA in the host cells of the affected mammal. Moreover, pharmaceutical compositions comprising one or more of the nucleic acid compounds disclosed herein, provide significant advantages over existing conventional therapies—namely, (1) their reduced side effects, (2) their increased efficacy for prolonged periods of time, (3) their ability to increase patient compliance due to their ability to provide therapeutic effects following as little as a single dose of the composition to affected individuals.

Preferred antisense compounds for use in the practice of the present invention are those nucleic acid and peptide nucleic acid sequences that specifically bind to a gene or an mRNA encoding $β_1$-AR polypeptide and that inhibit the expression or reduce the level of $β_1$-AR polypeptide in a mammalian host cell that expresses the gene and/or the mRNA.

The compounds of the invention, and the pharmaceutical formulations thereof, permit the development of methods for treating hypertension, ischemia, cardiac hypertrophy, cardiac dysfunction, or other cardiovascular diseases through the administration of at least one antisense compound that specifically binds to a mammalian $β_1$-AR-specific gene or mRNA, wherein the binding of the antisense compound to the gene or the mRNA alters, decreases, inhibits, and/or prevents transcription of the $β_1$-AR-specific mRNA, or, alternatively alters, decreases, inhibits, and/or prevents translation of the $β_1$-AR-specific mRNA into functional $β_1$-AR polypeptide in a host cell. As described above, the present methods offer significant advantages over traditional pharmacological modalities involving drugs that block or interfere with activity of the $β_1$-AR polypeptide (and not the amount of $β_1$-AR polypeptide). The present methods also avoid many of the untoward side effects of conventional therapies, avoid invasive surgical procedures, and are effective in lower, less frequent dosing regimens. The ability to dose less frequently represents a key aspect of improving patient compliance in dosing and reduces administration costs associated with more frequent dosage regimens.

In a first embodiment, the invention provides antisense oligonucleotides that specifically bind to a mammalian $β_1$-AR-specific gene or a mammalian $β_1$-AR-specific mRNA in a host cell, and alter the expression of, or quantity of, $β_1$-AR polypeptide produced in the cell.

In a second embodiment, the invention provides antisense peptide nucleic acids that specifically bind to a mammalian $β_1$-AR-specific gene or a mammalian $β_1$-AR-specific mRNA in a host cell, and alter the expression of, or quantity of, $β_1$-AR polypeptide produced in the cell.

In a third embodiment, the invention provides antisense polynucleotides that specifically bind to a mammalian $β_1$-AR-specific gene or to a mammalian $β_1$-AR-specific mRNA in a host cell, and alter the expression of, or quantity of, $β_1$-AR polypeptide produced in the cell. The antisense polynucleotides represent full-length, or substantially full-length sequences that are complementary to a mammalian $β_1$-AR-specific mRNA, and that when present in a cell that expresses a mammalian $β_1$-AR-specific mRNA, will specifically bind to the $β_1$-AR-specific mRNA, thereby reducing the availability of functional mRNA in the cell from which the cellular protein machinery can translate functional $\beta_1$-AR polypeptide. Preferably, these full-length, or substantially full-length polynucleotides are provided to a cell via a genetic construct that comprises a promoter capable of expressing the complementary mRNA in a selected host cell. Such genetic constructs may be provided to suitable host cells using any one of the conventional gene therapy modalities known to those of skill in the art, such as, for example by one or more of the viral, retroviral, adenoviral, or adenoassociated viral constructs commonly exploited for the delivery and expression of heterologous polynucleotides.

In a fourth embodiment, the invention provides compositions that comprise one or more of the disclosed antisense oligonucleotides, polynucleotides, and peptide nucleic acid compounds and a suitable diluent, carrier, or pharmaceutical vehicle.

In a fifth embodiment, the invention provides pharmaceutical formulations that comprise one or more of the disclosed antisense oligonucleotides, polynucleotides, and peptide nucleic acid compounds and at least one antihypertensive pharmaceutical compound.

In a sixth embodiment, the invention provides pharmaceutical compositions that comprise at least two or more of the disclosed antisense oligonucleotides, polynucleotides, and peptide nucleic acid compounds.

In a seventh embodiment, the invention provides pharmaceutical compositions that comprise at least two or more of the disclosed antisense oligonucleotides, polynucleotides, and peptide nucleic acid compounds in combination with at least one antihypertensive pharmaceutical compound.

In an eighth embodiment, the invention provides therapeutic kits and medicaments that comprise at least one or more of the disclosed antisense oligonucleotides, polynucleotides, and peptide nucleic acid compositions in combination with instructions for using the compositions in the treatment of mammalian cardiac dysfunction or disease. Alternatively, the invention provides kits that comprise at least one or more of the disclosed antisense oligonucleotides, polynucleotides, and peptide nucleic acid compositions in combination with instructions for using the compositions in the preparation of genetic constructs for the development of suitable gene therapy vectors. Likewise, the invention provides kits that comprise at least one or more of the disclosed antisense oligonucleotides, polynucleotides, and peptide nucleic acid compositions in combination with instructions for using the compositions in the formulation of multi-drug "cocktails" for the treatment of one or more pathological conditions.

The invention also provides methods for the treatment of one or more cardiac diseases or dysfunctions employing one or more of the antisense compounds or compositions as described herein.

In each of the embodiments described herein, the oligonucleotide, polynucleotide, or peptide nucleic acid compound comprises a sequence region least 9 to about 35 bases in length, wherein the oligonucleotide specifically binds to a portion of mRNA expressed from a gene encoding a mammalian $\beta_1$-AR polypeptide, and further wherein binding of the oligonucleotide to the mRNA is effective in decreasing the activity of $\beta_1$-AR in a host cell expressing the mRNA.

2.1 Oligonucleotide and Oligo-PNA Compounds

In oligonucleotide and oligo-peptide nucleic acid embodiments, the oligonucleotide or PNA preferably consists of a sequence of from about nine to about 35 nucleotides in length, and preferably comprises a sequence of at least nine, at least ten, at least eleven, at least twelve, at least thirteen at least fourteen, or at least fifteen contiguous bases from any one of the sequences disclosed in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28, as well as the smaller n-mer sequences illustrated in SEQ ID NO:29 through SEQ ID NO:186.

Alternatively, the oligonucleotide or PNA preferably consists of a sequence of from about nine to about 35 nucleotides in length, and preferably comprises a sequence of at least sixteen, at least seventeen, at least eighteen, at least nineteen, at least twenty, at least twenty-one, at least twenty-two, at least twenty-three, at least twenty-four, or at least twenty-five contiguous nucleotides from any one of the sequences disclosed in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53.

Alternatively, the oligonucleotide or PNA preferably consists of a sequence of from about nine to about 35 nucleotides in length, and preferably comprises a sequence of at least twenty-six, at least twenty-seven, at least twenty-eight, at least twenty-nine, at least thirty, at least thirty-one, at least thirty-two, at least thirty-three, or at least thirty-four contiguous nucleotides from any one of the sequences disclosed in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53.

Alternatively, the oligonucleotide or PNA may consist of a sequence of from about nine to about 35 nucleotides in length, and may comprise the entire sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO: 50, SEQ ID NO:51, SEQ ID NO:52, or SEQ ID NO:53.

The oligonucleotide or PNA compound may consist essentially of the sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53, or any one or more of the smaller n-mer sequences illustrated in SEQ ID NO:54 through SEQ ID NO:186.

The oligonucleotide or PNA compound may also consist of the sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53, or any one or more of the smaller n-mer sequences illustrated in SEQ ID NO:54 through SEQ ID NO:186.

As described above, the length of the preferred oligonucleotide or PNA compounds preferably will be on the order of from about nine to about 35 or so nucleotides. As such, in addition to those compounds that are nine nucleotides in length, and those compounds that are 35 nucleotides in length, all intermediate size compounds are also contemplated to be useful in the practice of the present invention. Thus, oligonucleotide or PNA compounds that are ten nucleotides in length, eleven nucleotides in length, twelve nucleotides in length, thirteen nucleotides in length, fourteen nucleotides in length, fifteen nucleotides in length, sixteen nucleotides in length, seventeen nucleotides in length, eighteen nucleotides in length, nineteen nucleotides in length, twenty nucleotides in length, twenty-one nucleotides in length, twenty-two nucleotides in length, twenty-three nucleotides in length, twenty-four nucleotides in length, twenty-five nucleotides in length, twenty-six nucleotides in length, twenty-seven nucleotides in length, twenty eight nucleotides in length, twenty-nine nucleotides in length, thirty nucleotides in length, thirty-one nucleotides in length, thirty-two nucleotides in length, thirty-three nucleotides in length, and thirty-four nucleotides in length are also contemplated to fall within the scope of the present disclosure. In fact, the preferred oligonucleotide or PNA compounds may also be slightly shorter than the preferred range, that is, they may be about six or about seven or about eight nucleotides in length, or they may even be slightly longer than the preferred range (i.e., they may be about thirty-six or about thirty-seven or even about thirty-eight or so nucleotides in length), and may still function to reduce the level of $\beta_1$-AR polypeptide in a cell, and thus, effective in the treatment of cardiac disorders resulting from an elevated level of $\beta_1$-AR polypeptide.

Likewise, there is no obligate requirement that the antisense compounds be exactly 100% complementary to a given target sequence on the mammalian $\beta_1$-AR mRNA. Nor is there an obligate requirement that the antisense compounds be exactly 100% identical to one of the sequences disclosed in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53, or any one or more of the smaller n-mer sequences illustrated in SEQ ID NO:54 through SEQ ID NO:186. In fact, the only requirement is that the oligonucleotide or PNA compound have sufficient homology to the gene or the mRNA encoding $\beta_1$-AR polypeptide so that upon specifically binding to the complementary region, a reduction in either the transcription of the $\beta_1$-AR gene and/or a reduction in the translation of $\beta_1$-AR polypeptide from the mRNA is observed. Therefore, the compounds may have 4 or fewer, 3 or fewer, 2 or fewer, or even 1 mismatch from the target sequence to which it specifically binds, and may still be sufficiently active to cause a reduction in $\beta_1$-AR polypeptide within the host cell. Thus, in addition to those compounds disclosed above that comprise sequences that are 100% identical to the sequences disclosed in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53, or any one or more of the smaller n-mer sequences illustrated in SEQ ID NO:54 through SEQ ID NO:186, the invention also encompasses antisense compounds that comprise sequence regions that are about 99%, about 98%, about 97%, about 96%, about 95%, about 94%, about 93%, about 92%, about 91%, or even about 90% identical to a portion of one of those sequences, so long as the resulting degenerate nucleotide sequence retains sufficient homology so that it specifically binds to the gene or mRNA encoding $\beta_1$-AR polypeptide.

2.2 Polynucleotide and Poly-PNA Compounds

In certain embodiments, the polynucleotide comprises at least 9 contiguous bases from SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53. In other aspects of the invention, the polynucleotide comprises DNA, RNA, PNA, or preferably a derivatized or modified polynucleotide, including phosphorothioate derivates and the like.

Preferably the antisense polynucleotide compound comprises a sequence that is substantially the full-length complement of the $\beta_1$-AR mRNA, wherein binding of the substantially full-length complementary sequence to the $\beta_1$-AR mRNA is effective in reducing the translation of the mRNA into the $\beta_1$-AR polypeptide. Preferably the substantially full-length complementary sequence is comprised within a suitable vector that may be delivered to appropriate host cells. The vector preferably comprises a nucleic acid segment that is operably linked to a promoter sequence that expresses the complementary antisense sequence in the host cell. This complementary near full-length sequence is then able to specifically bind to the substantially full length $\beta_1$-AR mRNA and thereby prevent or substantially reduce the translation of the mRNA into $\beta_1$-AR polypeptide. The term substantially full-length is meant to include those sequences that comprise a sequence that is complementary to a region that is at least about 80% or more of the native $\beta_1$-AR-specific mRNA. Thus, for a $\beta_1$-AR mRNA that is 1000 nucleotides in length, a suitable complementary substantially full-length complement is a sequence that is complementary to a region of at least 800 nucleotides of the particular $\beta_1$-AR mRNA. Likewise, all sequences that are greater than 80% of the full-length sequences (i.e. those that are at least 81% full length, at least 82% full length, at least 83% full length, at least 84% full length, at least lo 85% full length, at least 86% full length, at least 87% full length, at least 88% full length, at least 89% full length, at least 90% full length, at least 91% full length, at least 92% full length, at least 93% full length, at least 94% full length, at least 95% full length, at least 96% full length, at least 97% full length, at least 98% full length, and at least 99% full length are also contemplated to fall within the scope of the present disclosure.

2.3 Compositions Comprising a $\beta_1$-AR Antisense Compound and a Second Cardiac Therapeutic Agent When desirable, the clinician may combine two or more of the oligonucleotide, polynucleotide, or PNA compounds disclosed above to provide an antisense "cocktail" to effect a more substantial reduction in the levels of $\beta_1$-AR polypeptide. Likewise, the patient or animal to be treated may benefit from a combination therapy involving one or more of the oligonucleotide, polynucleotide, or PNA compounds disclosed herein and at least one anti-hypertensive or other cardiac therapy medicament.

For example, the composition may compris at least a first anti-hypertensive agent. In particular embodiments, the anti-hypertensive agent is selected from the group consisting of captopril (Captopril®), enalapril (Vasotec®), ramipril (Altace®), fosinopril (Monopril®), lisinopril (Prinivil®, Zestril®), quinapril (Accupril®), benazepril (Lotensin®), trandolapril (Mavik®), and moexipril (Univasc®). In other embodiments, the anti-hypertensive agent is selected from the group of angiotensin receptor blockers consisting of candesartan (Atacand®), losartan (Cozaar® and Hizaar®), valsartan (Diovan®), and irbesartan (Avapro®).

In still other embodiments, the anti-hypertensive agent is selected from the group of diuretic consisting of dichlorphenamide (Daranide®), spironolactone (Aldactazide®), hydrochlorothiazide (Microzide® and Dyazide®), triamterene (Maxzide®), amiloride (Midamor® and Moduretic®), torsemide (Demadex®), ethacrynice acid (Edecrin®), furosemide (Lasix®), hydroflumethiazide (Diucardin®), chlorothiazide (Diuril®), methylclothiazide (Enduron®), polythiazide (Renese®), chlorthalidone (Thalitone®) and metolazone (Zaroxolyn®).

In still further embodiments, the anti-hypertensive agent is selected from the group of calcium channel blockers consisting of nifedepine (Adalat® and Procardia®), verapamil (Isoptin®, Verelan®, Calan® and Covera®), nicardipine (Cardene®), diltiazem (Tiazac®, Cardizem® and Dilacor®), isradipine (DynaCirc®), nimodipine (Nimotop®), amlodipine (Norvase®), felodipine (Plendil®), misoldipine (Sular®), and bepridil (Vasocor®).

In certain preferred embodiments, the composition may further comprise one or more pharmaceutically acceptable vehicles, exemplified by, but not limited to, liposomes, lipid particles, lipid vesicles, nanoparticles, microparticles, nanocapsules, nanospheres, and sphingosomes to facilitate administration of the antisense composition(s) to the affected patient or animal.

In certain aspects of the invention, the antisense composition of the present invention is specific for an mRNA encoding the human $\beta_1$-AR polypeptide. In particular embodiments, the host cell is a mammalian host cell. In certain preferred embodiments of the invention, the host cell is a human cell. In other preferred aspects, the host cell is comprised within a human.

2.4 Compositions Comprising a $\beta_1$-AR Antisense Compound and a Second Antisense Targeted to Another RAS Pathway Component The present invention also provides compositions that comprise at least a first antisense oligonucleotide, PNA, or polynucleotide specific for a mammalian $\beta_1$-AR-specific mRNA as described above, and at least a second antisense compound specific for a mammalian renin, angiotensin, angiotensinogen, angiotensin type 1 (AT-1) receptor mRNA, or an ACE polypeptide.

In certain aspects of the invention, the second antisense compound is specific for a mammalian angiotensinogen mRNA, or an mRNA that encodes one or more RAS pathway-specific enzymes, such as a mammalian ACE polypeptide. In other aspects, the second antisense compound is specific for an mRNA that encodes a transcriptional factor.

Therapeutic combinations of three or more antisense compound are also provided. These cocktail therapies may comprise at least two antisense compounds specific for a mammalian $\beta_1$-AR-encoding gene or mRNA, and at least a third antisense compound specific for the same mRNA, or alternatively, an mRNA encoding another polypeptide in the RAS pathway as described above. The third antisense compound may be specific for renin, AT-1 receptor, ACE, or angiotensinogen, or another gene or mRNA involved in biochemical pathways involved in producing or regulating blood pressure and/or causing or contributing to hypertension, ischemia, cardiac hypertrophy, or other cardiac dysfunction in an affected animal. Alternatively, the constructs may even be specific for one or more particular transcription factor(s) that regulate one or more genes involved in producing hypertension, ischemia, cardiac hypertrophy, or other cardiac dysfunction in a mammal. Such combined therapy approached using two or more antisense oligonucleotides are particularly desirable where enhanced or synergistic activity towards treating hypertension ischemia, cardiac hypertrophy, or other cardiac dysfunction is achieved.

The invention further provides a method for reducing expression of a gene encoding manmmalian $\beta_1$-AR polypeptide in a host cell, the method comprising providing to the host cell an amount of an antisense oligonucleotide, polynucleotide, or peptide nucleic acid that specifically binds to an mRNA encoding the $\beta_1$-AR polypeptide, effective to reduce the amount of $\beta_1$-AR polypeptide in the cell.

Additionally, the invention provides a method for reducing the number of mammalian $\beta_1$-AR polypeptides in a cell, the method comprising introducing into the cell at least a first antisense oligonucleotide, polynucleotide, or peptide nucleic acid that specifically binds to all, substantially-all, or a portion of the mRNA expressed from a gene encoding a mammalian $\beta_1$-adrenoceptor polypeptide, and further wherein binding of the first antisense oligonucleotide, polynucleotide, or peptide nucleic acid to the mRNA is effective in reducing the number of mammalian $\beta_1$-AR polypeptides in the host cell expressing the mRNA.

The invention also provides a method for decreasing or treating hypertension in an animal, the method comprising administering to the animal an effective amount of at least a first antisense oligonucleotide, polynucleotide, or peptide nucleic acid, wherein the compound specifically binds to all, substantially all, or a portion of the mRNA expressed from a gene encoding a mammalian $\beta_1$-AR polypeptide, and further wherein binding of the compound to the mRNA is effective in decreasing the number of such polypeptides in a host cell expressing the mRNA.

The invention additionally provides a method for treating a disease associated with elevated $\beta_1$-AR activity in a mammal, the method comprising administering to the animal an effective amount of at least a first antisense oligonucleotide, polynucleotide, or peptide nucleic acid compound wherein the compound specifically binds to all, substantially all, or a portion of the mRNA expressed from a gene encoding a mammalian $\beta_1$-AR polypeptide, and further wherein binding of the compound to the mRNA is effective in decreasing the receptor activity or receptor number in a host cell expressing the mRNA, such that a decrease in $\beta_1$-adrenoceptor activity is effected, thereby resulting in amelioration of the disease that results from, or is exacerbated by, an elevated level of $\beta_1$-AR activity in the affected animal.

The invention also provides a method for treating a cardiac hypertrophic or ischemic disease that is associated with, that results from, or is exacerbated by, the presence of, or an elevation in, $\beta_1$-adrenoceptor polypeptides in the affected animal. This method generally involves the administration to the animal of one or more compositions that comprise at least a first antisense oligonucleotide, polynucleotide, or peptide nucleic acid compound, wherein the compound specifically binds to all, substantially all, or a portion of the mRNA expressed from a gene encoding a mammalian $\beta_1$-AR polypeptide in an amount, and for a time sufficient to decrease the number, amount, or activity of the $\beta_1$-adrenoceptor polypeptide in a host cell expressing the mRNA.

Further provides are kits for treating hypertension in a human comprising: (a) a pharmaceutically-acceptable formulation comprising at least a first oligonucleotide of at least 9 to about 35 bases in length, wherein the oligonucleotide specifically binds to a portion of mRNA expressed from a gene encoding a mammalian $\beta_1$-AR polypeptide, and further wherein binding of the oligonucleotide to the mRNA is effective in decreasing the activity, amount, or number of receptor polypeptides in a host cell expressing the mRNA; a pharmaceutical excipient; and (b) instructions for using the kit.

In addition to methods involving the delivery of exogenous oligonucleotide compositions to a host cell, or administration of such compositions to an animal in a therapeutic pharmaceutical formulation, the present invention also concerns gene therapy methods for introducing into a host cell a DNA construct that is transcribed by the cell machinery to give rise to an antisense RNA molecule that specifically binds to a portion of an mRNA encoding a mammalian $\beta_1$-AR polypeptide. In a preferred embodiment, such therapies may be accomplished through the use of viral vectors, such as retro-, adeno- or adeno-associated viruses as described hereinbelow.

Regulation of expression of a gene encoding a mammalian $\beta_1$-AR polypeptide in a mammalian cell genomes may also be achieved by integration of a gene under the transcription control of a promoter which is functional in the host and in which the transcribed strand of DNA is complementary to the strand of DNA that is transcribed from the endogenous $\beta_1$-AR-specific polynucleotide sequence(s) one wishes to regulate. The integrated gene, referred to as an antisense gene, provides an RNA sequence capable of binding to naturally existing RNAs, exemplified by mammalian $\beta_1$-AR polypeptide-specific mRNA, and inhibiting its expression, where the anti-sense sequence may bind to the coding, non-coding, or both, portions of the RNA. The antisense construction may be introduced into the animal cell in a variety of ways and be integrated into the animal genome for inducible or constitutive transcription of the antisense sequence.

Another aspect of the invention provides a pharmaceutical composition useful for inhibiting expression of mammalian $\beta_1$-AR-specific mRNA comprising a pharmaceutical carrier and one or more antisense oligonucleotides of the present invention that specifically bind to and reduce expression of the specific mRNA. Another aspect of the invention provides a method for treating hypertension in a human comprising administering to a subject an effective amount of at least one oligonucleotide composition as described herein, in an amount effective to reduce hypertension in the human, or to ameliorate the degree or extent of hypertension in the patient.

2.5 Definitions

The term "$\beta_1$-AR" refers to polypeptides having amino acid sequences which are substantially similar to the native mammalian $\beta_1$-AR polypeptide amino acid sequences and which are biologically active and/or which cross-react with $\beta_1$-AR polypeptide-specific antibodies raised against a mammalian $\beta_1$-AR polypeptide or peptide fragment thereof.

The term "$\beta_1$-AR" also includes analogs of mammalian $\beta_1$-AR polypeptides that exhibit at least some biological activity in common with native mammalian $\beta_1$-AR polypeptides.

Furthermore, those skilled in the art of mutagenesis will appreciate that other analogs, as yet undisclosed or undiscovered, may be used to construct mammalian $\beta_1$-AR polypeptide analogs or $\beta_1$-AR fusion proteins or identify $\beta_1$-AR-related mRNAs and/or genes using well-known molecular biology techniques, including those described herein. Oligonucleotides complementary to mammalian $\beta_1$-AR polypeptide-encoding mRNAs form the heart of the present invention, especially human $\beta_1$-AR polypeptide-encoding mRNAs.

The oligonucleotides (or "ODNs" or "polynucleotides" or "oligos" or "oligomers" or "n-mers") of the present invention are preferably deoxyoligonucleotides (ie. DNAs), or derivatives thereof; ribo-oligonucleotides (i.e. RNAs) or derivatives thereof; or peptide nucleic acids (PNAs) or derivatives thereof.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an Mrna encoding a mammalian $\beta_1$-AR polypeptide. As such, typically the sequences will be highly complementary to the Mrna "target" sequence, and will have no more than 1, 2, 3, 4, 5, 6, 7, 8, 9, or 10 base mismatches throughout the complementary portion of the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the Mrna and will therefore be highly efficient in reducing, and/or even inhibiting the translation of the target Mrna sequence into polypeptide product.

Substantially complementary oligonucleotide sequences will be greater than about 80 percent complementary (or '% exact-match') to the corresponding Nrna target sequence to which the oligonucleotide specifically binds, and will, more preferably be greater than about 85 percent complementary to the corresponding Mrna target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding Mrna target sequence to which the oligonucleotide specifically binds, and may in certain embodiments be greater than about 95 percent complementary to the corresponding Mrna target sequence to which the oligonucleotide specifically binds, and even up to and including 96%, 97%, 98%, 99%, and even 100% exact match complementary to all or a portion of the target Mrna to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

2.6 Exemplary Antisense Constructs for $\beta_1$-Adrenoceptor-Specefic mRNA

Table 1 lists representative oligonucleotide sequences contemplated for use in the practice of the present invention.

TABLE 1

EXEMPLARY OLIGONUCLEOTIDE SEQUENCES TARGETED TO MAMMALIAN $\beta_1$-AR-ENCODING MRNAS

| SEQ ID NO: | SEQUENCE |
|---|---|
|  | Sequences homologous to rat $\beta_1$-AR mRNA |
| SEQ ID NO:1 | 5'-CCGCGCCCATGCCGA-3' |
| SEQ ID NO:2 | 5'-GGCCGACGACAGGTT-3' |
| SEQ ID NO:3 | 5'-ATGAGCAGCACGATG-3' |
| SEQ ID NO:4 | 5'-GGGCGCTCGCCCTGGCGCCTCCGAACCCTGCAACC-3' |
| SEQ ID NO:5 | 5'-ATGGGCGCGGGGGCGCTCGCCCTGGCGCCTCCGAA-3' |
| SEQ ID NO:6 | 5'-GCCTCCGAATCGGCATGGGCGCGGGGGCGCTCGCC-3' |
| SEQ ID NO:7 | 5'-ACCCCCCGCGCCCGGCCTCCGAATCGGCATGGGCG-3' |
|  | Sequences homolagous to human 131-AR mRNA |
| SEQ ID NO:8 | 5'-GGGTGCTCGTCCTGGGCGCCTCCGAGCCCGGTAAC-3' |
| SEQ ID NO:9 | 5'-ATGGGCGCGGGGGTGCTCGTCCTGGGCGCCTCCGA-3' |
| SEQ ID NO:10 | 5'-GCAGCTCGGCATGGGCGCGGGGGTGCTCGTCCTGG-3' |
| SEQ ID NO:11 | 5'-CCCGGCCTCCGCAGCTCGGCATGGGCGCGGGGGTG-3' |
| SEQ ID ND:12 | 5'-CCGCCCCCGGCCTCCGCAGCTCGGCATGGGCGCGG-3' |
| SEQ ID NO:13 | 5'-ACCCCCCGCCCCCGGCCTCCGCAGCTCGGCATGGG-3' |
|  | Sequences homologous to murine $\beta_1$-AR mRNA |
| SEQ ID NO:14 | 5'-GGGCGCTCGCCCTGGGCGCCTCCGAACCCTGCAAC-3' |
| SEQ ID NO:15 | 5'-ATGGGCGCGGGGGCGCTCGCCCTGGGCGCCTCCGA-3' |
| SEQ ID NO:16 | 5'-GCAGCTCGGCATGGGCGCGGGGGCGCTCGCCCTGG-3' |
| SEQ ID NO:17 | 5'-CCCGGCCTCCGCAGCTCGGCATGGGCGCGGGGGCG-3' |

TABLE 1-continued

EXEMPLARY OLIGONUCLEOTIDE SEQUENCES TARGETED TO
MAMMALIAN β$_1$-AR-ENCODING MRNAS

| SEQ ID NO: | SEQUENCE |
|---|---|
| | Sequences homalogous to sheep β$_1$-AR mRNA |
| SEQ ID NO:18 | 5'-GGGCGCTCGCCCTGGGCGCCTCCGAGCCCTGCAAC-3' |
| SEQ ID NO:19 | 5'-ATGGGCGCGGGGGCGCTCGCCCTGGGCGCCTCCGA-3' |
| SEQ IO NO:20 | 5'-GCAGCTCGGCATGGGCGCGGGGGCGCTCGCCCTGG-3' |
| SEQ ID NQ:21 | 5'-CCCGGCCTCCGCAGCTCGGCATGGGCGCGGGGGCG-3' |
| | Sequences homalogous to porcine β$_1$-AR mRNA |
| SEQ ID NO:22 | 5'-GCGGGGGCGTCGCCCTGGGTGCCTCCGAGCCCTGC-3' |
| SEQ ID NO:23 | 5'-ATGGGGCGGGGGCGTCGCCCTGGGTGCCTCCGAGC-3' |
| SEQ ID NO:24 | 5'-CGCAGCCGGTATGGGGCGGGGGCGTCGCCCTGGGT-3' |
| SEO ID NO:25 | 5'-CCCCCGCCTCCGCA6CCGGTAT6GG6C66GG6CGT-3' |
| | Sequences homologous to monkey β$_1$-AR mRNA |
| SEO ID NO:26 | 5'-GGGCGCTCGTCCTGGGCGCCTCCGA6CCC6GTAAC-3' |
| SEQ ID ND:27 | 5'-ATGGGCGCGGGGGCGCTCGTCCTGGGCGCCTCCGA-3' |
| SEQ ID ND:28 | 5#-GCAACTCGGCATGGGCGCGGGG6CGCTCGTCCTGG-3' |

N means any nucleotide, e.g., C, A, U (T), or G.

Sequences in bold correspond to portions of the β$_1$-AR open reading frame.

In addition to the indicated 35-mers, smaller internal n-mers that comprise from at least 9 bases in length up to the full length 35-mers listed are also contemplated to be useful in the practice of the present invention. For example, in addition to the first indicated full-length oligomer, all internal n-mers are also considered to fall within the scope of this disclosure. Thus for each of the 35-mers (SEQ ID NO:4 to SEQ ID NO:28) all internal 34-mers of each sequence as well as all internal 33-mers, 32-mers, 31-mers, 30-mers, 29-mers, 28-mers, 27-mers, 26-mers, 25-mers, 24-mers, 23-mers, 22-mers, 21-mers, 20-mers, 19-mers, 18-mers, 17-mers, 16-mers, 15-mers, 14-mers, 13-mers, 12-mers, 11-mers, 10-mers, and 9-mers, that are comprised within of each of the disclosed 35-mers are also contemplated to be useful in the practice of the present invention.

For illustrative purposes, all representative n-mers of SEQ ID NO:10 would include the following internal contiguous 9-mer to 34-mer sequences:

CAGCTCGGCATGGGCGCGGGGT-GCTCGTCCTGG (SEQ ID NO:29)

GCAGCTCGGCATGGGCGCGGGGT-GCTCGTCCTG (SEQ ID NO:30)

AGCTCGGCATGGGCGCGGGGTGCTCGTCCTGG (SEQ ID NO:31)

GCAGCTCGGCATGGGCGCGGGGTGCTCGTCCT (SEQ ID NO:32)

GCTCGGCATGGGCGCGGGGTGCTCGTCCTGG (SEQ ID NO:33)

GCAGCTCGGCATGGGCGCGGGGTGCTCGTCC (SEQ ID NO:34)

CTCGGCATGGGCGCGGGGTGCTCGTCCTGG (SEQ ID NO:35)

GCAGCTCGGCATGGGCGCGGGGTGCTCGTC (SEQ ID NO:36)

TCGGCATGGGCGCGGGGTGCTCGTCCTGG (SEQ ID NO:37)

GCAGCTCGGCATGGGCGCGGGGTGCTCGT (SEQ ID NO:38)

CGGCATGGGCGCGGGGTGCTCGTCCTGG (SEQ ID NO:39)

GCAGCTCGGCATGGGCGCGGGGTGCTCG (SEQ ID NO:40)

GGCATGGGCGCGGGGGTGCTCGTCCTGG (SEQ ID NO:41)

GCAGCTCGGCATGGGCGCGGGGGTGCTC (SEQ ID NO:42)

GCATGGGCGCGGGGGTGCTCGTCCTGG (SEQ ID NO:43)

GCAGCTCGGCATGGGCGCGGGGGTGCT (SEQ ID NO:44)

CATGGGCGCGGGGGTGCTCGTCCTGG (SEQ ID NO:45)

GCAGCTCGGCATGGGCGCGGGGGTGC (SEQ ID NO:46)

ATGGGCGCGGGGGTGCTCGTCCTGG (SEQ ID NO:47)

GCAGCTCGGCATGGGCGCGGGGGTG (SEQ ID NO:48)

TGGGCGCGGGGGTGCTCGTCCTGG (SEQ ID NO:49)

GCAGCTCGGCATGGGCGCGGGGGT (SEQ ID NO:50)

GGGCGCGGGGGTGCTCGTCCTGG (SEQ ID NO:51)

GCAGCTCGGCATGGGCGCGGGG (SEQ ID NO:52)

GGCGCGGGGGTGCTCGTCCTGG (SEQ ID NO:53)

GCAGCTCGGCATGGGCGCGGGG (SEQ ID NO:54)

GCGCGGGGGTGCTCGTCCTGG (SEQ ID NO:55)

GCAGCTCGGCATGGGCGCGGG (SEQ ID NO:56)

CGCGGGGGTGCTCGTCCTGG (SEQ ID NO:57)

GCAGCTCGGCATGGGCGCGG (SEQ ID NO:58)

GCGGGGGTGCTCGTCCTGG (SEQ ID NO:59)

GCAGCTCGGCATGGGCGCG (SEQ ID NO:60)

CGGGGGTGCTCGTCCTGG (SEQ ID NO:61)

GCAGCTCGGCATGGGCGC (SEQ ID NO:62)

GGGGGTGCTCGTCCTGG (SEQ ID NO:63)

GCAGCTCGGCATGGGCG (SEQ ID NO:64)

GGGGTGCTCGTCCTGG (SEQ ID NO:65)

GCAGCTCGGCATGGGC (SEQ ID NO:66)

GGGTGCTCGTCCTGG (SEQ ID NO:67)

GCAGCTCGGCATGGG (SEQ ID NO:68)

GGTGCTCGTCCTGG (SEQ ID NO:69)

GCAGCTCGGCATGG (SEQ ID NO:70)

GGTGCTCGTCCTGG (SEQ ID NO:71)

GCAGCTCGGCATG (SEQ ID NO:72)
GTGCTCGTCCTGG (SEQ ID NO:73
GCAGCTCGGCAT (SEQ ID NO:74)
TGCTCGTCCTGG (SEQ ID NO:75)
GCAGCTCGGCA (SEQ ID NO:76)
GCTCGTCCTGG (SEQ ID NO:77)
GCAGCTCGGC (SEQ ID NO:78)
CTCGTCCTGG (SEQ ID NO:79)
GCAGCTCGG (SEQ ID NO:80), Etc.

In similar fashion, for illustrative purposes, and in the sake of brevity, representative n-mers of SEQ ID NO:1 would include the following internal contiguous sequences:
CGCGCCCATGCCGA (SEQ ID NO:81);
CCGCGCCCATGCCG (SEQ ID NO:82);
GCGCCCATGCCGA (SEQ ID NO:83);
CCGCGCCCATGCC (SEQ ID NO:84);
CGCCCATGCCGA (SEQ ID NO:85);
CCGCGCCCATGC (SEQ ID NO:86);
GCCCATGCCGA (SEQ ID NO:87);
CCGCGCCCATG (SEQ ID NO:88);
CCCATGCCGA (SEQ ID NO:89);
CCGCGCCCAT (SEQ ID NO:90);
CCATGCCGA (SEQ ID NO:91); and
CCGCGCCCA (SEQ ID NO:92).

Given the benefit of the present disclosure, the skilled artisan would also be able now, in similar fashion, to prepare any and all possible n-mers from each of the disclosed sequences, and from these sequences, identify and select those particular oligonucleotide sequences that specifically inhibit $\beta_1$-AR-specific mRNA expression for therapeutic use by using an acceptable in vitro and/or in vivo assay, such as those described hereinbelow.

Likewise, based upon the sequence of the human $\beta_1$-AR gene, the inventors have identified highly preferred sequences of from about 15 to about 25 nucleotides in length that specifically bind to the mRNA encoding $\beta_1$-AR polypeptide, and that reduce the level of polypeptide in a cell expressing such an mRNA. Illustrative sequences in this size range are identified below:

Length=15 nucleotides:
5'-CACCCCCGCGCCCAT-3' (SEQ ID NO:93)
5'-ACCCCCGCGCCCATG-3' (SEQ ID NO:94)
5'-CGCGCCCATGCCGAG-3' (SEQ ID NO:95)
5'-GCGCCCATGCCGAGC-3' (SEQ ID NO:96)
5'-CGCCCATGCCGAGCT-3' (SEQ ID NO:97)
5'-GCCCATGCCGAGCTG-3' (SEQ ID NO:98)
5'-CCCATGCCGAGCTGC-3' (SEQ ID NO:99)
5'-CCATGCCGAGCTGCG-3' (SEQ ID NO:100)
5'-CATGCCGAGCTGCGG-3' (SEQ ID NO:101)
5'-ATGCCGAGCTGCGGA-3' (SEQ ID NO:102)

Length=16 nucleotides:
5'-GCGCCCATGCCGAGCT-3' (SEQ ID NO:103)
5'-CGCCCATGCCGAGCTG-3' (SEQ ID NO:104)
5'-GCCCATGCCGAGCTGC-3' (SEQ ID NO:105)
5'-CCCATGCCGAGCTGCG-3' (SEQ ID NO:106)
5'-CCATGCCGAGCTGCGG-3' (SEQ ID NO:107)
5'-CATGCCGAGCTGCGGA-3' (SEQ ID NO:108)
5'-ATGCCGAGCTGCGGAG-3' (SEQ ID NO:109)
5'-TGCCGAGCTGCGGAGG-3' (SEQ ID NO:110)

Length=17 nucleotides:
5'-CGCGCCCATGCCGAGCT-3' (SEQ ID NO:111)
5'-GCGCCCATGCCGAGCTG-3' (SEQ ID NO:112)
5'-CGCCCATGCCGAGCTGC-3' (SEQ ID NO:113)
5'-GCCCATGCCGAGCTGCG-3' (SEQ ID NO:114)
5'-CCCATGCCGAGCTGCGG-3' (SEQ ID NO:115)
5'-CCATGCCGAGCTGCGGA-3' (SEQ ID NO:116)
5'-CATGCCGAGCTGCGGAG-3' (SEQ ID NO:117)
5'-ATGCCGAGCTGCGGAGG-3' (SEQ ID NO:118)

Length=18 nucleotides:
5'-CCGCGCCCATGCCGAGCT-3' (SEQ ID NO:119)
5'-CGCGCCCATGCCGAGCTG-3' (SEQ ID NO:120)
5'-GCGCCCATGCCGAGCTGC-3' (SEQ ID NO:121)
5'-CGCCCATGCCGAGCTGCG-3' (SEQ ID NO:122)
5'-GCCCATGCCGAGCTGCGG-3' (SEQ ID NO:123)
5'-CCCATGCCGAGCTGCGGA-3' (SEQ ID NO:124)
5'-CCATGCCGAGCTGCGGAG-3' (SEQ ID NO:125)
5'-CATGCCGAGCTGCGGAGG-3' (SEQ ID NO:126)

Length=19 nucleotides:
5'-ACCCCCGCGCCCATGCCGA-3' (SEQ ID NO:127)
5'-CCCGCGCCCATGCCGAGCT-3' (SEQ ID NO:128)
5'-CCGCGCCCATGCCGAGCTG-3' (SEQ ID NO:129)
5'-CGCGCCCATGCCGAGCTGC-3' (SEQ ID NO:130)
5'-GCGCCCATGCCGAGCTGCG-3' (SEQ ID NO:131)
5'-CGCCCATGCCGAGCTGCGG-3' (SEQ ID NO:132)
5'-GCCCATGCCGAGCTGCGGA-3' (SEQ ID NO:133)
5'-CCCATGCCGAGCTGCGGAG-3' (SEQ ID NO:134)
5'-CCATGCCGAGCTGCGGAGG-3' (SEQ ID NO:135)

Length=20 nucleotides:
5'-CACCCCCGCGCCCATGCCGA-3' (SEQ ID NO:136)
5'-ACCCCCGCGCCCATGCCGAG-3' (SEQ ID NO:137)
5'-CCCCCGCGCCCATGCCGAGC-3' (SEQ ID NO:138)
5'-CCCCGCGCCCATGCCGAGCT-3' (SEQ ID NO:139)
5'-CCCGCGCCCATGCCGAGCTG-3' (SEQ ID NO:140)
5'-CCGCGCCCATGCCGAGCTGC-3' (SEQ ID NO:141)
5'-CGCGCCCATGCCGAGCTGCG-3' (SEQ ID NO:142)
5'-GCGCCCATGCCGAGCTGCGG-3' (SEQ ID NO:143)
5'-CGCCCATGCCGAGCTGCGGA-3' (SEQ ID NO:144)
5'-GCCCATGCCGAGCTGCGGAG-3' (SEQ ID NO:145)
5'-CCCATGCCGAGCTGCGGAGG-3' (SEQ ID NO:146)

Length=21 nucleotides:
5'-CACCCCCGCGCCCATGCCGAG-3' (SEQ ID NO:147)
5'-ACCCCCGCGCCCATGCCGAGC-3' (SEQ ID NO:148)
5'-CCCCCGCGCCCATGCCGAGCT-3' (SEQ ID NO:149)
5'-CCCCGCGCCCATGCCGAGCTG-3' (SEQ ID NO:150)

5'-CCCGCGCCCATGCCGAGCTGC-3' (SEQ ID NO:151)
5'-CCGCGCCCATGCCGAGCTGCG-3' (SEQ ID NO:152)
5'-CGCGCCCATGCCGAGCTGCGG-3' (SEQ ID NO:153)
5'-GCGCCCATGCCGAGCTGCGGA-3' (SEQ ID NO:154)
5'-CGCCCATGCCGAGCTGCGGAG-3' (SEQ ID NO:155)
5'-GCCCATGCCGAGCTGCGGAGG-3' (SEQ ID NO:156)

Length=22 nucleotides:
5'-CACCCCCGCGCCCATGCCGAGC-3' (SEQ ID NO:157)
5'-ACCCCCGCGCCCATGCCGAGCT-3' (SEQ ID NO:158)
5'-CCCCCGCGCCCATGCCGAGCTG-3' (SEQ ID NO:159)
5'-CCCCGCGCCCATGCCGAGCTGC-3' (SEQ ID NO:160)
5'-CCCGCGCCCATGCCGAGCTGCG-3' (SEQ ID NO:161)
5'-CCGCGCCCATGCCGAGCTGCGG-3' (SEQ ID NO:162)
5'-CGCGCCCATGCCGAGCTGCGGA-3' (SEQ ID NO:163)
5'-GCGCCCATGCCGAGCTGCGGAG-3' (SEQ ID NO:164)
5'-CGCCCATGCCGAGCTGCGGAGG-3' (SEQ ID NO:165)

Length=23 nucleotides:
5'-CACCCCCGCGCCCATGCCGAGCT-3' (SEQ ID NO:166)
5'-ACCCCCGCGCCCATGCCGAGCTG-3' (SEQ ID NO:167)
5'-CCCCCGCGCCCATGCCGAGCTGC-3' (SEQ ID NO:168)
5'-CCCCGCGCCCATGCCGAGCTGCG-3' (SEQ ID NO:169)
5'-CCCGCGCCCATGCCGAGCTGCGG-3' (SEQ ID NO:170)
5'-CCGCGCCCATGCCGAGCTGCGGA-3' (SEQ ID NO:171)
5'-CGCGCCCATGCCGAGCTGCGGAG-3' (SEQ ID NO:172)
5'-GCGCCCATGCCGAGCTGCGGAGG-3' (SEQ ID NO:173)

Length=24 nucleotides:
5'-CACCCCCGCGCCCATGCCGAGCTG-3' (SEQ ID NO:174)
5'-ACCCCCGCGCCCATGCCGAGCTGC-3' (SEQ ID NO:175)
5'-CCCCCGCGCCCATGCCGAGCTGCG-3' (SEQ ID NO:176)
5'-CCCCGCGCCCATGCCGAGCTGCGG-3' (SEQ ID NO:177)
5'-CCCGCGCCCATGCCGAGCTGCGGA-3' (SEQ ID NO:178)
5'-CCGCGCCCATGCCGAGCTGCGGAG-3' (SEQ ID NO:179)
5'-CGCGCCCATGCCGAGCTGCGGAGG-3' (SEQ ID NO:180)

Length=25 nucleotides:
5'-CACCCCCGCGCCATGCCGAGCTGC-3' (SEQ ID NO:181)
5'-ACCCCCGCGCCCATGCCGAGCTGCG-3' (SEQ ID NO:182)
5'-CCCCCGCGCCCATGCCGAGCTGCGG-3' (SEQ ID NO:183)
5'-CCCCGCGCCCATGCCGAGCTGCGGA-3' (SEQ ID NO:184)
5'-CCCGCGCCCATGCCGAGCTGCGGAG-3' (SEQ ID NO:185)
5'-CCGCGCCCATGCCGAGCTGCGGAGG-3' (SEQ ID NO:186)

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 2A shows the effect of $\beta_1$-AS-ODN on ISO-induced elevation in left ventricular pressure. Data represent mean±SEM of each group (n=6 to 9). *P<0.05, **P<0.01 vs. inverted ODN.

FIG. 2B shows the effect of $\beta_1$-AS-ODN on ISO-induced elevation in HR.

Figure 3A:
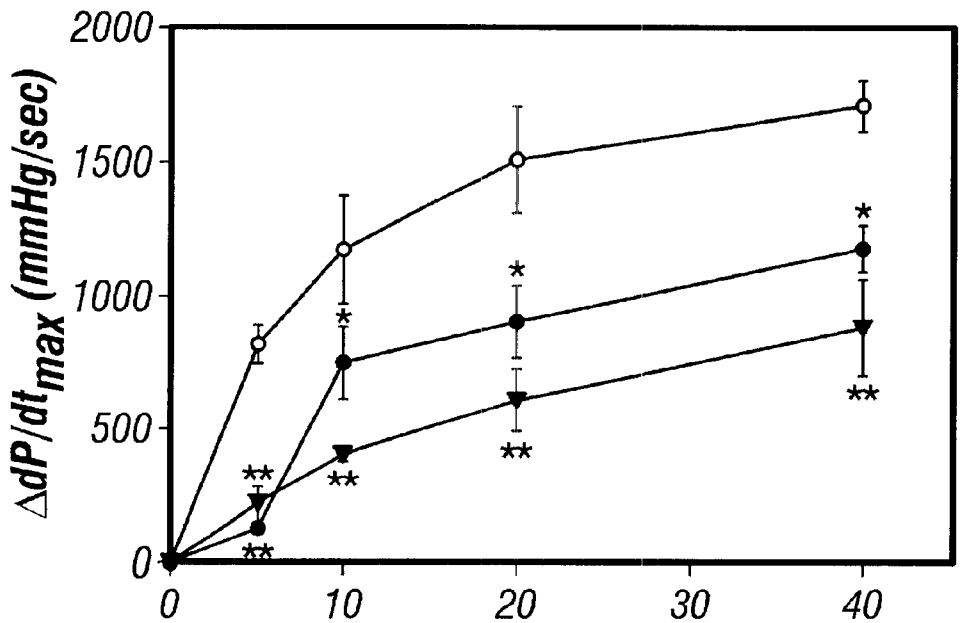
Figure 3B:
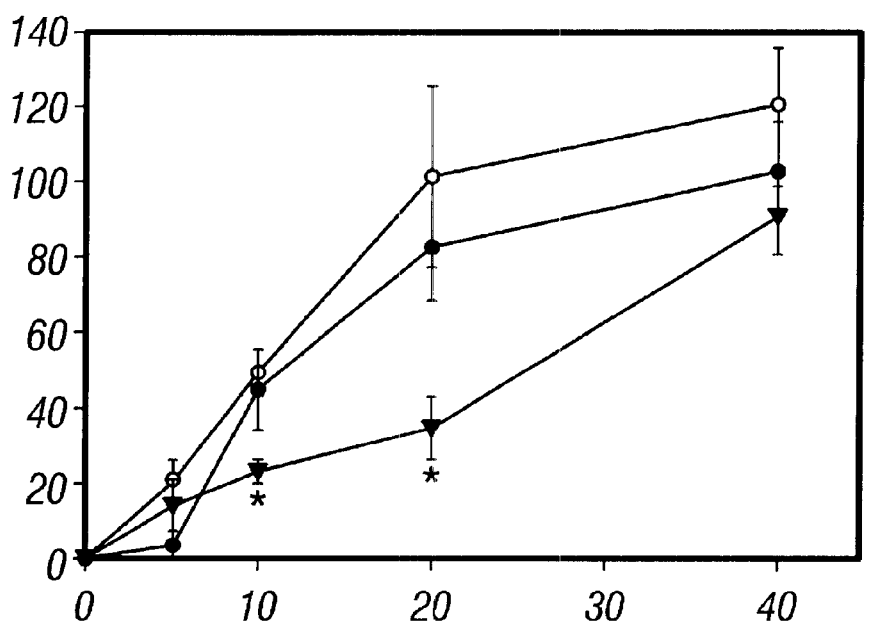
Figure 3C:
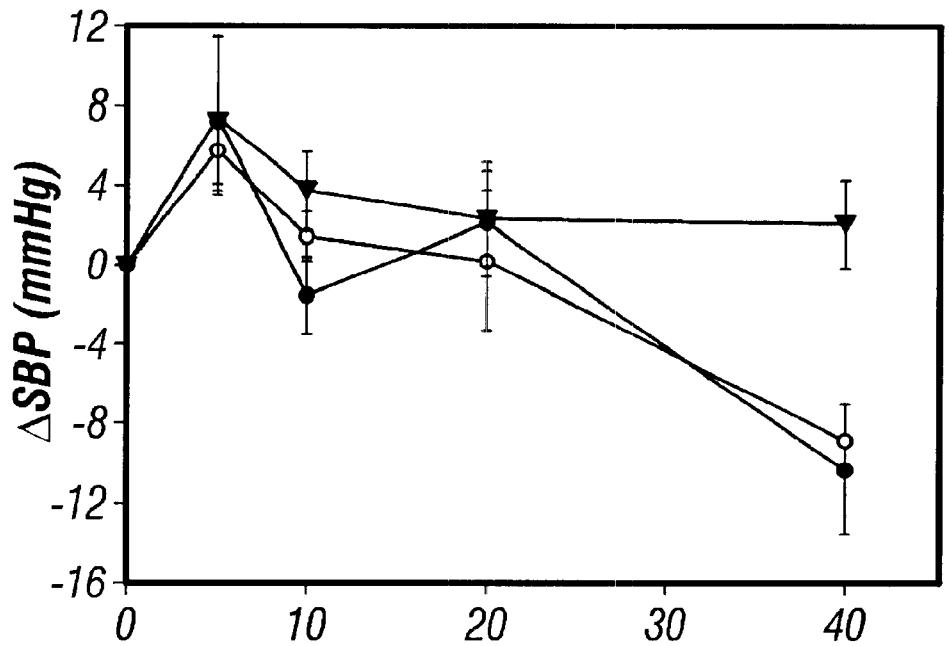

FIG. 3A, FIG. 3B and FIG. 3C show in vivo effects of $\beta_1$-AS-ODN and atenolol on cardiovascular hemodynamics of SHRs in response to $\beta_1$-stimulation. Same group of SHRs (n=4) was tested for dobutamine-induced hemodynamic alteration at control levels (○), and 1 hr. after atenolol injection (▲). Rats were allowed to fully recover between treatments. During dobutamine infusion, FIG. 3A shows cardiac $dP/dt_{max}$ of SHRs as monitored by the telemetry system. Data represent mean±SEM. *P<0.01 vs. control.

FIG. 3B shows HR of SHRs as monitored by telemetry system. Data represent mean±SEM. *P<0.01 vs. control.

FIG. 3C shows SBP of SHRs as monitored by telemetry system. Data represent mean±SEM. *P<0.01 vs. control.

Figure 4:
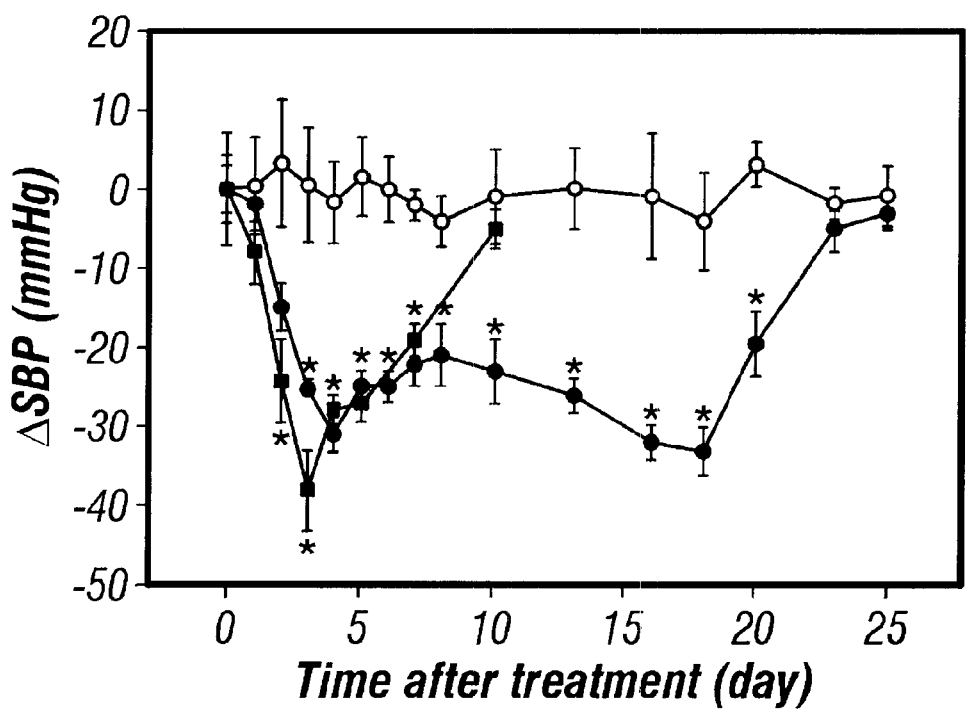

FIG. 4 shows the effect of $\beta_1$-AS-ODN on SBP of SHRs measured with tail cuff. A single dose of 1 mg/kg $\beta_1$-AS-ODN was injected into tongue vein with cationic liposome at molar ratio of 1:05 (■) or 1:2.5 (●). Inverted ODN (1 mg/kg) delivered with liposomes at molar ratio of 1:2.5 (○) served as control. Data represent mean±SEM of each group (n=6). *P<0.05 vs. inverted ODN.

Figure 5A:
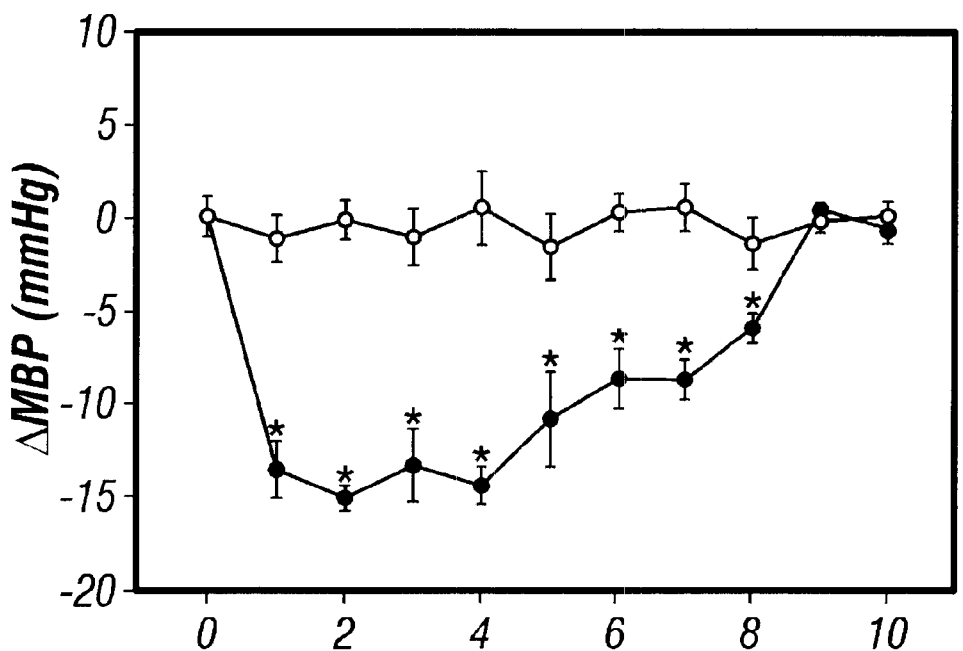

FIG. 5A shows the effect of $\beta_1$-AS-ODN on mean BP of SHRs monitored by telemetry. Dose of 1 mg/kg inverted ODN (○) or β$_1$-AS-ODN (●) was injected with liposomes at molar ratio of 1:05. BP and HR were recorded every 10 min. and averaged every 24 hr. Data represent mean±SEM of each group (n=6). *P<0.05 vs. inverted ODN.

Figure 5B:
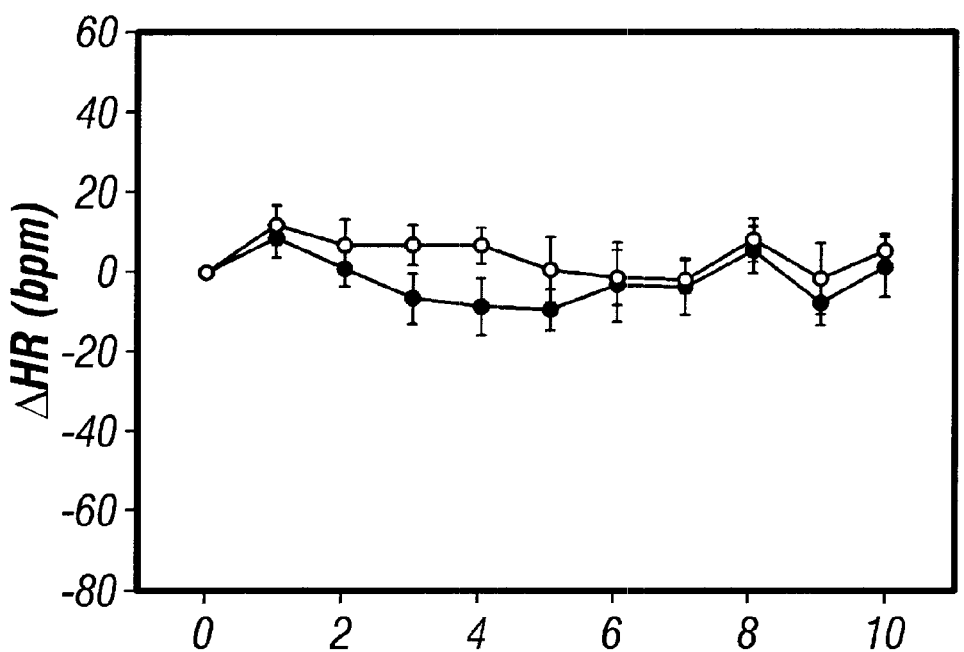

FIG. 5B show the effect of β$_1$-AS-ODN on mean HR of SHRs monitored by telemetry. Dose of 1 mg/kg inverted ODN (○) or β$_1$-AS-ODN (●) was injected with liposomes at molar ratio of 1:05. BP and HR were recorded every 10 min. and averaged every 24 hr. Data represent mean±SEM of each group (n=6). *P<0.05 vs. inverted ODN.

Figure 6A:
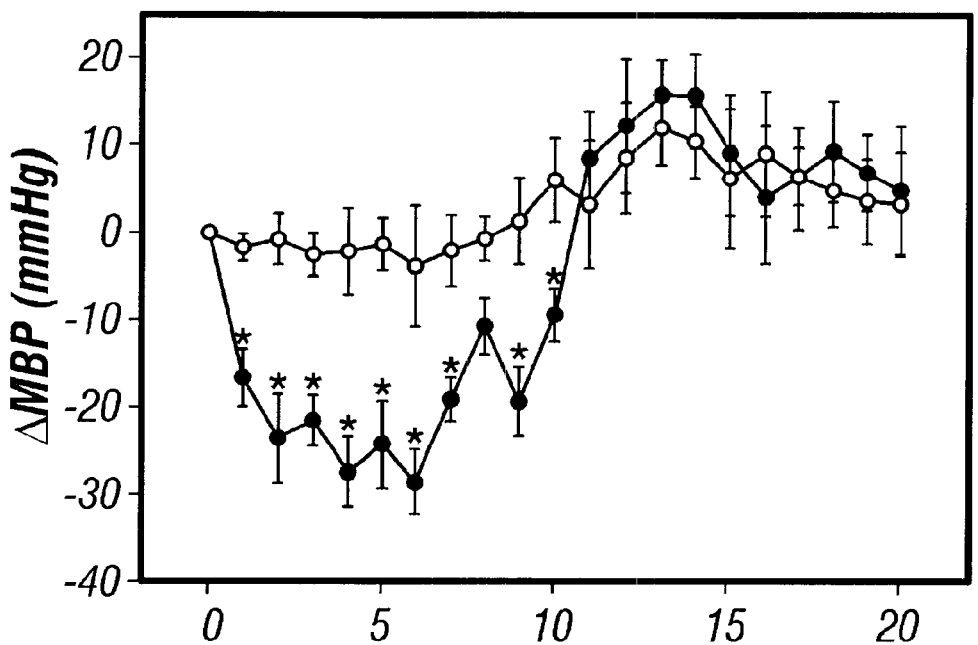

FIG. 6A shows the effect of atenolol on mean BP of SHRs monitored by telemetry. Saline (○) or 1 mg/kg atenolol (●) was injected intravenously. BP and HR were taken every 10 min. and averaged every 1 hr. Data represent mean±SEM of each group (n=6). *P<0.05 vs. saline.

Figure 6B:
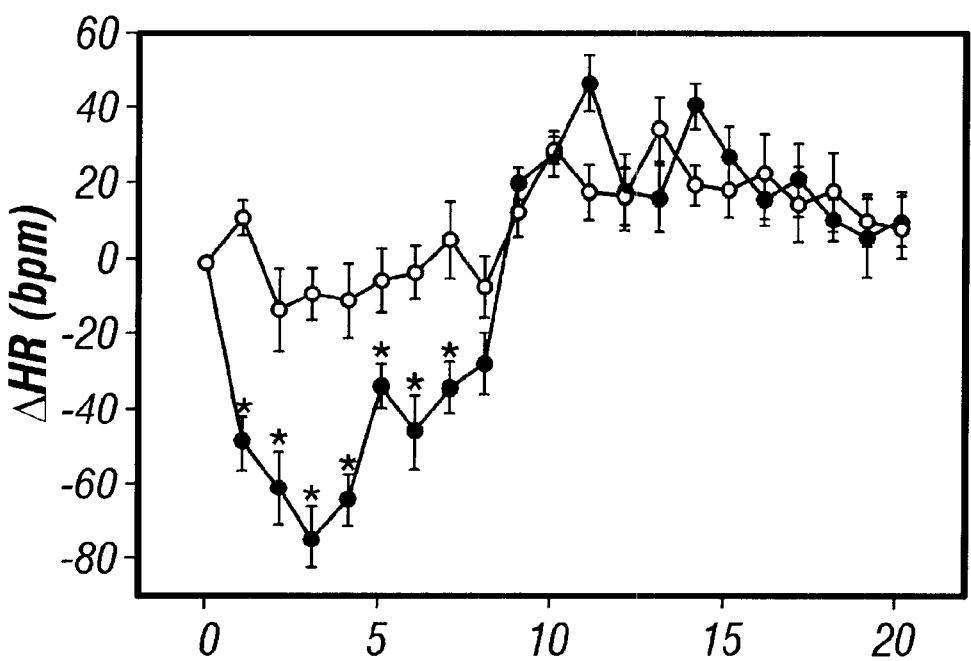

FIG. 6B shows the effect of atenolol on mean HR of SHRs monitored by telemetry. Saline (○) or 1 mg/kg atenolol (●) was injected intravenously. BP and HR were taken every 10 min. and averaged every 1 hr. Data represent mean±SEM of each group (n=6). *P<0.05 vs. saline.

Figure 7:
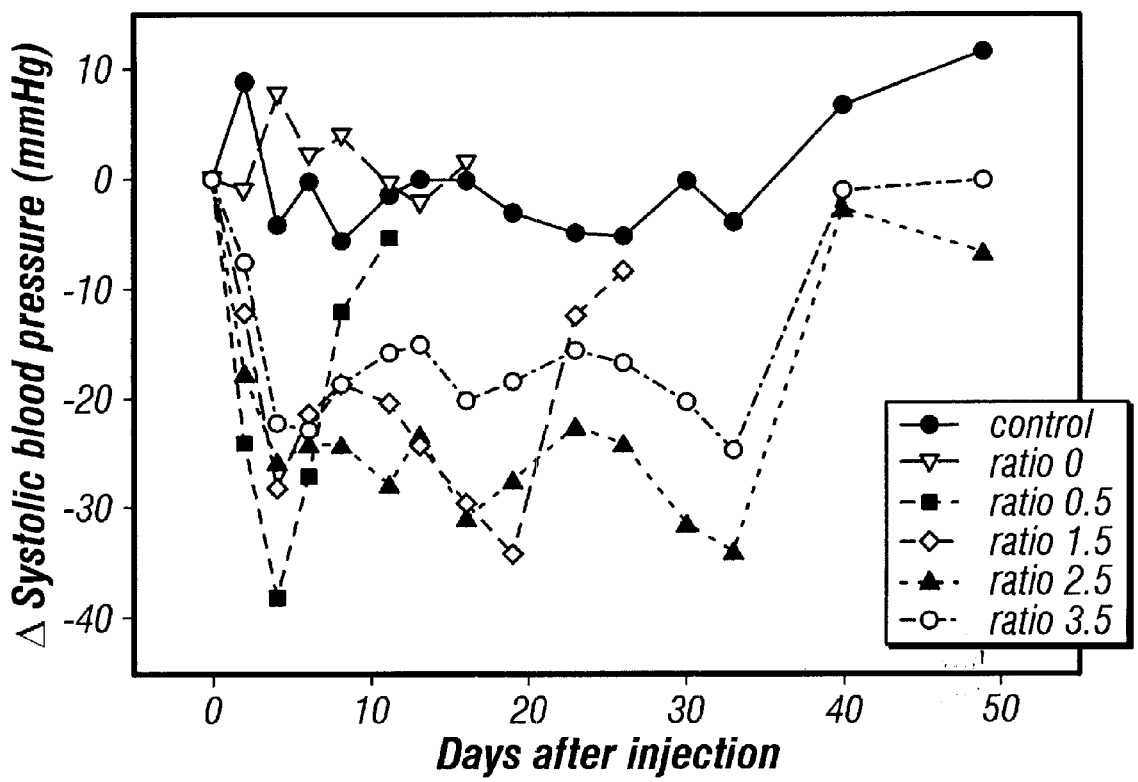

FIG. 7 shows improving the antihypertensive effect of β$_1$-AS-ODN by optimization of liposome:ODN charge ratios. SHR received a single intravenous injection of β$_1$-AS-ODN or inverted ODN. β$_1$-AS-ODN 0.5 mg/kg was delivered by DOTAP/DOPE at charge ratios from 0 to 3.5. Inverted ODN 0.5 mg/kg delivered by DOTAP/DOPE at charge ratio 2.0 served as control. Data represent mean values of each group (n=6). Standard errors were omitted for clarity.

Figure 8A:
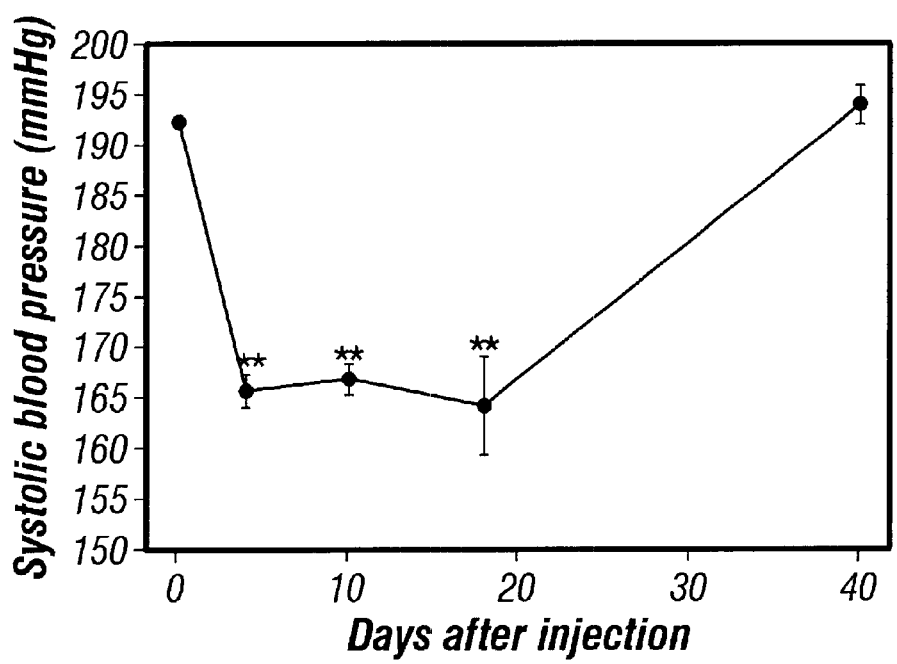
Figure 8B:
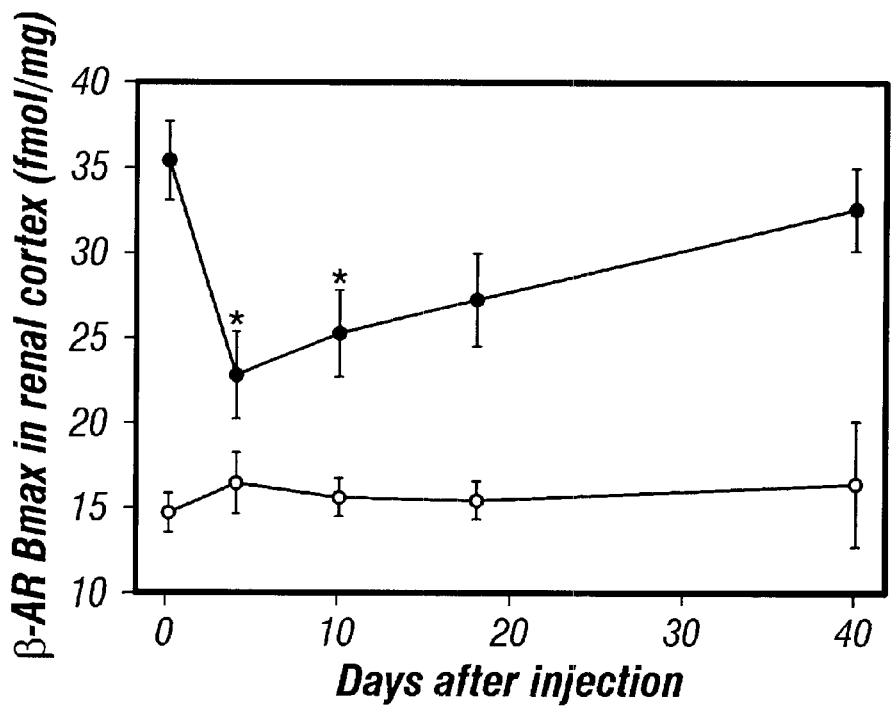
Figure 8C:
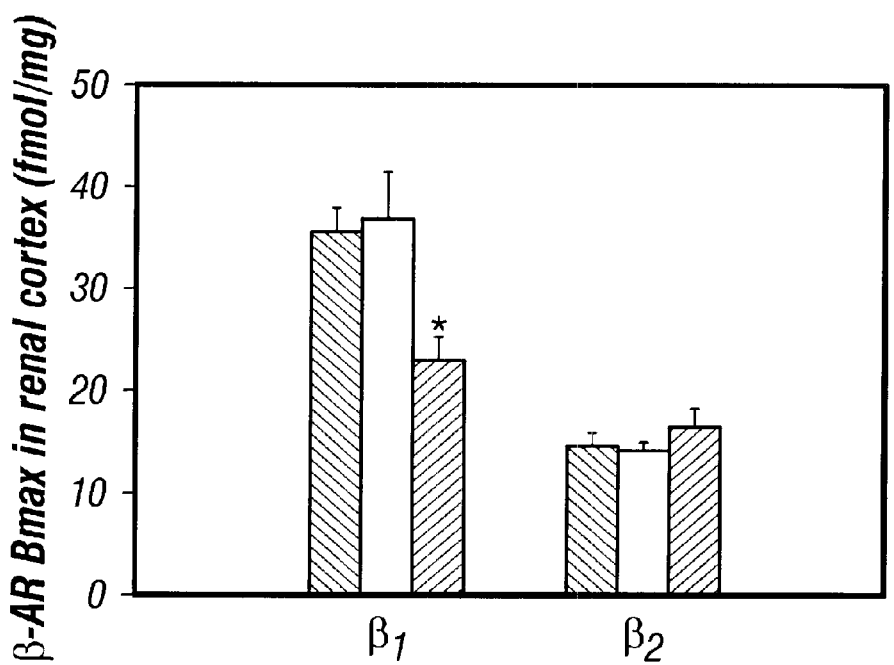

FIG. 8A, FIG. 8B and FIG. 8C show the effects of β$_1$-AS-ODN on blood pressure and β-AR levels in renal cortex. SHR were injected with 0.5 mg/kg β$_1$-AS-ODN or inverted ODN with liposomes at charge ratio 2.

FIG. 8A shows the effect on blood pressure.

FIG. 8B shows the time course of the changes in B$_{max}$ of β$_1$-AR (●) and β$_2$-AR (○).

FIG. 8C shows the B$_{max}$ of β-AR 4 days after intravenous injection of saline (solid bar), inverted ODN (open bar), or β$_1$-AS-ODN (shaded bar). Data represent mean±SEM of each point (n=6). *P<0.101 vs. saline control.

Figure 9A:
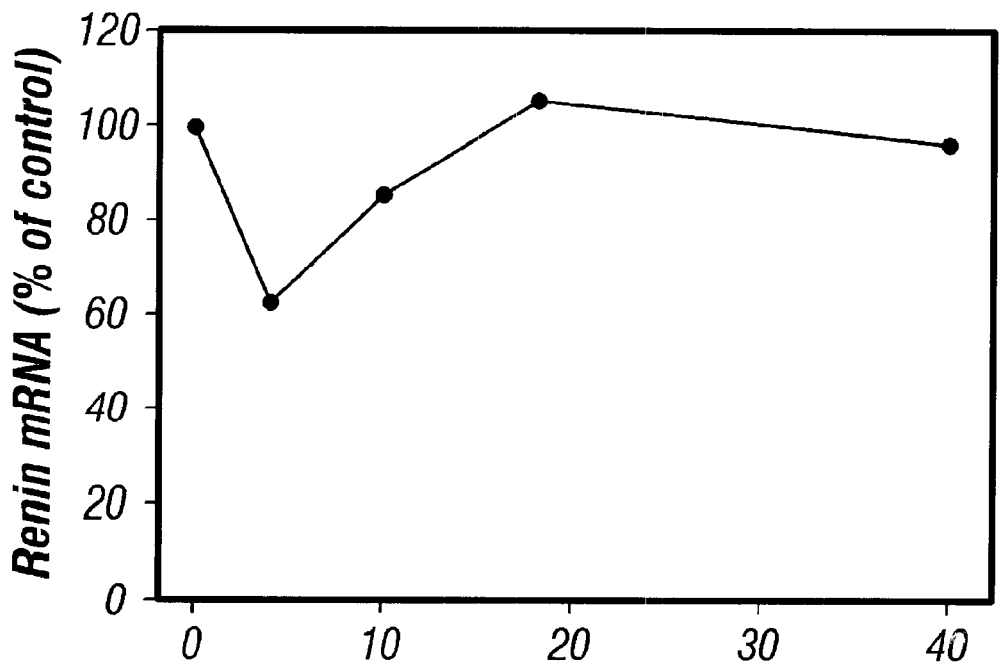
Figure 9B:
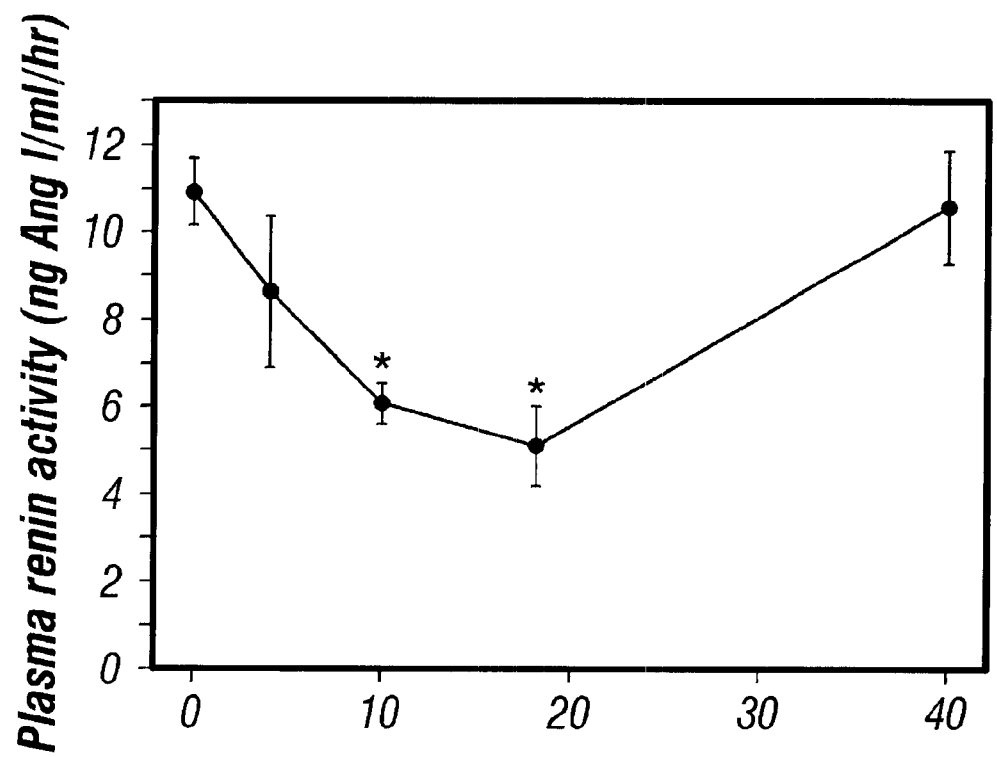
Figure 9C:
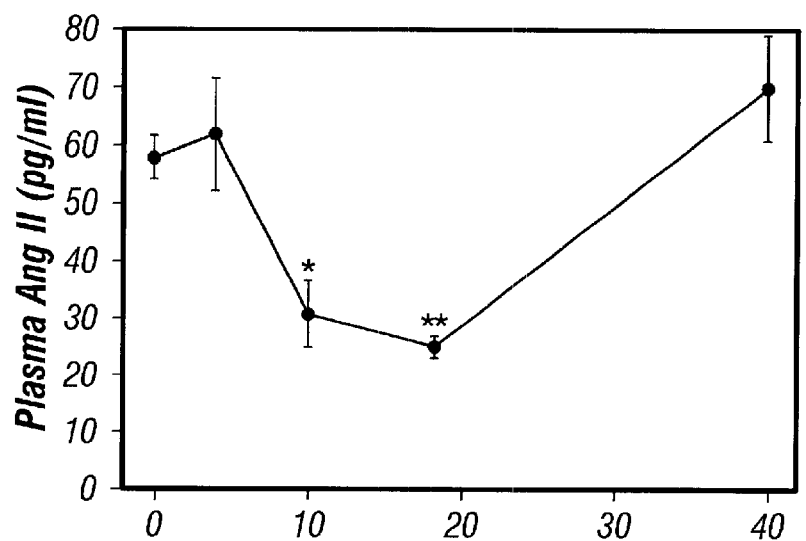

FIG. 9A, FIG. 9B and FIG. 9C show β$_1$-AS-ODN at a single injection exerts a delayed suppression on RAS.

FIG. 9A shows the effect on preprorenin mRNA levels in renal cortex.

FIG. 9B shows the effect on PRA.

FIG. 9C shows the effect on plasma Ang II levels. Data represent mean±SEM of each point (n=6). *P<0.01, **P<0.001 vs. control.

Figure 10:
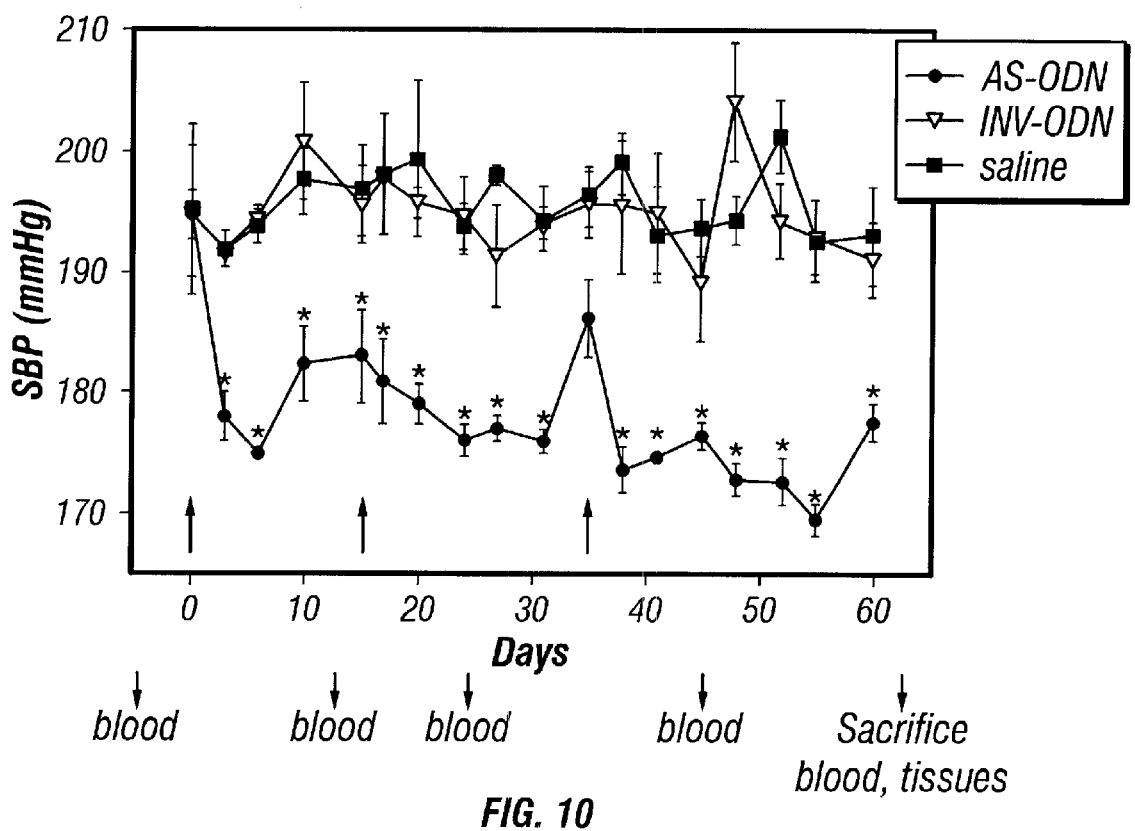

FIG. 10 illustrates sustained antihypertensive effects of repeated administrations of β$_1$-AS-ODN in SHR. Three repeated i.v. injections of 1 mg/kg β$_1$-AS-ODN (n=9) delivered by liposomes were given to adult SHR as indicated by upward arrows. Repeated injection of saline (n=7) and 1 mg/kg INV-ODN (n=7) served as controls. Systolic BP was measured by tail cuff method. Blood samples were collected at different time points as indicated by downward arrows for safety profile analysis. Data represent mean±SEM. P<0.05 vs. saline or INV-ODN.

Figure 11:
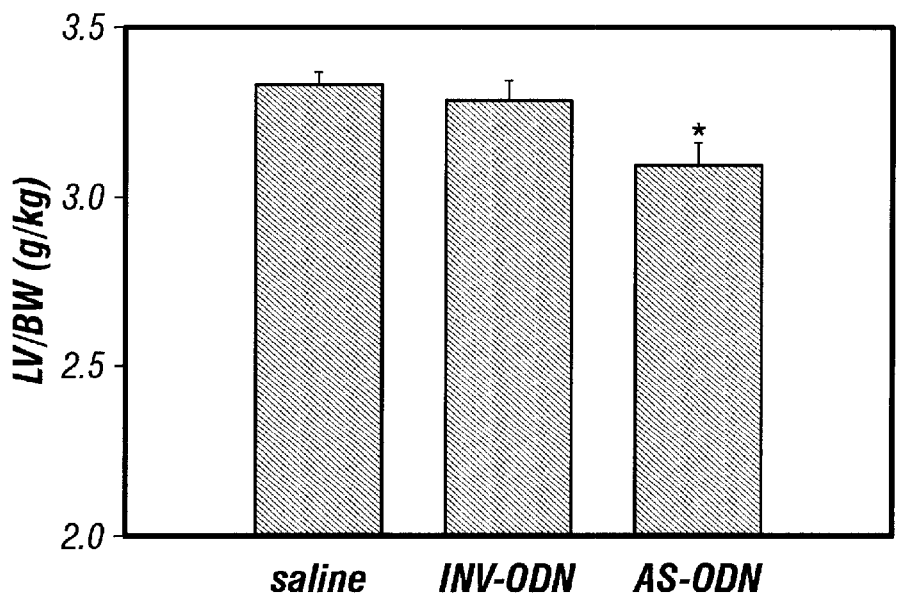

FIG. 11 illustrates repeated administration of β$_1$-AS-ODN causes reduced left ventricular hypertrophy in SHR. SHR were treated with repeated injections of β$_1$-AS-ODN (n=9), saline (n=7) or INV-ODN (n=7) for 2 months. *P<0.

Figure 12A:
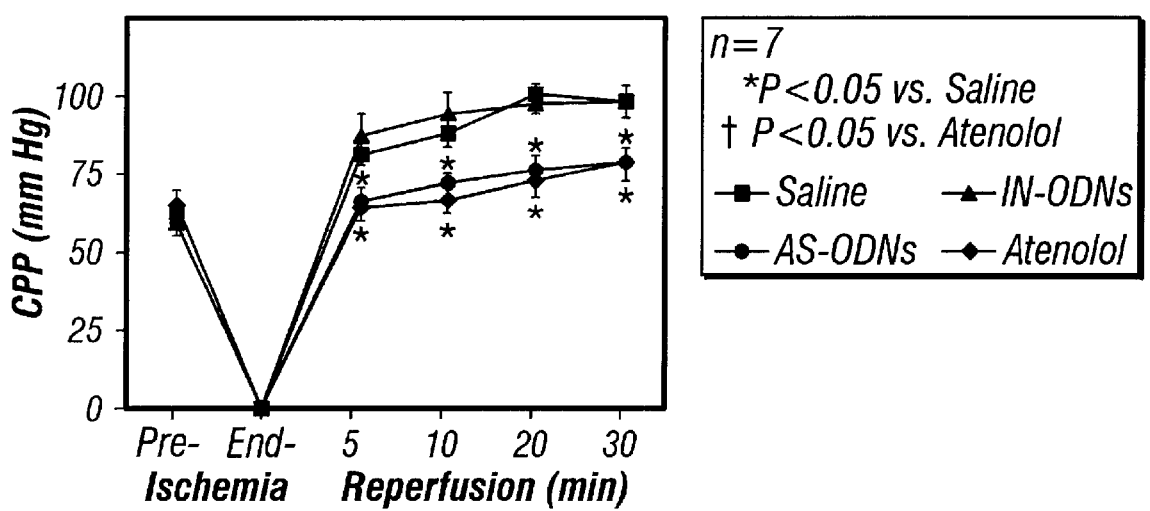
Figure 12B:
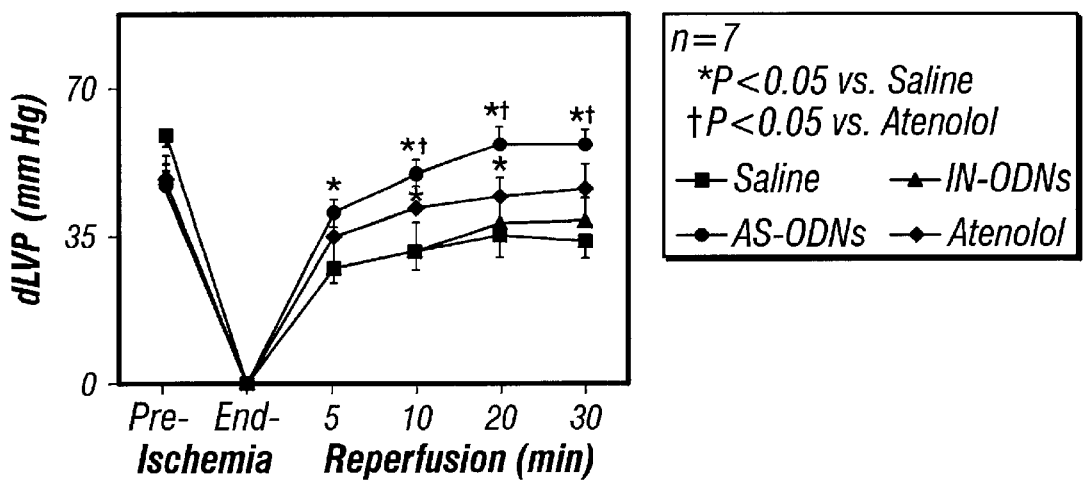
Figure 12C:
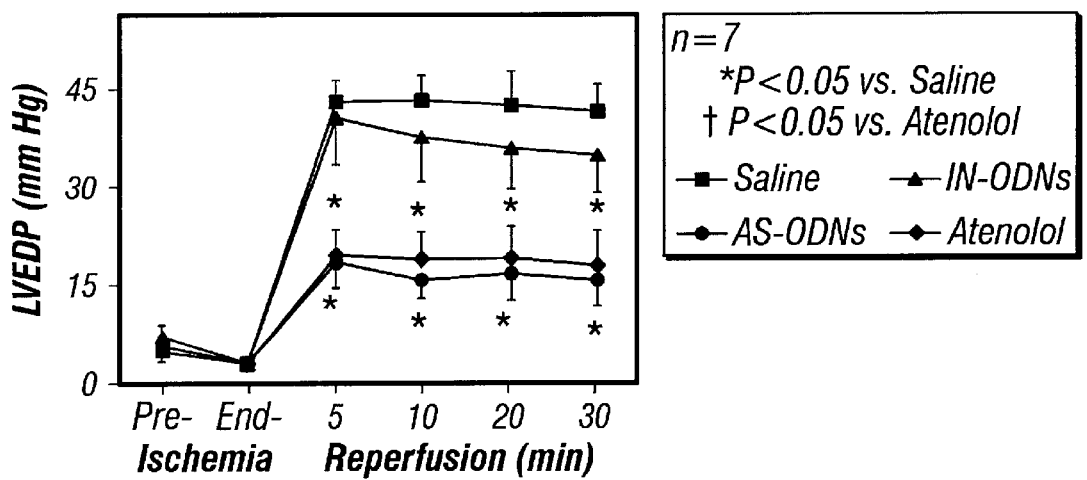

FIG. 12 illustrates β$_1$-AS-ODN and atenolol attenuated ischemia-reperfusion induced cardiac dysfunction. Note the marked increase in LVEDP and CPP and decrease in dLVP in saline-treated rat hearts exposed to a brief ischemia-reperfusion. β$_1$-AS-ODN, but not INV-ODN, exhibited beneficial effects on cardiac functions, indicated by a smaller increment in CPP and LVEDP and preservation dLVP. Atenolol showed a similar protective effect. Data represent mean±SEM of n=7 for each group.

Figure 13A:
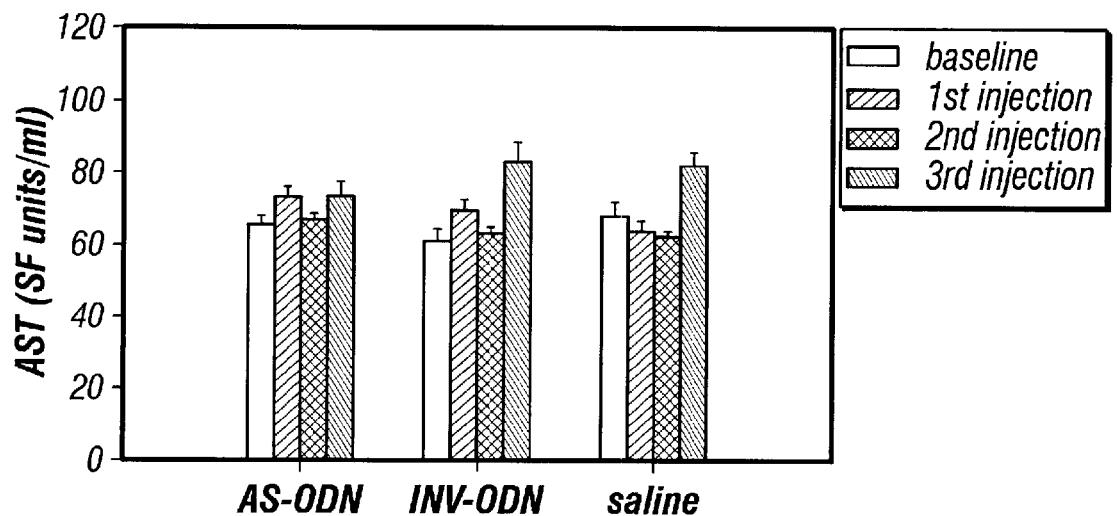
Figure 13B:
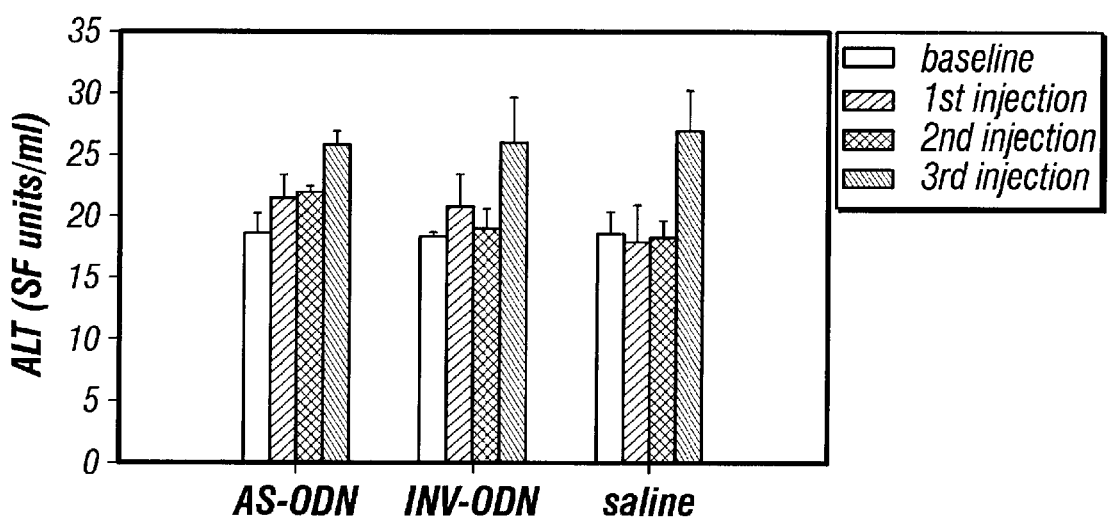

FIG. 13 illustrates plasma levels of liver transaminases ALT and AST after repeated injections of β$_1$-AS-ODN. Saline and INV-ODN serve as controls. Data represent mean±SEM of each group (n=7–9).

4.0 DESCRIPTION OF ILLUSTRATIVE EMBODIMENTS

4.1 Antisense Oligonucleotides

The utility of the disclosed compounds and compositions in inhibiting expression of mammalian β$_1$-AR-specific mRNA has been described and demonstrated both in vitro and in vivo by the methods described herein.

Preferred polynucleotide and oligonucleotide compounds of the present invention specifically bind to an mRNA encoding a mammalian β$_1$-AR polypeptide thereby inhibiting the translation of the mRNA, and concomitant expression of the encoded polypeptide.

Highly preferred antisense compounds and compositions are those that specifically bind to the mRNA encoding human β$_1$-AR polypeptide.

The mRNA sequence encoding the human β$_1$-AR polypeptide is disclosed in GenBank™ accession number NM000684, and described herein as SEQ ID NO:187. The mRNA sequence encoding canine β$_1$-AR polypeptide is disclosed in GenBank™ accession number U73207, and described herein as SEQ ID NO:188. The mRNA sequence encoding the sheep β$_1$-AR polypeptide is disclosed in GenBank™ accession numbers S78499 and AF072433, and described herein as SEQ ID NO:189. Likewise, porcine β$_1$-AR-encoding mRNA is disclosed in GenBank™ accession number AF042454, and described herein as SEQ ID NO:190. Rodent (Rattus) β$_1$-AR-encoding mRNA is disclosed in GenBank™ accession number D00634 and described herein as SEQ ID NO:191. Rhesus monkey β$_1$-AR-encoding mRNA is disclosed in GenBank™ accession number X75540, and described herein as SEQ ID NO:192. Murine (Mus) mouse β$_1$-AR-encoding mRNA is disclosed in GenBank™ accession number L10084, and described herein as SEQ ID NO:193. Highly homologous β$_1$-AR-encoding DNAs have also been identified in non-mammalian species, such as frog (SEQ ID NO:194) disclosed in GenBank™ as accession number Y09213, further evidence to the fact that antisense oligonucleotides prepared complementary to a β$_1$-AR-encoding DNA from one species may be useful in reducing the expression of β$_1$-AR-specific mRNA in another species. In fact, the inventors contemplate that antisense oligonucleotides prepared complementary to highly conserved regions of the proximal portion of the β$_1$-AR mRNA may specifically bind to, and reduce translation of, the mRNA in a variety of host cells and animals that produce β$_1$-adrenoceptor polypeptides.

In the specification and claims, the letters, A, G, C, T, and U respectively indicate nucleotides in which the nucleoside is Adenosine (Ade), Guanosine (Gua), Cytidine (Cyt), Thymidine (Thy), and Uridine (Ura). As used in the specification and claims, compounds that are antisense to the β$_1$-adrenoceptor-specific PNA, DNA or mRNA sense strand are compounds that have a nucleoside sequence complementary to the sense strand. Table 2 shows the four possible sense strand nucleosides and their complements present in an antisense compound.

TABLE 2

| Sense | Antisense |
|---|---|
| Ade | Thy |
| Gua | Cyt |
| Cyt | Gua |
| Thy | Ade |
| Ura | Ade |

It will be understood by those skilled in the art that the present invention broadly includes oligonucleotide compounds that are capable of binding to the DNA or mRNA sense strand coding for $B_1R$. It will also be understood that mRNA includes not only the ribonucleotide sequences encoding a protein, but also regions including the 5'-untranslated region, the 3'-untranslated region, the 5'-cap region and the intron/exon junction regions.

The invention includes compounds which are not strictly antisense; the compounds of the invention also include those oligonucleotides that may have some bases that are not complementary to bases in the sense strand provided such compounds have sufficient binding affinity for $\beta_1$-adrenoceptor DNA or mRNA to inhibit expression. In addition, base modifications or the use of universal bases such as inosine in the oligonucleotides of the invention are contemplated within the scope of the subject invention.

The antisense compounds may have some or all of the phosphates in the nucleotides replaced by phosphorothioates (X=S) or methylphosphonates ($X=CH_3$) or other $C_{1-4}$ alkylphosphonates. The antisense compounds optionally may be further differentiated from native DNA by replacing one or both of the free hydroxy groups of the antisense molecule with $C_{1-4}$ alkoxy groups ($R=C_{1-4}$ alkoxy). As used herein, $C_{1-4}$ alkyl means a branched or unbranched hydrocarbon having 1 to 4 carbon-atoms.

The disclosed antisense compounds also may be substituted at the 3' and/or 5' ends by a substituted acridine derivative. As used herein, "substituted acridine," means any acridine derivative capable of intercalating nucleotide strands such as DNA. Preferred substituted acridines are 2-methoxy-6-chloro-9-pentylarninoacridine, N-(6-chloro-2-methoxyacridinyl)-O-methoxydiisopropylaminophosphinyl-3-aminopropanol, and N-(6-chloro-2-methoxyacridinyl)-O-methoxydiisopropylaminophosphinyl-5-aminopentanol. Other suitable acridine derivatives are readily apparent to persons skilled in the art. Additionally, as used herein "P(0)(0)-substituted acridine" means a phosphate covalently linked to a substitute acridine.

As used herein, the term "nucleotides" includes nucleotides in which the phosphate moiety is replaced by phosphorothioate or alkylphosphonate and the nucleotides may be substituted by substituted acridines.

In one embodiment, the antisense compounds of the invention differ from native DNA by the modification of the phosphodiester backbone to extend the life of the antisense ON. For example, the phosphates can be replaced by phosphorothioates. The ends of the molecule may also be optimally substituted by an acridine derivative that intercalates nucleotide strands of DNA. Intl. Pat. Appl. Publ. No. WO 98/13526 and U.S. Pat. No. 5,849,902 (each specifically incorporated herein by reference) describe a method of preparing three component chimeric antisense compositions, and discuss many of the currently available methodologies for synthesis of substituted oligonucleotides having improved antisense characteristics and/or half-life.

The reaction scheme involves $^1$H-tetrazole-catalyzed coupling of phosphoramidites to give phosphate intermediates that are subsequently reacted with sulfur in 2,6-lutidine to generate phosphate compounds. Oligonucleotide compounds are prepared by treating the phosphate compounds with thiophenoxide (1:2:2 thiophenol/triethylamine/tetrahydrofuran, room temperature, 1 hr). The reaction sequence is repeated until an oligonucleotide compound of the desired length has been prepared. The compounds are cleaved from the support by treating with ammonium hydroxide at room temperature for 1 hr and then are further deprotected by heating at about 50° C. overnight to yield preferred antisense compounds.

The pharmaceutical preparations are made following conventional techniques of a pharmaceutical chemist involving mixing, granulating and compressing, when necessary, for tablet forms or mixing, filling, and dissolving the ingredients, as appropriate, to give the desired oral or parenteral products.

Doses of the present compounds (in a pharmaceutical dosage unit as described above) will be an efficacious, nontoxic quantity selected from the range of 1 ng/kg to 500 mg/kg of active compound, preferably less than 10 mg/kg. The selected dose is administered to a human patient in need of inhibition of $\beta_1$-AR-specific mRNA expression from 1–6 or more times daily, orally, rectally, by injection, or continuously by infusion. Oral formulations would generally require somewhat larger dosages to overcome the effects of gastric decomposition. Intravenous or intra-arterial administration would generally require lower doses since the drug is placed directly into the systemic circulation. Dosages for nasal sprays typically range from about 10 mg to about 50 mg (total) or about 0.1 mg/kg to about 10 mg/kg. Therefore, the dose will depend on the actual route of administration.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell. The results of these analyses are shown in Table 1, for illustrative oligonucleotides and selected target sequences identified in a variety of mammalian and non-mammalian sources.

Highly preferred target regions of the mRNA, are those that are at or near the AUG translation initiation codon, and those sequences that were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The sequences of the oligonucleotides given above are highly preferred sequences for inhibiting mammalian $\beta_1$-AR polypeptide activity in a host cell. Additional nucleotides at either end derived by the same process (using OLIGO and BLAST) are also envisioned by this invention. The effective lengths of the preferred oligonucleotides are preferably from at least 9 to about 35 or so nucleotides. The inventors contemplate all oligonucleotide compositions in this range (i.e., those of 9, 10, 11, 12, 13, 14, 15, 1,6, 17, 18, 19, 20, 21, 22, 23, 24, 25, 26, 27, 28, 29, 30, 31, 32, 33, 34, or 35 or so bases in length) are highly preferred for the practice of the oligonucleotide-based methods of the invention. In illustrative embodiments, the antisense compounds of the invention differ from native DNA by the modification of the phosphodiester backbone to extend the life of the antisense ODN, in which the phosphate substituents are replaced by phosphorothioates. Likewise, one or both ends of the oligonucleotide may be substituted by one or more acridine derivatives that intercalate between adjacent basepairs within a strand of nucleic acid.

4.2 Methods for Screening Patients at Risk for Hypertension

Because mammalian $\beta_1$-AR polypeptide plays a key role in hypertension in an animal, it is often desirable to measure and quantitate levels of $\beta_1$-AR polypeptide in an animal under a variety of conditions, even during the course of a treatment regimen designed to ameliorate the hypertensive condition in such an animal. Likewise, in many instances, it is desirable to employ methods for screening polymorphisms of the gene encoding mammalian $\beta_1$-AR, to identify patients "at risk" for hypertension, and to identify alleles of the gene both in vitro and in vivo.

As such, the use of one or more of the nucleotide compositions described herein as a probe for identifying a gene encoding mammalian $\beta_1$-AR, and methods for correlating the presence of such nucleotide segments with the risk of hypertension is particularly desirable.

4.3 Co-Administration of Small Molecule and Peptide Inhibitors

As described herein, in certain embodiments it may be desirable to co-administer one or more of the antisense compositions with one or more pharmaceuticals. For example, one or more of the commercially available antihypertensive agents may be co-administered in a particular therapeutic regimen. Such pharmaceuticals include, but are not limited to, amiloride, amlodipine, benazepril, bepridil, candesartan, captopril, chlorothiazide, chlorthalidone, dichlorphenamide, diltiazem, enalapril, ethacrynicacid, felodipine, fosinopril, furosemide, hydrochlorothiazide, hydroflumethiazide, irbesartan, isradipine, lisinopril, losartan, methylclothiazide, metolazone, misoldipine, moexipril, nicardipine, nifedepine, nimodipine, polythiazide, quinapril, ramipril, spironolactone, torsemide, trandolapril, triamterene, valsartan, and verapamil.

Additional small molecular weight ACE inhibitory compounds and oligopeptides, such as those described in U.S. Pat. No. 5,552,397; U.S. Pat. No. 5,449,661; U.S. Pat. No. 5,348,978; U.S. Pat. No. 5,238,921; U.S. Pat. No. 5,098,887 and U.S. Pat. No. 4,216,209 (each specifically incorporated herein by reference in its entirety). In certain embodiments, such small molecules or other anti-hypertensive agents may also be co-administered to an animal along with one or more of the disclosed antisense constructs.

The administration of such anti-hypertensive agents or small molecular weight inhibitors is well known to those of skill in the art, and particular, to health practitioners who routinely diagnose and/or treat animals or patients suffering from hypertension.

4.4 Pharmaceutical Compositions

Therefore, in certain embodiments, the present invention also concerns formulation of one or more of the antisense polynucleotide compositions disclosed herein in pharmaceutically acceptable solutions for administration to a cell or an animal, either alone, or in combination with one or more other modalities of antihypertensive therapy.

It will also be understood that, if desired, the nucleic acid segment, RNA, DNA or PNA antisense compositions disclosed herein may be administered in combination with other agents as well, such as, e.g., proteins or polypeptides or various pharmaceutically-active agents. As long as the composition comprises at least one $\beta_1$-AR-specific mRNA inhibitory antisense oligonucleotide, there is virtually no limit to other components that may also be included, given that the additional agents do not cause a significant adverse effect upon contact with the target cells or host tissues. The RNA, DNA, or PNA-derived antisense compositions may thus be delivered along with various other agents as required in the particular instance. Such RNA, DNA, or PNA antisense compositions may be purified from host cells or other biological sources, or alternatively may be chemically synthesized as described herein. Likewise, such compositions may comprise substituted or derivatized RNA, DNA, or PNA compositions. Such compositions may include modified peptide or nucleic acid substituent derivatives, as long as the base sequence of the RNA, DNA, or PNA molecule corresponds to one or more of the contiguous base sequences described herein that specifically bind to $\beta_1$-AR-specific mRNA, and that reduce or inhibit the extent of translation of this mRNA into biologically-active $\beta_1$-AR polypeptides.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

4.4.1 Injectable Delivery

Alternatively, the pharmaceutical compositions disclosed herein may be administered parenterally, intravenously, intramuscularly, or even intraperitoneally as described in U.S. Pat. No. 5,543,158, U.S. Pat. No. 5,641,515 and U.S. Pat. No. 5,399,363 (each specifically incorporated herein by reference in its entirety). Solutions of the active compounds as free-base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying. agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.4.2 Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the antisense compositions of the present invention into suitable host cells. In particular, the antisense oligonucleotide compositions of the present invention may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-lives (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567, 434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature, and results in an increase in permeability to ions, sugars, and drugs.

In addition to temperature, exposure to proteins can alter the permeability of liposomes. Certain soluble proteins such as cytochrome c bind deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

Alternatively, the invention provides for pharmaceutically acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145, 684, specifically incorporated herein by reference in its entirety). In particular, methods of antisense oligonucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.5 Therapeutic and Diagnostic Kits

The invention also encompasses one or more of the antisense compounds together with one or more pharmaceutically-acceptable excipients, carriers, diluents, adjuvants, and/or other components, such as additional antihypertensive agents, oligonucleotides, peptides, antigens, or other therapeutic compounds as may be employed in the formulation of particular oligonucleotide or polynucleotide delivery formulations, and in the preparation of antihypertensive agents or cardiac therapy for administration to an animal.

As such, preferred animals for administration of the pharmaceutical compositions disclosed herein include mammals, and particularly humans. Other preferred animals include primates, sheep, goats, bovines, equines, porcines, lupines, canines, and felines, as well as any other mammalian species commonly considered pets, livestock, or commercially relevant species. The composition may include partially or significantly purified antisense compositions, either alone, or in combination with one or more additional active ingredients, which may be obtained from natural or recombinant sources, or which may be obtainable naturally or either chemically synthesized, or alternatively produced in vitro from recombinant host cells expressing nucleic acid segments encoding such additional active ingredients.

Therapeutic kits may also be prepared that comprise at least one of the $\beta_1$-AR mRNA-specific antisense oligonucleotides and polynucleotides disclosed herein and instructions for using the composition as a therapeutic agent. The container means for such kits may typically comprise at least one vial, test tube, flask, bottle, syringe or other container means, into which the antisense composition(s) may be placed, and preferably suitably aliquoted. Where a second antihypertensive agent is also provided, the kit may also contain a second distinct container means into which this second composition may be placed. Alternatively, the plurality of antihypertensive compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

Alternatively, for the preparation of diagnostic kits, and for methods relating to the use of these compounds in the identification of $\beta_1$-AR polypeptide-encoding nucleic acids in a biological sample, such kits may be prepared that comprise at least one of the $\beta_1$-adrenoceptor mRNA-specific antisense oligonucleotides disclosed herein and instructions for using the composition as a probe for $\beta_1$-AR -specific nucleic acids in a hybridization assay. The container means for such kits may typically comprise at least one vial, test tube, microcentrifuge tube, or other container means, into which the antisense composition(s) may be placed and suitably aliquoted. Where a radiolabel or fluorigenic label or other such detecting means is included within the kit, the labeling agent may be provided either in the same container as the oligonucleotide composition, or may alternatively be placed in a second distinct container means into which this second composition may be placed and suitably aliquoted. Alternatively, the oligonucleotide composition and the label may be prepared in a single container means, and in most cases, the kit will also typically include a means for containing the vial(s) in close confinement for commercial sale and/or convenient packaging and delivery.

4.6 Peptide Nucleic Acid Compositions

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNAs may be utilized in a number of methods that traditionally have used RNA or DNA. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference. As such, in certain embodiments, one may prepare PNA sequences that are complementary to one or more portions of the $\beta_1$-adrenoceptor-specific mRNA sequence, and such PNA compositions may be used to regulate, alter, decrease, or reduce the translation of $\beta_1$-adrenoceptor-specific mRNA, and thereby alter the level of $\beta_1$-adrenoceptor polypeptide in a host cell to which such PNA compositions have been administered.

PNAs have 2-aminoethyl-glycine linkages replacing the normal phosphodiester backbone of DNA (Nielsen et al., 1993; Hanvey et al., 1992; Hyrup and Nielsen, 1996; Nielsen, 1995). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1992) or Fmoc (Bonham et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995).

4.7 Methods of Nucleic Acid Delivery and DNA Transfection

In certain embodiments, it is contemplated that one or more RNA, DNA, PNAs and/or substituted polynucleotide compositions disclosed herein will be used to transfect an appropriate host cell. Technology for introduction of PNAs, RNAs, and DNAs into cells is well known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takakura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

Moreover, the use of viral vectors (Lu et al., 1993; Eglitis and Anderson, 1988; Eglitis et al., 1988), including retroviruses, baculoviruses, adenoviruses, adenoassociated viruses, vaccinia viruses, Herpes viruses, and the like are well-known in the art, and are described in detail herein.

4.8 Expression Vectors

The present invention contemplates an expression vector comprising at least one $\beta_1$-AR -specific polynucleotide of the present invention. Thus, in one embodiment an expression vector is constructed with a specific DNA molecule orientated in the antisense direction. In another embodiment, a promoter is operatively linked to a sequence region that encodes a functional RNA such as a tRNA, a ribozyme or an antisense RNA.

As used herein, the term "operatively linked" means that a promoter is connected to a functional RNA in such a way that the transcription of that functional RNA is controlled and regulated by that promoter. Means for operatively linking a promoter to a functional RNA are well known in the art.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.9 In Vivo Delivery and Treatment Protocols

To introduce the antisense constructs to cells in vivo, one of any number of conventional ways may be employed. These methods include viral-mediated delivery using retroviral, adenoviral, or adeno-associated viral vectors, and are well known to those of skill in the antisense therapeutic arts.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

AAV (Ridgeway, 1988; Hermonat and Muzycska, 1984) is a parovirus, discovered as a contamination of adenoviral stocks. It is a ubiquitous virus (antibodies are present in 85% of the U.S. human population) that has not been linked to any disease. It is also classified as a dependovirus, because its replication is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

Figure 2A:
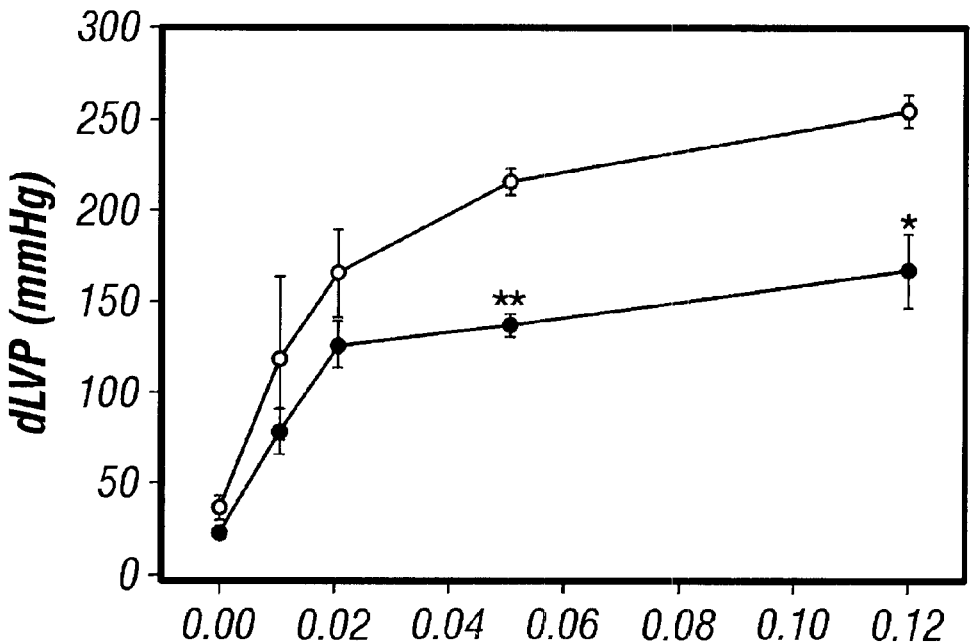
FIG. 2A and FIG. 2B show $\beta_1$-AS-ODN reduced ISO-stimulated positive inotropic more than chronotropic response in isolated perfused SHR hearts. 48 hr after intravenous injection of 1 mg/kg inverted ODN (○) or $\beta_1$-AS-ODN (●), hearts were perfused with Krebs buffer containing increasing concentrations of ISO.
Figure 2B:
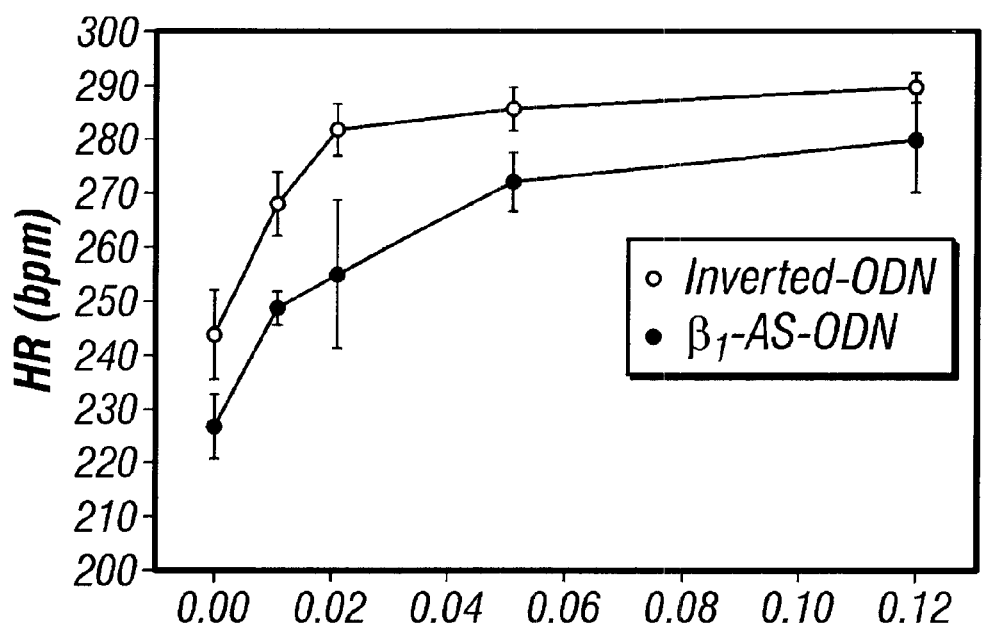

The AAV DNA is approximately 4.7 kilobases long. It contains two open reading frames and is flanked by two ITRs (FIGS. 2A, 2B and 2C). There are two major genes in the AAV genome: rep and cap. The rep gene encodes proteins responsible for viral replications, whereas the cap gene encodes the capsid protein VP1–3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

Other viral vectors may also be employed as expression constructs in the present invention for the delivery of $\beta_1$-AR mRNA-complementary oligonucleotide sequences to a host cell. Vectors derived from viruses such as vaccinia virus (Ridgeway, 1988; Coupar et al., 1988), lentiviruses, polioviruses and herpesviruses may be employed. They offer s several attractive features for various mammalian cells (Friedmann, 1989; Ridgeway, 1988; Coupar et al., 1988; Horwich et al., 1990).

In order to effect expression of the $\beta_1$-adrenoceptor mRNA-complementary antisense sequences of the present invention, the expression construct must be delivered into a cell. This delivery may be accomplished in vitro, as in laboratory procedures for transforming cells lines, or in vivo or ex vivo, as in the treatment of certain disease states, and in particular, in the treatment of hypertension and $\beta_1$-AR-related disorders. As described above, the preferred mechanism for delivery is via viral infection where the expression construct is encapsidated in an infectious viral particle.

Once the expression construct has been delivered into the cell the nucleic acid encoding the $\beta_1$-adrenoceptor mRNA-complementary oligonucleotide antisense sequences may be positioned and expressed at different sites. In certain embodiments, the nucleic acid encoding the antisense construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct comprising one or more $\beta_1$-AR mRNA-complementary oligonucleotide or polynucleotide antisense sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct comprising an $\beta_1$-AR mRNA-complementary oligonucleotide antisense sequence may be entrapped in one or more nanocapsules, liposomes, or other lipid based DNA delivery agent. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures, and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs that may be employed to deliver an antisense polynucleotide into a target cell include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP0273085, specifically incorporated herein by reference in its entirety).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Antisense Inhibition of $\beta_1$-AR mRNA $\beta_1$-antisense, through specific inhibitions of $\beta_1$-AR expression, decreases the functional sensitivity of $\beta_1$-AR-mediated responses in the face of sympathetic activation and thereby achieves an antihypertensive effect. In this example, an AS-ODN was designed complementary to rat $\beta_1$-AR mRNA and its ability was demonstrated to inhibit $\beta_1$-AR density and function in the heart and to reduce BP in spontaneously hypertensive rats.

5.1.1 Methods 5.1.1.1 Antisense Design and Administration

AS-ODN and inverted ODN control were 15-mer and targeted to the AUG start codon of rat $\beta_1$-AR mRNA (Machida et al., 1990). The sequence of AS-ODN is 5'-CCGCGCCCATGCCGA-3' (SEQ ID NO:195), and the inverted ODN is 5'-AGCCGTACCCGCGCC-3' (SEQ ID NO:196). This AS-ODN was chosen from 6 AS candidates targeted to different regions of $\beta_1$-AR mRNA on the basis of the intensity of cardiac $\beta_1$-AR inhibition and reduction of BP in SHRs. These oligonucleotides were modified by backbone phosphorothioation. ODNs delivered with cationic liposomes were injected into the tongue vein.

5.1.1.2 Preparation of Liposomes and ODN/Liposome Complex

The cationic lipid 1,2-bis(oleoyloxy)-3-(trimethylammonio)propane (DOTAP) was mixed with helper lipid 1-α-dioleoyl phosphatidylethanolamine (DOPE, Avanti Polar Lipids, Alabaster, Ala.) at a 1:1 molar ratio, briefly sonicated, and stored at 4° C. until use. The average diameter of liposomes is 200 to 300 nm (Tang and Hughes, 1998). ODN/liposome complex was prepared on the day of use by mixing the desired amounts of ODNs with DOTAP/DOPE to the final DNA concentration of 300 μg/mL in 5% wt./vol. dextrose in water and incubating at room temperature for 60 min. Two DNA/lipid molar ratios, i.e. 1:0.5 and 1:2.5, were used in the studies.

5.1.1.3 Animal Surgery

Adult male SHRs (250 to 350 g, Harlan, Indianapolis, Ind.) were kept in cages in a room with a 12-hr. light-dark cycle. Animals were fed standard laboratory rat chow and tap water ad libitum.

5.1.1.4 Telemetric Sensor Implantation

Before implantation, the zero of each radiotransmitter (TA11PA-C40, Data Sciences, St. Paul, Minn.) was verified to be ≦4 mm Hg. SHRs were anesthetized with 100 mg/kg ketamine and 15 mg/kg xylazine, and a midline abdominal incision was made. A fluid-filled sensor catheter was then inserted into the right femoral artery, and the tip of the catheter was in the abdominal aorta caudal to the renal arteries. The rats with implants were allowed to recover for 1 week.

5.1.1.5 Jugular Vein Cannulation

One week after telemetric implantation, rats were anesthetized, and a curved catheter made of PE 50 and vinyl tubing was inserted into a curved catheter made of PE 50 and vinyl tubing was inserted into the jugular vein. The tubing was led under the skin of the neck and exposed on the back to allow for drug infusion. Rats were allowed to recovery for 24 hr before experimentation. The catheters were flushed with 100 U heparin every day to prevent clogging.

5.1.1.6 Membrane Preparation and β-AR Binding Assay

Four days after intravenous injection of saline (n=6) or 1 mg/kg inverted ODN (n=6) or 2, 4, 10 or 18 days after injection of 1 mg/kg $β_1$-AS-ODN (n=24), animals were euthanized, and membranes were prepared from heart ventricles as previously described (Baker and Pitha, 1982). For saturation experiments, 100 μg membrane protein was incubated in triplicate with 6 concentrations of $[^{125}I](^-)$-iodocyanopindolol (ICYP, NEN Life Science, 6.25 to 100 pmol/L) in a total volume of 250 μL containing 50 mmol/L Tris-HCl (pH 7.4), 5 mmol/L $MgCl_2$ at 36° C. for 60 minutes. The nonspecific and $β_2$-AR-binding levels were determined in the presence of 1 μmol/L (±)-alprenolol and 150 nmol/L CGP20712A (RBI), respectively. Then the reaction mixture was passed through Whatman (GF/B glass fiber filter using a Brandel harvester, and the bound radioactivity was counted for 1 min.

5.1.1.7 Tissue Preparation and Quantitative Autoradiography

Four days after injection of 1 mg/kg $β_1$-AS-ODN (n=6) or saline (n=6), rats were killed, and tissues were removed and frozen in dry ice. Coronal sections of brain, horizontal sections of heart, and sagittal sections of kidney (20 μm) were cut on a cryostat (Microm, Thornwood, N.Y.) at $-20°$ C. and mounted on microscope slides. Every seventh slide was stained with hematoxylin and eosin for histology. Tissue sections were preincubated in Krebs buffer (mmol/L: NaCl 118.4, KCl 4.7, $MgSO_4$ 1.2, $CaCl_2$ 1.27 and $NaH_2PO_4$ 10.0, pH 7.1) containing 0.1 mmol/L GTP, 0.1 mmol/L ascorbic acid, and 10 μmol/L PMSF for 30 minutes at 25° C. Sections were then incubated in Krebs buffer containing 0.1 mmol/L ascorbic acid and 10 μmol/L PMSF with 100 pmol/L ICYP at 25° C. for 150 minutes in the presence of 1 μmol/L ($^-$) propranolol, 100 nmol/L ICI 118,551 ($β_1$-selective antagonist), or 100 nmol/L CGP20712A ($β_1$-selective antagonist) to distinguish nonspecific, $β_{1-}$, and $β_2$-bindings. Labeled sections were rinsed in the same buffer, followed by two 15-min. washes at 37° C. in the buffer, and rinsed in distilled water at 25° C. (Matthews et al., 1994). Dried sections were then exposed to x-ray films. The images were quantified with a computerized image analysis system (MCID, Imaging Research) and normalized with $^{125}I$ standards. Nonspecific binding was <10% of total binding.

5.1.1.8 Determination of Effects of $β_1$-AS and Atenolol on Cardiovascular Parameters in Response to β-Stimulation 48 hr after injection of 1 mg/kg $β_1$-AS-ODN (n=9) or inverted ODN (n=6), SHRs were anesthetized and killed. Hearts were quickly removed and perfused via the aorta with oxygenated Krebs buffer (118 mmol/L NaCl, 18.75 mmol/L $NaHCO_3$ 1.2 mmol/L $KH_2PO_4$, 4.7 mmol/L KCl, 1.2 mmol/L $MgSO_4$, 1.25 mmol/L $CaCl_2$, 11.1 mmol/L glucose, and 0.01 mmol/L EDTA) at a constant flow of 7.0 mL/min. at 36° C. Coronary perfusion pressure was measured via a catheter placed proximal to the aorta and connected to a pressure transducer (Gould Staham P23ID, Eastlake, Ohio). A latex balloon filled with water and connected to the pressure transducer was inserted into the left ventricle through the left atrium to measure left ventricular end-diastolic pressure (LVEDP), left ventricular systolic pressure (LVSP), and developed left ventricular pressure (dLVP) (dLVP=LVSP−LVEDP). LVEDP during equilibration was set at 5 to 7 mm Hg. Coronary perfusion pressure, LVEDP, and LVSP were recorded continuously on a 4-channel recorder (Astro-Med, West Warwick, R.I.). After baseline values for dLVP and heart rate (HR) were stable for 5 min., isoproterenol (ISO, nonspecific β-agonist) was given at 0.01, 0.025, 0.05, and 0.12 μmol/L at 10 min. intervals so as to avoid the effect of tachyphylaxis.

The effects of $β_1$-AS-ODN and atenolol on cardiac $dP/dt_{max}$ and systolic blood pressure (SBP) were compared in the same group of SHRs (n=4). Two days after catherization of the jugular vein, control values were taken and 1 mg/kg $β_1$-AS-ODN was injected. 48 hr later, rats were tested for the effect of $β_1$-AS-ODN. The rats were allowed to recover until all the cardiovascular parameters returned to control values. Then 1 mg/kg atenolol ($β_1$-selective antagonist) was injected, and rats were tested 30 min. later. For $β_1$-stimulation, SHRs were infused with dobutamine ($β_1$-selective agonist) through a jugular vein catheter at 5, 10, 20, and 40 $μg·kg^{-1}·min.^{-1}$. Each dose was given for 5 min. continuously and at 1-hr intervals until all the cardiovascular parameters returned to baseline values so as to avoid the effect of tachyphylaxis. BP and HR were sampled every 1 min. $dP/dt_{max}$ was calculated from the slope of the rising pulse-pressure curve and determined every 1 min. The difference between values at each dose and baseline was denoted as Δ.

5.1.1.9 BP Monitoring

Each rat cage was placed on a receiver (RLA 1020, Data Sciences, St. Paul, Minn.) for measurement of cardiovascular parameters. Data were collected with a computer-based data acquisition program (Dataquest Lab-PRO3.0; Data Sciences). BP and HR were measured every 10 min. and averaged every 1 to 24 hrs. Before treatment, SHRs were monitored for a week to get a stable baseline.

Rats were warmed for 20 to min. in cages on heating pads. The temperature was controlled at 35° C. to 37° C. Then the rats were placed in a plastic restrainer kept at 37° C. A pneumatic pulse sensor was attached to the tail. After cuff inflation, SBP was determined as the first pulsatile oscillation on the descending side of the pressure curve. HR was determined by manual counting of pulse numbers per unit time. BP and HR were recorded by a Narco physiograph. Data values of each rat were taken as an average of at least 4 stable readings. Baseline was determined by averaging 3 days of measurements before antisense administration.

5.1.1.10 Statistical Analysis

Values were expressed as mean±SEM. The difference was considered statistically significant at P<0.05. An unpaired t test was used to compare $B_{max}$, dLVP, and BP in 2 groups. One-way repeated-measures ANOVA and Tukey test were used to compare ΔdP/dt and ΔHR on dobutamine infusion in different groups. Pearson product-moment correlation was used to assess the relationship between $β_1$-AR $B_{max}$ and dLVP.

5.1.2 Results 5.1.2.1 Effect on Cardiac β-AR Density

Figure 1A:
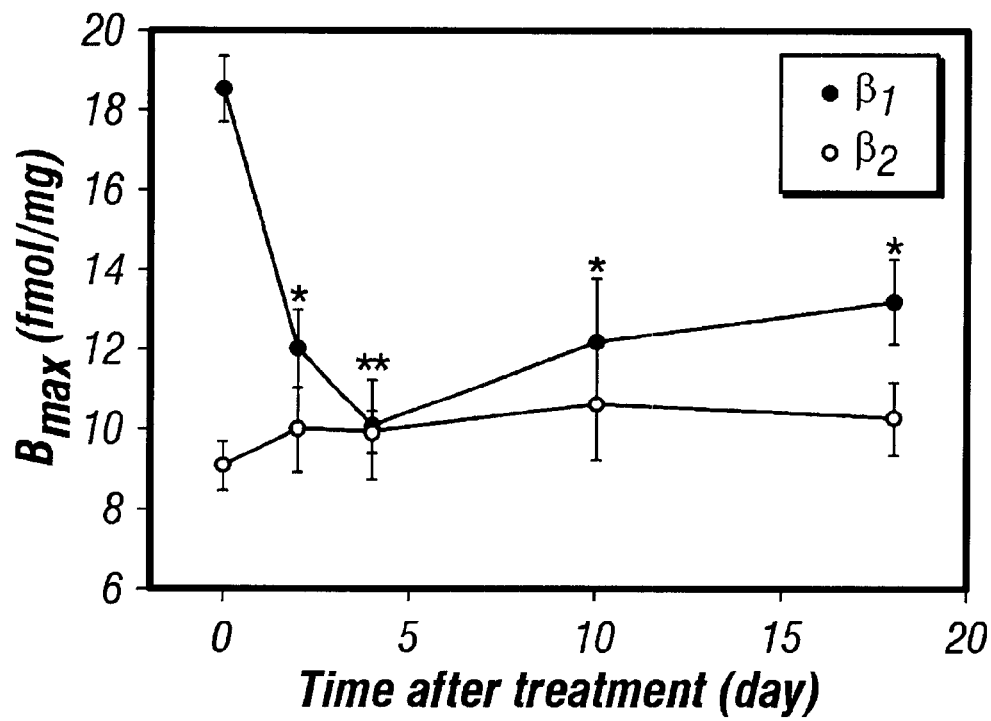
FIG. 1A shows $\beta_1$-AS-ODN decreased density of $\beta_1$-ARs but not $\beta_2$-ARs in cardiac ventricles of SHRs. A[1] Time Course of $\beta_1$-AS-ODN effects on $B_{max}$ of $\beta_1$-ARs (●) and $\beta_2$-ARs (○).
Figure 1B:
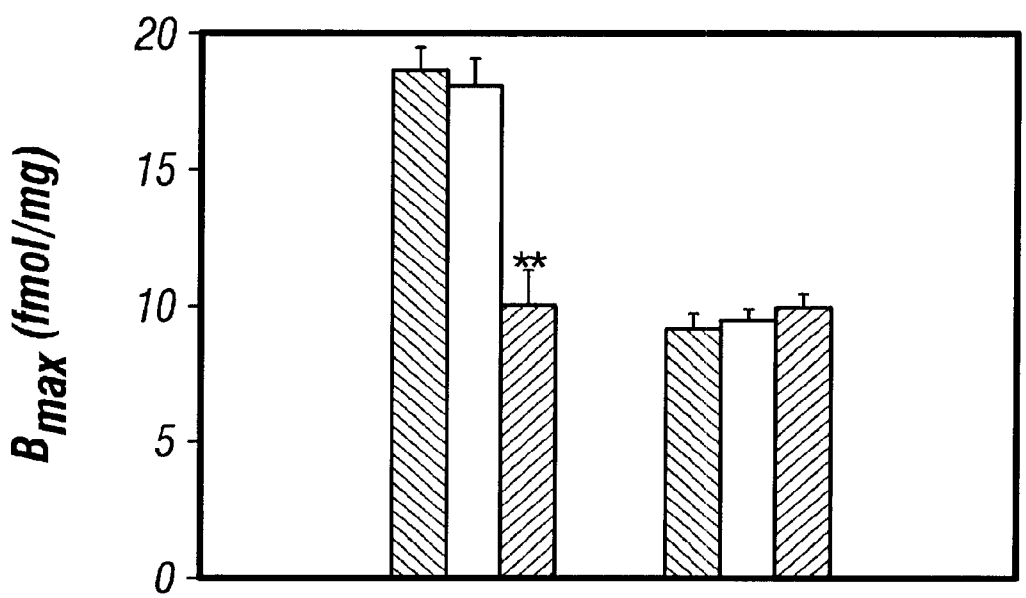
FIG. 1B shows $B_{max}$ of β-ARs 4 days after intravenous injection of saline (solid bar), 1 mg/kg inverted ODN (open bar), or 1 mg/kg $\beta_1$-AS-ODN (shaded bar). Data represent mean±SEM of each point (n=6). *P<0.01, **P<0.001 vs. saline control.

FIG. 1A shows that a single intravenous injection of 1 mg/kg $β_1$-AS-ODN delivered with cationic liposomes at a 1:2.5 molar ratio significantly reduced the $β_1$-AR density in the SHR hearts for 18 days (P<0.01). The drop was at its maximum of 470/0 on day 4, 33% on day 10 and maintained at 29% on day 18. In contrast, there was no significant change in the $B_{max}$ of $\beta_2$-ARs. The $K_D$ of both subtypes remained unaltered (Table 1). Consequently, the $\beta_1/\beta_2$ subtype ratio in the ventricles was diminished from ≈70/30 to ≈50/50 by $\beta_1$-AS-ODN. Inverted ODN had no effect on either subtype (FIG. 1B).

5.1.2.2 Effect on Cardiac Contractility and HR in Response to $\beta$-Stimulation 48 hr after injection of 1 mg/kg $\beta_1$-AS-ODN, the cardiac inotropic and chronotropic responses to $\beta$-stimulation were determined in SHRs in vitro and in vivo.

First, isolated hearts were perfused with incrementing doses of ISO, which enhanced HR and contractility via activating $\beta$-ARs. The dLVP-ISO dose-response curve, which reflected the positive inotropic effect of ISO, was significantly shifted downward by $\beta_1$-AS-ODN (P<0.02). HR was not significantly decreased, except at 1 point, i.e. 0.01 μmol/L ISO (P<0.05) (FIG. 2A and FIG. 2B).

An in vivo test was performed in conscious SHRs monitored by radiotelemetry. $\beta$-AS-ODN significantly (P<0.02) dampened the increase in $dP/dt_{max}$ in the face of dobutamine ($\beta_1$-selecrive agonist) (FIG. 3A). The change in HR was not significantly reduced (FIG. 3B), which echoed the results in isolated perfused hearts. Conversely, the response of BP to dobutamine was biphasic (FIG. 3C). Dobutamine elevated SBP by 5 to 8 mm Hg at low infusion speed and reduced SBP at higher speed, probably as a result of the partial $\beta_2$-agonistic activity of dobutamine at high doses and the consequent vasodilatory effect on BP. FIG. 3 also compares the results with $\beta_1$-AS-ODN and atenolol ($\beta_1$-selective antagonist). Relative to $\beta_1$-AS-ODN, 1 mg/kg atenolol produced a more profound decline in $\Delta dP/dt_{max}$ and ΔHR during a 5 hr. period of time after injection. Moreover, it reduced basal $dP/dt_{max}$ (2450±295 mm Hg/s versus control, 2937±277 mm Hg/s) and caused bradycardia (295±12 bpm versus control, 365±8 bpm) (P<0.05), whereas $\beta_1$-AS did not change basal contractility (2922±249 mm Hg/s) or HR (365±12 bpm). But the effects of atenolol on $\Delta dP/dt_{max}$ and ΔHR were transient. Within 24 hr after atenolol administration, the inotropic and chronotropic effects of dobutamine had returned to control levels.

When the molar ratio was increased to 1:2.5, this hypotensive effect was drastically prolonged to 20 days. No effect was seen with inverted ODN.

To compare the effects of $\beta_1$-AS-ODN and atenolol, radiotelemetry was used to monitor BP and HR on a regular basis. $\beta_1$-AS-ODN 1 mg/kg delivered with liposomes at a 1:0.5 ratio produced a maximum drop of 15 mm Hg in mean BP (FIG. 5A). The antihypertensive effect lasted for 8 days, which was consistent with the results measured with the tail cuff. HR was not significantly altered (FIG. 5B). In contrast to AS-ODN, although the onset of the hypotensive effect caused by 1 mg/kg atenolol occurred as early as 20 min. after injection, it lasted for only 10 hr (FIG. 6A). In addition, atenolol caused considerable bradycardia up to an average of $^-$75 bpm (FIG. 6B).

5.1.2.4 Effect on $\beta$-AR Distribution in Brain, Heart, and Kidney

Quantitative autoradiography of 6 to 18 tissue slices in brain, heart, and kidney was analyzed 4 days after intravenous $\beta_1$-AS-ODN administration. No changes in the distribution of $\beta$-ARs in the forebrain and brain stem regions were detected. This indicated the absence of antisense effect on the $\beta$-AR expression in CNS. However, $\beta_1$-AS-ODN significantly (P<0.05) reduced $\beta_1$-AR density in cardiac ventricles (from 30.2±2.1 to 20.6±2.5 fmol/mg) and renal cortex (from 26.4±3.1 to 17.4±3.3 fmol/mg). This was consistent with the binding results. $\beta_2$-ARs were not affected in any tissues.

5.1.3 Discussion

This example compares the effects of a novel $\beta_1$-AS-ODN on high BP in a model of hypertension with a currently used $\beta$-blocker. $\beta_1$-AS-ODN knocked down $\beta_1$-adrenergic activity, resulting in long-term attenuation of BP. The results indicated that $\beta_1$-AS-ODN reduced $\beta_1$-AR density and cardiac contractility after $\beta_1$-stimulation in vitro and in vivo and lowered high BP of SHRs. These findings are consistent with the hypothesis that $\beta_1$-AS, through the inhibition of $\beta_1$-AR expression, is able to render heart, kidney, and other tissues less sensitive to sympathetic activation, which is a major contributing factor in high BP. A single injection of $\beta_1$-AS-ODN effectively decreased the cardiac $\beta_1$-AR density, which was accompanied by diminished ventricular

TABLE 3

$B_{MAX}$ AND $K_D$ OF $\beta_1$- AND $\beta_2$-ARs IN CARDIAC VENTRICLES OF SHRs 4 DAYS AFTER TREATMENT WITH SALINE, INVERTED ODN, OR $\beta_1$-AS-ODN

| | Total ($\beta_1+\beta_2$) | | $\beta_1$ | | $\beta_2$ | |
|---|---|---|---|---|---|---|
| | $K_D$, pmol/L | $B_{max}$, fmol/mg | $K_D$, pmol/L | $B_{max}$, fmol/mg | $K_D$, pmol/L | $B_{max}$, fmol/mg |
| Saline | 55.4 ± 6.7 | 27.6 ± 0.9 | 64.7 ± 5.4 | 18.7 ± 0.9 | 29.6 ± 0.5 | 9.1 ± 0.6 |
| Inverted ODN | 57.1 ± 3.5 | 26.3 ± 3.0 | 66.0 ± 1.0 | 18.1 ± 2.3 | 32.0 ± 2.4 | 8.7 ± 0.5 |
| $\beta_1$-AS-ODN | 37.0 ± 1.0* | 19.8 ± 1.8* | 60.5 ± 3.4 | 10.0 ± 1.2* | 30.7 ± 3.3 | 9.9 ± 0.5 |

Data represent mean ± SEM of each group (n = 6 to 10)
*p < 0.01 vs. saline control 5.1.2.3 Effect on BP of SHRs FIG. 4 shows the effects of a single injection of 1 mg/kg $\beta_1$-AS-ODN on the BP of SHRs measured by the tail-cuff method. AS-ODN was delivered with cationic liposomes at different molar ratios of DNA/lipid, i.e. 1:0.5 and 1:2.5. $\beta_1$-AS-ODN delivered with liposomes at a 1:0.5 ratio diminished SBP for 8 days. The maximum drop was 38±5 mm Hg.

contractility and cardiac output in response to $\beta$-stimulation. The antihypertensive effect in SHRs was up to a 38 mm Hg reduction lasting as long as 20 days.

Treatment of $\beta_1$-AS-ODN reduced cardiac $\beta_1$-AR density by ≈50% in 4 days. Considerable variation is reported in the literature on the half-life of $\beta_1$-ARs (Baker and Pitha, 1982; Neve and Molinoff, 1986 and Winter et al., 1988). From the results with the AS-ODN inhibition, the half-life of cardiac $\beta_1$-ARs is ≈2 to 4 days to allow for 50% reduction of $\beta$-AR density within 4 days.

Both tail-cuff and telemetry measures of BP showed a significant drop after antisense treatment. SHRs responded to $\beta_1$-AS-ODN to a greater degree of hypotension when subjected to tail cuff vs. telemetry. In addition, the baseline measured with the tail cuff was consistently higher than that with telemetry by 20 to 30 mm Hg in the same rats. Bazil et al., 1993 reported a similar phenomenon. They compared the cardiovascular parameters recorded by telemetry, tail cuff, and arterial catheter and observed a more sensitive hypotensive effect of captopril with tail cuff. Tail-cuff measurement of BP involves warming and restraint of rats. It is conceivable that $\beta_1$-AS, through the suppression of sympathetic activity, can decrease the BP of animals under stress more effectively.

Cationic liposomes are effective vehicles for gene delivery. It has been shown that liposomes entrapment not only improves the cellular uptake of DNA but also protects DNA from degradation and extends its circulation time (Allen, 1997; Liu et al., 1997). Numerous factors influence the efficiency of cationic liposome-mediated intravenous gene delivery, such as DNA/lipid ratio, selection of lipids, and preparation procedure. A widely used lipid formula, DOTAP/DOPE, was used to deliver $\beta_1$-AS-ODN at 4 molar ratios. The optimal ratio of 1:2.5 was determined on the basis of the duration and magnitude of the antihypertensive effects. A profound and prolonged fall in BP of 38 mm Hg up to 20 days was achieved at this ratio, which followed the reduction in $\beta_1$-AR binding to a maximum of 47% at day 4, 33% at day 10, and 29% at day 18. This implies that $\beta_1$-AS-ODN effectively inhibits the functionally active receptors involved in the BP.

The blood-brain barrier formed by capillary endothelia is permeable only to small lipophilic molecules with a molecular weight of <600 Da (reviewed by Pardridge, 1998). Owing to their high hydrophilicity, ODNs undergo negligible transport through blood-brain barrier and have very limited access to CNS. The cellular and organ distributions of DNA/liposome complexes with fluorescent labeling were previously studied in mice after intravenous injection, and the results indicated that the complexes were taken up primarily by capillary endothelial cells in most of the peripheral organs, including lung, heart, kidney, and spleen, but were absent in the brain (McLean et al., 1997). Although brain retention of liposomes after peripheral administration was observed in some cases, it was due to entrapment within the brain microvasculature (Schackert et al., 1989). Autoradiography in brain revealed no detectable changes in the expression and distribution of $\beta$-ARs after intravenous $\beta_1$-AS-ODN injection. This provided further evidence that the use of antisense did not have CNS effects.

High specificity based on gene sequence has made antisense an increasingly useful tool in numerous studies and clinical trials. Its success is manifested by the recent approval of the first antisense drug, Vitavene, by the Food and Drug Administration. However, sequence-independent interactions have also been reported with AS-ODNs. High doses are usually responsible for the nonspecific effects (Chang et al., 1989), but another possible reason is that currently available databases do not cover every gene; thus, homology comparison by BLAST search may no guarantee sequence specificity of AS-ODNs. In this study, $\beta_1$-AS-ODN inhibited $\beta_1$-AR expression without changing $\beta_2$-ARs. Although this is likely due to the specificity of the $\beta_1$-AS-ODN sequence, other possibilities remain, such as indirect effects on regulatory mechanisms.

In patients with chronic heart failure, the severity of the disease closely relates to the decrease in cardiac $\beta$-AR density and functional responsiveness (Brown et al., 1992). In SHRs treated with $\beta_1$-AS-ODN, a marked attenuation of the $\beta_1$-AR-mediated positive inotropic response in vitro and in vivo, concurrent with the diminished cardiac $\beta_1$-AR level. Therefore, these results indicated a positive correlation between cardiac $\beta_1$-AR number and functional sensitivity (correlation coefficient>0.90, P<0.01).

Despite the large decrease in BP, no reflex tachycardia was observed after antisense treatment. However, the suppressive effect of $\beta_1$-AS-ODN on Hr was less significant than its negative inotropic response. Several possibilities can be considered. First, $\beta_1$-AS-ODN did not affect $\beta_2$-ARs, which played an important role in the regulation of HR (Kaumann, 1986; Rodefeld et al., 1996), although it was not involved in the cardiac contraction. Second, antisense inhibition of $\beta_1$-AR expression is gradual and less extensive than with $\beta$-blockers. It is also possible that $\beta_1$-ARs may have a larger reserve for controlling HR than contractility.

5.2 Example 2

Prolonged Reduction in High Blood Pressure With $\beta_1$ AR Oligodeoxynucleotides Since the introduction of propranolol in 1965, $\beta$-blockers have become major first-line drugs for hypertension. Through the inhibition of $\beta$-adrenergic receptors in heart and kidney, $\beta$-blockers lower high blood pressure via the reduced response to the sympathetic nervous system. However, all current $\beta$-blockers have to be taken daily. Also, most have central nervous system side effects that lead to poor patient compliance. Furthermore, the mechanism of $\beta$-blockade in hypertension is not well understood (Man in't Veld et al., 1988). Antisense oligonucleotides have been successfully constructed to components of the renin-angiotensin system (RAS) to decrease blood pressure (Phillips et al., 1994). In view of this, novel antisense oligonucleotides targeted to $\beta_1$-adrenergic receptors ($\beta_2$-ARs), or the brain. Therefore, it is likely to have fewer side effects and longer-lasting action.

It has been previously shown that antisense oligodeoxynucleotide ($\beta_1$-AS-ODN) significantly inhibits $\beta_1$-AR expression in the cardiac ventricles, which results in suppressed inotropic response to adrenergic activation and thereby contributes to hypotension. In addition to inducing positive inotropy and chronotropy in the heart, $\beta_1$-ARs are also responsible for mediating the sympathetic stimulation of renin expression and secretion from juxtaglomerular cells of the renal cortex. Infusion of isoproterenol has been shown to increase renin expression and secretion and plasma renin activity (PRA) in rats (Holmer et al., 1997). $\beta$-Blockers reduce PRA in patients, (Blumenfeld et al., 1999). However, despite the evidence that $\beta$-blockers are more effective in patients with high renin profiles (Buhler, 1988), the importance of $\beta$-blocker-induced decreases in renin release has been debated (Man in't Veld et al., 1983). The present study investigates whether $\beta_1$-AS-ODN reduces renin expression and secretion and whether the RAS is involved in the antihypertensive impact of $\beta_1$-AS-ODN could be improved by delivery with cationic liposomes and to determine the optimal charge ratio of liposome:ODN.

5.2.1 Methods 5.2.1.1 Antisense Sequence and Delivery

AS-ODN and inverted ODN control were 15-mer and targeted to the AUG start codon of rat $\beta_1$-AS-ODN is 5'-CCGCGCCCATGCCGA-3' (SEQ ID NO:197), and the inverted ODN is 5'-AGCCGTACCCGCGCC-3' (SEQ ID NO:198). These ODNs were modified by backbone phosphorothioation. The cationic lipid 1,2-bis(oleoyloxy)-3-(trimethylammonio)propane (DOTAP) mixed with the helper lipid L-α-dioleoyl phosphatidylethanolamine (DOPE, Avanti Polar Lipids) at 1:1 molar ratio was used to deliver ODNs in a single intravenous injection into the tongue vein. ODN-liposome complex was prepared on the day of use by mixing desired amounts of ODNs with DOTAP/DOPE to a final DNA concentration of 300 µg/mL in 5% (wt./vol.) dextrose in water and incubating at room temperature for 60 min.

5.2.1.2 Animals

Adult male SHR (4 to 6 mos. old, Harlan, Indianapolis, Ind.) were kept in cages in a room with a 12 hr. light-dark cycle. Animals were fed standard laboratory rat chow and tap water ad libitum. Tail blood was collected for determination of PRA and angiotensin II (Ang II) levels.

5.2.1.3 Blood Pressure Measurement

Blood pressure was measured by the tail-cuff method as described above. Systolic blood pressure (SBP) was determined as the first pulsatile oscillation on the descending side of the pressure curve. Data values of each rat were taken as an average of ≧4 stable readings. Baseline was determined by averaging 3 days of measurements before antisense administration.

5.2.1.4 Membrane Preparation and β-Adrenergic Receptor Binding Assay

Four days after intravenous injection of saline (n=6) or 0.5 mg/kg inverted ODN (n=6) or 4, 10, 18 and 40 days after injection of 0.5 mg/kg $β_1$-AS-ODN (n=24), animals were euthanized, and membranes were prepared from the renal cortex of the left kidneys as previously described (Baker and Pitha, 1982). For saturation studies, 100 µg membrane protein was incubated in triplicate with 6 concentrations of $[^{125}I]$(–)iodocyanopindolol (ICYP, NEN Life Science, 6.25 to 100 pmol/L) in a total volume of 250 µL containing 50 mmol/L Tris-HCl (pH 7.4) and 5 mmol/L MgCl$_2$ at 36° C. for 60 min. The nonspecific and $β_2$-adrenergic receptor binding levels were determined in the presence of 1 µmol/L (±)-alprenolol and 150 mmol/L CGP20712A (RBI), respectively. Then the reaction mixture was passed through a Whatman GF/B glass fiber filter with a Brandel harvester, and the bound radioactivity was counted for 1 min.

5.2.1.5 Tissue Preparation and Quantitative Autoradiography

Four days after injection of 0.5 mg/kg $β_1$-AS-ODN (n=6) or saline (n=6), rats were euthanized, and the right kidneys were removed and frozen in dry ice. Sagittal sections of kidney (20 µm) were cut on a cryostat (Microm) at –20° C. and mounted on microscope slides. Every seventh slide was stained with hematoxylin and eosin for histology. Receptor autoradiography was performed as described (Matthews et al., 1994) with 100 pmol/L ICYP at 25° C. for 150 min. in the presence of 1 µmol/L (–)-propranolol, 100 mmol/L ICI 118,551 ($β_2$-selective antagonist), or 100 nmol/L CGP 20712A ($β_1$-selective antagonist) to distinguish nonspecific, $β_1$, and $β_2$-bindings. The images were quantified with a computerized image analysis system (MCID, Imaging Research) and normalized with $^{125}I$ standards. Nonspecific binding was <10% of total binding.

5.2.1.6 Reverse Transcription-Polymerase Chain Reaction and Southern Blotting

At different time points after the single injection of $β_1$-AS-ODN or inverted ODN, rats were euthanized, and the renal cortex was dissected from the left kidneys, immediately dipped into RNAlater tissue storage buffer (Ambion), and stored at –20° C. Total RNA was extracted with RNAwiz reagent (Ambion) and quantified by spectrophotometer. RNA samples from 4 to 5 rats from each time point were pooled. RNA (5 µg) was digested by DNase I and reverse-transcribed by Superscript reverse transcriptase (GIBCO BRL) at 42° C. for 50 min. and 1/20 of the reverse transcription (RT) product was used to run a polymerase chain reaction (PCR) for 20 cycles. PCR primers for $β_1$-AR were 5'-CTCCGAAGCTCGGCATGG-3' (SEQ ID NO:199) (forward) and 5'-GCACGTCTACCGAAGTCCAGA-3' (SEQ ID NO:200) (reverse) and yielded products of 432 bp, which spanned the AUG start codon. Primers for preprorenin were 5'-AGGCAGTGACCCTCAACATTACCAG-3' (SEQ ID NO:201) (forward) and 5'-CCAGTATGCACAGGTCATCGTTCCT-3' (SEQ ID NO:202) (reverse) and yielded products of 362 bp.

Primers for GAPDH were 5'-ATCAAATGGGGTGATGCTGGTGCTG-3' (SEQ ID NO:203) (forward) and 5'-CAGGTTTCTCCAGGCGGCATGTCAG-3' (SEQ ID NO:204) (reverse) and yielded products of 505 bp (Jo et al., 1996). RT-PCR products were subjected to Southern blotting, hybridized with psoralen-biotin-labeled cDNA probes, and detected with nonisotopic kits (Ambion). After the membranes had been exposed to x-ray films, the intensity of $β_1$-AR and preprorenin mRNAs was quantified by densitometry and normalized with GAPDH mRNA levels. The studies were repeated at least twice.

5.2.1.7 PRA and Plasma Ang II Levels

PRA was determined with an angiotensin I ($^{125}I$) radioimmunoassay kit (DuPont). Plasma Ang II levels were measured by radioimmunoassay as previously described (Phillips and Kimura, 1988).

5.2.1.8 Statistical Analysis

Values were expressed as mean±SEM. Differences were considered statistically significant at a value of P<0.05. One-way repeated ANOVA and Tukey's test were used to compare blood pressure before and after AS-ODN treatment. Unpaired t test was used to compare $B_{max1}$, PRA, and plasma Ang II levels in 2 groups.

5.2.2 Results 5.2.2.1 Optimization of $β_1$-AS-ODN Delivery by Cationic Liposomes Systemic delivery of AS-ODN was optimized with the commercially available cationic lipid DOTAP mixed with neutral lipid DOPE. Previous studies reported that a charge ratio of DOTAP:DNA of ≈2.0 achieved the best gene delivery in vivo and in vitro (Yang et al., 1997 and Templeton et al., 1997). Therefore, 5 charge ratios of DOTAP:ODN were tested ranging from 0 to 3.5 to deliver 0.5 mg/kg $β_1$-AS-ODN intravenously. It was noticed that different batches of liposome mixture varied slightly in structure and particle size, which may influence the delivery efficiency. FIG. 7 shows the effect of different liposome:ODN charge ratios on blood pressure of SHR (n=6 for each ratio) in a representative experiment. $β_1$-AS-ODN alone, i.e. at ratio 0, did not change SBP, whereas ratio 0.5 significantly reduced SBP by up to 33 mm Hg for 7 to 8 days. When the ratio was increased, the duration of the hypotensive impact was drastically prolonged to 20 days at ratio 1.5 and 33 days at ratio 2.5 and 3.5, varying with liposome preparations. But the maximum drop in SBP was greater at ratio 1.5 and 2.5 (≈35 mm Hg) than at ratio 3.5 (≈25 mm Hg) (Table 2). Accordingly, the optimal charge ratio of DOTAP:ODN was determined to be 2.5. In the subsequent experiments, SHR (n=24) injected with 0.5 mg/kg $β_1$-AS-ODN with liposomes at a charge ratio of 2.0 were analyzed for the time course of changes in SBP, receptor levels, and peripheral RAS.

TABLE 4

RANGES OF AMPLITUDE AND DURATION OF REDUCTION IN BLOOD PRESSURE OF SHR AFTER A SINGLE INTRAVENOUS INJECTION OF 0.5 MG/KG $\beta_1$-AS-ODN DELIVERED IN DIFFERENT CHARGE RATIOS OF LIPOSOME/ODN

| Charge Ratio of Liposome/ODN | Maximum Reduction in Blood Pressure, mm Hg | Range of Reduction, mm Hg | Duration, d (Range |
|---|---|---|---|
| 0 | 2 | *** | *** |
| 0.5 | 35–38 | 24–38 | 7–8 |
| 1.5 | 28–35 | 18–35 | 18–20 |
| 2.5 | 30–34 | 20–34 | 20–33 |
| 3.5 | 20–24 | 15–24 | 20–33 |

5.2.2.2 Effects of $\beta_1$-AS-ODN on $\beta$-Adrenergic Receptors in Renal Cortex Scatchard analysis of $\beta$-AR binding in renal cortex (FIG. 8A, FIG. 8B and FIG. 8C) indicated that $\beta_1$-AR was the major subtype in the control rats, composing 70% of total $\beta$-AR. After $\beta_1$-AS-ODN injection, the $B_{max}$ of $\beta_1$-ARs was diminished significantly, by 35% on day 4 (P<0.05), 29% on day 10 (P<0.05), and 23% on day 18, and completely restored on day 40. $\beta_1$-AR reduction in kidney coincided with that in heart, and both were accompanied by a significant drop in SBP (P<0.0 1) (FIG. 8A). In contrast, the $\beta_2$-AR level was not affected (FIG. 8B), nor was the affinity of either subtype. Inverted ODN had no effect on either subtype (FIG. 8C).

Kidney slices from the same rats were subject to quantitative autoradiography to display the structural distribution of $\beta$-ARS. $\beta_1$-Subtype composed ≈60% of the $\beta$-AR levels, which was localized predominantly in the renal cortex and the outer band of the medulla. $\beta_2$-Subtype was more diffusely distributed in the kidney at a lower level. This result was consistent with previous reports (Summers et al., 1985). Four days after $\beta_1$-AS-ODN treatment, the overall density of $\beta_1$-subtype in kidney was significantly reduced from 23.5±2.1 to 15.4±3.3 fmol/mg (P<0.05). The diminution in renal cortex was particularly conspicuous because of the higher basal level. As expected, the distribution and concentration of $\beta_2$-subtype remained unchanged in accord with binding results. This further confirms the specificity of the inhibitory effect of $\beta_1$-AS-ODN on $\beta_1$-subtype.

In an effort to demonstrate whether $\beta_1$-AS-ODN decreases the mRNA level of $\beta_1$-AR by inducing RNase H digestion, a pair of primers flanking the AUG start codon where $\beta_1$-AS-ODN was targeted was used to run a semi-quantatitative RT-PCR™ for 20 cycles, followed by Southern blotting. $\beta_1$-AS-ODN did not reduce the level of steady-state $\beta_1$-AR mRNA in renal cortex, indicating that the inhibition of $\beta_1$-AR expression was not at the transcriptional level.

5.2.2.3 Effect of $\beta_1$-AS-ODN on Peripherl RAS

RT-PCR™ revealed that the preprorenin mRNA level in renal cortex was transiently decreased to 62% of control 4 days after $\beta_1$-AS-ODN injection. It was completely reversed by day 18 (FIG. 9A). Conversely, PRA and plasma Ang II levels showed different patterns of reduction, which were significantly decreased on day 10 and day 18 (P<0.01) but not on day 4. Thus, PRA and Ang II seemed to have as delayed action relative to the reduction in renin mRNA (FIG. 9B).

5.2.3 Summary

Because $\beta_1$-adrenergic receptors are also involved in renin expression and secretion from the kidney, the present study was designed to evaluate the effect of $\beta_1$-AS-ODN on peripheral RAS and its contribution to the reduction in blood pressure. In addition, a significant improvement of hypotensive action up to 33 days was achieved by optimizing the delivery of $\beta_1$-AS-ODN with cationic liposomes.

$\beta$-blockers have been used to treat hypertension for 3 decades. The reasons for their antihypertensive effects remain largely unclear, but the inhibition of renin release is regarded as a primary mechanism. Many $\beta$-blockers can reduce PRA in patients and experimental animals (Blumenfeld et al., 1999 and Holmer et al., 1994). They are found to be more effective in patients with higher renin profiles (Buhler, 1988). In this study, it was found that $\beta_1$-AS-ODN effectively decreased PRA and Ang II in the long term. But the decrease in PRA and Ang II did not occur until ≈10 days after $\beta_1$-AS-ODN injection, in contrast to the rapid drop in cardiac output 2 days after injection. Thus, it appears that the effects of $\beta_1$-AS-ODN on the kidney renin and the circulating RAS are more delayed than cardiac action. Suppression of cardiac output may account for the early phase of the antihypertensive effect of $\beta_1$-AS-ODN, whereas the inhibition of renin-angiotensin activity acts as the secondary mechanism underlying the sustained reduction of blood pressure in SHR.

Receptor binding assay showed that $\beta_1$-AS-ODN reduced the $\beta_1$-AR levels in renal cortex by ≈30% for 18 days. This is consistent with the decrease of $\beta_1$-AR in heart ventricles in magnitude and time course. This suggests that $\beta_1$-AS-ODN delivered by cationic liposomes is rapidly transported to peripheral organs after intravenous injection and effectively taken up into heart and kidney cells to a comparable extent. Several mechanisms have been proposed for the AS-ODN inhibition of the expression of target proteins. One involves the decrease in mRNA levels resulting from RNase H digestion of the RNA strand of the RNA-DNA duplex (Phillips et al., 1996 and Phillips et al., 1997). To test this hypothesis, a pair of primers that flanked the AUG start codon of $\beta_1$-AR mRNA were designed where AS-ODN bound to perform semiquantitative RT-PCR™. As shown in the Results, there was no reduction in the RT-PCR™ products, indicating the absence of RNase H action. Therefore, the inhibition of $\beta_1$-AR expression probably occurs in post-transcriptional steps.

By decreasing $\beta_1$-AR levels in kidney, $\beta_1$-AS-ODN significantly reduced PRA and the subsequent plasma Ang II levels. This is unlikely to be through the inhibition of renin expression, however, because there is no long-term diminution of renin mRNA levels. Instead, $\beta_1$-AS-ODN may exert its inhibitory impact on renin secretion or the conversion of inactive renin to active renin. This hypothesis is consistent with the observation that $\beta$-adrenergic stimulation of renin expression had a time course different from that of renin secretion (Holmer et al., 1997 and Chen et al., 1993). Furthermore, $\beta$-blockers have been shown to reduce prorenin processing to active renin without changing total renin (prorenin+PRA) levels in plasma (Blumenfeld et al., 1999).

Efficient gene delivery is vital to the therapeutic application of AS-ODN in vivo. Among nonviral vectors, cationic liposomes are the most widely used. They are safe, nonimmunogenic, and east to produce on a large scale. However relatively low transfection efficiency has been obtained after intravenous administration, mainly because of the inactivation of cationic liposome by serum. It was recently shown that increasing the charge ratio (±) of liposome to DNA and inducing the maturation of liposome-DNA complex by prolonging incubation time can overcome this problem (Yang et al., 1997; 1998). The optimal charge ratio of DOTAP:DNA was demonstrated to be ≈2 (Yang et al., 1997 and Templeton et al., 1997). Thus, 5 charge ratios were tested ranging from 0 to 3.5 to optimize the AS-ODN delivery. As shown in the results, increasing the charge ratio not only improved the delivery efficiency but also prolonged the duration of $\beta_1$-AS-ODN action. The best antihypertensive result (−35 mm Hg for 33 days) was consistently achieved at ratio 2.5.

In summary, $\beta_1$-AS-ODN delivered with cationic liposomes at a single intravenous injection achieves a marked and sustained hypotensive effect (30 to 35 mm Hg for 33 days) in SHR. The $\beta_1$-AS-ODN is clearly longer lasting than any current drug, does not inhibit $\beta_2$-adrenergic receptors or cross the blood-brain barrier, and has negligible effect on heart rate. Therefore, the antisense is likely to have fewer side effects than currently used $\beta$-blockers. Inhibition of cardiac contractility initially followed by reduced renin release is an important mechanism contributing to its antihypertensive effects.

5.3 EXAMPLE 3

Treatment of Hypertension Using Antisense Compounds 5.3.1 Materials and Methods 5.3.1.1 Antisense Design and Administration AS-ODN and inverted-ODN control were 15 mer and targeted to the AUG start codon of rat $\beta_1$-adrenoceptor mRNA (Machida et al., 1990). The sequence of AS-ODN was 5'-CCGCGCCCATGCCGA-3' (SEQ ID NO:1), and the sequence of the inverted-ODN was 5'-AGCCGTACCCGCGCC-3' (SEQ ID NO:138). This AS-ODN was chosen from six AS candidates targeted to different regions of $\beta_1$-adrenoceptor mRNA, based on the intensity of cardiac $\beta_1$-AR inhibition and reduction of blood pressure in SHR. These oligonucleotides were modified by backbone phosphorothioation. ODNs delivered with cationic liposomes were injected into tongue vein.

5.3.1.2 Preparation of Liposomes and ODN/Liposome Complex

The cationic lipid 1,2-bis(oleoyloxy)-3-(trimethylammonio)propane (DOTAP) was mixed with a helper lipid L-α dioleoyl phosphatidylethanolamine (DOPE, Avanti Polar Lipids) at 1:1 mole ratio, briefly sonicated and stored at 4° C. until use. The average diameter of liposome is 200–350 nm (Tang and Hughes, 1998). ODN/liposome complex was prepared on the day of use by mixing desired amounts of ODNs with DOTAP/DOPE to the final DNA concentration of 300 μg/ml in 5% (wt./vol.) dextrose in water and incubating at room temperature for 60 min. Two DNA/lipid mole ratios, i.e., 1:0.5 and 1:2.5, were used in each study.

5.3.1.3 Animal Surgery

Adult male SHRs (250–350 g, Harlan) were kept in cages in a room with a 12-hr light-dark cycle. Animals were fed standard laboratory rat chow and tap water ad libitum.

5.3.1.4 Telemetric Sensor Implanation

Before implantation, the zero of each radiotransmitter (TA11PA-C40, Data Sciences) was verified to be ≦4 mm Hg. SHR were anesthetized with 100 mg/kg ketamine and 15 mg/kg xylazine and a midline abdominal incision was made. A fluid-filled catheter was then inserted into the right femoral artery and the tip of the catheter was in the abdominal aorta caudal to the renal arteries. The implanted rats were allowed to recover for one week.

5.3.1.5 Jugular Vein Cannulation

One week after telemetric implantation, rats were anesthetized and a curved catheter made of PE 50 and vinyl tubing was inserted into the external branch of the jugular vein. The tubing was led under the skin of the neck and exposed on the back to allow for drug infusion. Rats were allowed to recover for 24 hr before experimentation. The catheters were flushed with 100 U heparin every day to prevent clogging.

5.3.1.6 Membrane Preparation and $\beta$-AR Binding Assay

Four days after intravenous injection of saline (n=6) or 1 mg/kg inverted ODN (n=6), or 2, 4, 10, 18 days after injection of 1 mg/kg $\beta_1$-AS-ODN (n=24), animals were sacrificed and membranes were prepared from heart ventricles as previously described (Baker and Pitha, 1982). For saturation studies, 100 μg membrane protein was incubated in triplicate with six concentrations of $^{125}$I-(−)iodocyanopindolol (I-CYP, NEN Life Science, 6.25–100 pM) in a total volume of 250 μl containing 50 mM Tris-HCl (pH 7.4), 5 mM MgCl$_2$ at 36° C. for 60 min. The nonspecific and $\beta_2$-adrenoceptor binding levels were determined in the presence of 1 μM (±)-alprenolol and 150 nM CGP20712A (RBI), respectively. Then the reaction mixture was passed through Whatman GF/B glass fiber filter using Brandel harvester and the bound radioactivity was counted for one min.

5.3.1.7 Tissue Preparation and Quantitative Autoradiography

Four days after injection of 1 mg/kg $\beta_1$-AS-ODN (n=6) or saline (n=6), rats were sacrificed and tissues were removed and frozen in dry ice. Coronal sections of brain, horizontal sections of heart and sagittal sections of kidney (20 μm) were cut on a cryostat (Microm) at −20° C. and mounted on microscope slides. Every seventh slide was stained with haematoxylin and eosin for histology. Tissue sections were preincubated in Krebs buffer (NaCl 118.4 mM, KCl 4.7 mM, MgSO$_4$ 1.2 mM, CaCl$_2$ 1.27 mM, NaH$_2$PO$_4$ 10.0 mM, pH 7.1) containing 0.1 mM guanosine triphosphate (GTP), 0.1 mM ascorbic acid and 10 μM phenylmethylsulfonylfluoride (PMSF) for 30 min at 25° C. Sections were then incubated in Krebs buffer containing 0.1 mM ascorbic acid and 10 μM PMSF with 100 pM I-CYP at 25° C. for 150 min, in the presence of 1 μM (−)propranolol, 100 nM IC1118,551 ($\beta_2$-selective antagonist) or 100 nM CGP20712A ($\beta_1$-selective antagonist) to distinguish non-specific, $\beta_1$- and $\beta_2$-bindings. Labeled sections were rinsed in the same buffer, followed by two 15-min washes at 37° C. in the buffer and rinsed in distilled water at 25° C. (Matthews et al., 1994). Dried sections were then exposed to X-ray films (Kodak Biomax-MR). The images were quantitated with a computerized image analysis system (MCID, Imaging Research) and normalized using $^{125}$I-standards. Non-specific binding was less than 10% of total binding.

5.3.1.8 Determination of Effects of $\beta_1$-AS and Atenolol on Cardiovascular Parameters in Response to $\beta$-STIMULATION 5.3.1.8.1 Langendorff Heart Perfusion Forty-eight hr after injection of 1 mg/kg $\beta_1$-AS-ODN (n=9) or inverted-ODN (n=6), SHR were anesthetized and sacrificed. Hearts were quickly removed and perfused via the aorta with oxygenated Krebs buffer (118 mM NaCl, 18.75 mM NaHCO$_3$, 1.2 mM KH$_2$PO$_4$, 4.7 mM KCl, 1.2 mM MgSO$_4$, 1.25 mM CaCl$_2$, 11.1 mM Glucose, 0.01 mM EDTA) at a constant flow of 7.0 ml/min at 36° C. Coronary perfusion pressure (CPP) was measured via a catheter placed proximal to the aorta and connected to a pressure transducer (Gould Statham P23ID). A latex balloon filled with water and connected to the pressure transducer was inserted into the left ventricle through the left atrium to measure left ventricular end-diastolic pressure (LVEDP), left ventricular systolic pressure (LVSP), and developed left ventricular pressure (dLVP) (dLVP=LVSP−LVEDP). LVEDP during equilibration was set at 5 to 7 mmHg. CPP, LVEDP and LVSP were continuously recorded on a 4-channel recorder (Astro-Med). After baselines for dLVP and heart rate (HR) were stable for 5 min, isoproterenol (ISO, non-specific β-agonist) was given at 0.01, 0.025, 0.05, 0.12 μM at 10-min intervals so as to avoid the effect of tachyphylaxis.

5.3.1.8.2 Telemetric Monitoring of Live Animals

The effects of $\beta_1$-AS-ODN and atenolol on cardiac dP/dt$_{max}$, HR and systolic blood pressure (SBP) were compared in the same group of SHR (n=4). Two days after catheterization of jugular vein, control values were taken and 1 mg/kg $\beta_1$-AS-ODN was injected. Forty-eight hr later, rats were tested for the effect of $\beta_1$-AS-ODN. The rats were allowed to recover until all the cardiovascular parameters returned to control values. Then 1 mg/kg atenolol ($\beta_1$-selective antagonist) was injected and rats were tested 30 min later. For $\beta_1$-stimulation, SHR were infused with dobutamine ($\beta_1$-selective agonist) through jugular vein catheter at 5, 10, 20, 40 μg/kg/min. Each dose was given for 5 min continuously and at 1-hr intervals until all cardiovascular parameters returned to baseline so as to avoid the effect of tachyphylaxis. BP and HR were sampled every min. dP/dt$_{max}$ was calculated from the slope of the rising pulse pressure curve and determined every min. The difference between values at each dose and baseline was denoted as Δ.

5.3.1.9 Blood Pressure Monitoring 5.3.1.9.1 Telemetry

Each rat cage was placed on a receiver (RLA1020, Data Sciences) for measurement of cardiovascular parameters. Data were collected with a computer-based data acquisition program (Dataquest LabPRO3.0; Data Sciences). BP and HR were measured every 10 min and averaged every 1 to 24 hr. Before treatment, SHR were monitored for a week to get a stable baseline.

5.3.1.9.2 Tailcuff

Rats were warmed for 20–30 min in cages on heating pads. The temperature was controlled at 35–37° C. Then rats were placed in a plastic restrainer kept at 37° C. A pneumatic pulse sensor was attached to the tail. After cuff inflation, SBP was determined as the first pulsatile oscillation on the descending side of pressure curve. HR was determined by manual counting of pulse numbers per unit time. BP and HR were recorded by a Narco physiograph. Data values of each rat were taken as an average of at least four stable readings. Baseline was determined by averaging three days of measurements before antisense administration.

5.3.1.10 Statistic Analysis

Values were expressed as mean±SEM. Difference was considered statistically significant at P<0.05. Unpaired t-test was used to compare B$_{max}$, dLVP and BP in two groups. One way repeated ANOVA and Tukey test were used to compare ΔdP/dt and ΔHR upon dobutamine infusion in different groups. Pearson product moment correlation was used to assess the relationship between $\beta_1$-adrenoceptor B$_{max}$ and dLVP.

5.3.2 Results 5.3.2.1 Effect on Cardiac β-Adrenoceptor Density

A single intravenous injection of 1 mg/kg $\beta_1$-AS-ODN delivered with cationic liposomes at a 1:2.5 mole ratio significantly reduced the $\beta_1$-adrenoceptor densities in the SHR hearts for 18 days (P<0.01). The drop was at its maximum of 47% on day 4, 33% on day 10, and maintained at 29% on day 18. In contrast, there was no significant change in the B$_{max}$ of $\beta_2$-adrenoceptors. K$_D$ of both subtypes remained unaltered (Table 5). Consequently, the $\beta_1/\beta_2$ subtype ratio in the ventricles was diminished from ~70/30 to ~50/50 by $\beta_1$-AS-ODN. Inverted-ODN had no effect on either subtype.

TABLE 5

B$_{MAX}$ AND K$_D$ OF $\beta_1$- AND $\beta_2$-ADRENOCEPTORS IN CARDIAC VENTRICLES OF SHR 4 DAYS AFTER TREATMENT WITH SALINE, INVERTED-ODN OR $\beta_1$-AS-ODN

| | Total ($\beta_1 + \beta_2$) | | $\beta_1$ | | $\beta_2$ | |
|---|---|---|---|---|---|---|
| | K$_D$ (pM) | B$_{max}$ (fmol/mg) | K$_D$ (pM) | B$_{max}$ (fmol/mg) | K$_D$ (pM) | B$_{max}$ (fmol/mg) |
| Saline | 55.4 ± 6.7 | 27.6 ± 0.9 | 64.7 ± 5.4 | 18.7 ± 0.9 | 29.6 ± 0.5 | 9.1 ± 0.6 |
| Inverted-ODN | 57.1 ± 3.5 | 26.3 ± 3.0 | 66.0 ± 1.0 | 18.1 ± 2.3 | 32.0 ± 2.4 | 8.7 ± 0.5 |
| $\beta_1$-AS-ODN | 37.0 ± 1.0* | 19.8 ± 1.8* | 60.5 ± 3.4* | 10.0 ± 1.2* | 30.7 ± 3.3 | 9.9 ± 0.5 |

Data represent mean ± SEM of each group (N = 6–10). *P < 0.01 versus saline control.

5.3.2.2 Effect on Cardiac Contractility and Heart Rate in Response to β-Stimulation Forty-eight hr after injection of 1 mg/kg $\beta_1$-AS-ODN, the cardiac inotropic and chronotropic responses to β-stimulation were determined in SHR in vitro and in vivo.

First, isolated hearts were perfused with incrementing doses of ISO, which enhanced heart rate and contractility via activating β-adrenoceptors. The dLVP-ISO dose-response curve, which reflected the positive inotropic effect of ISO, was significantly shifted down by $\beta_1$-AS-ODN (P<0.02). Heart rate was not significantly decreased.

In vivo test was performed in conscious SHR monitored by radiotelemetry. $\beta_1$-AS-ODN significantly (P<0.02) dampened the increase in dP/dt$_{max}$, in the face of dobutamine ($\beta_1$-selective agonist). The change in heart rate was not significantly reduced, which echoed the results in isolated, perfused hearts. On the other hand, the response of blood pressure to dobutamine was biphasic. Dobutamine elevated SBP by 5–8 mmHg at low infusion speed and reduced SPB at higher speed. This is probably due to the partial $\beta_2$-argonistic activity of dobutamine at high doses and the consequent vasodilatory effect on blood pressure. Relative to $\beta_1$-AS-ODN, 1 mg/kg atenolol produced a more profound decline in ΔdP/dt$_{max}$ and ΔHR during a 5-hr period of time after injection. Moreover, it reduced the resting dP/dt$_{max}$ (2450±295 mmHg/sec versus control 2937±277 mmHg/sec) and caused bradycardia (295±12 bpm versus control 365±8 bpm) (P<0.05), while $\beta_1$-AS did not change resting contractility (2922±249 mmHg/sec) or heart rate (365±12 bpm). But the effects of atenolol on ΔdP/dt$_{max}$ and ΔHR were transient. Within 24 hr after atenolol administration, the inotropic and chronotropic effects of dobutamine had returned to control level.

5.3.2.3 Effect on blood Pressure of SHR

The effects of single injection of 1 mg/kg $\beta_1$-AS-ODN on blood pressure of SHR measured by tailcuff method were observed. AS-ODN was delivered with cationic liposome at different mole ratios of DNA/lipid, ie., 1:0.5 and 1:2.5. $\beta_1$-AS-ODN delivered with liposomes at 1:0.5 ratio diminished SBP for 8 days. The maximum drop was 38±5 mmHg. When the mole ratio was increased to 1:2.5, this hypotensive effect was drastically prolonged to 20 days. No effect was seen with inverted-ODN.

In order to compare the effects of $\beta_1$-AS-ODN and atenolol, radiotelemetry was used to monitor blood pressure and heart rate on a regular basis. One mg/kg $\beta_1$-AS-ODN delivered with liposomes at a 1:0.5 ratio produced a maximum drop of 15 mmHg in mean blood pressure. The antihypertensive effect lasted for 8 days, which was consistent with the results measured with tailcuff. Heart rate was not significantly altered. In contrast to AS-ODN, although the onset of hypotensive effect caused by 1 mg/kg atenolol occurred as early as 20 min after injection, it lasted for only 10 hr. In addition, atenolol caused considerable bradycardia up to an average of −75 bpm.

5.3.2.4 Effect on β-Adrenoceptor Distribution in Brain, Heart and Kidney

Quantitative autoradiography of 6–18 tissue slices in brain, heart and kidney was analyzed four days after intravenous $\beta_1$-AS-ODN administration. No changes in the distribution of β-adrenoceptors in forebrain and brainstem regions were detected. This indicated the absence of antisense effect on the β-adrenoceptor expression in CNS. However, $\beta_1$-AS-ODN significantly (P<0.05) reduced $\beta_1$-adrenoceptor densities in cardiac ventricles (from 30.2±2.1 to 20.6±2.5 fmol/mg) and renal cortex (26.4±3.1 to 17.4±3.3 fmol/mg). This was consistent with the binding results. $\beta_2$-adrenoceptors were not affected in any tissues.

5.3.3 Summary

This example demonstrates the effects of $\beta_1$-AS-ODN compositions on high blood pressure in a model of hypertension as compared to using a traditional β-blocker modality. $\beta_1$-AS-ODNs knocked down $\beta_1$-adrenergic activity, resulting in long-term attenuation of blood pressure. The results indicated that $\beta_1$-AS-ODN reduced $\beta_1$-adrenoceptor density and cardiac contractility following $\beta_1$-stimulation in vitro and in vivo and lowered high blood pressure of SHR. These findings are consistent with the hypothesis that $\beta_1$-AS, through the inhibition of $\beta_1$-adrenoceptor expression, is able to render heart, kidney and other tissues less sensitive to sympathetic activation, which is a major contributing factor in high blood pressure. A single injection of $\beta_1$-AS-ODN effectively decreased the cardiac $\beta_1$-adrenoceptor density, which was accompanied by diminished ventricular contractility and cardiac output in response to β-stimulation. The antihypertensive effect in SHR was up to a 38-mmHg reduction lasting as long as 20 days.

Treatment of $\beta_1$-AS-ODN reduced cardiac $\beta_1$-adrenoceptor density by ~50% in four days. There is considerable variation reported in the literature on the half-life of $\beta_1$-adrenoceptors (Baker and Pitha, 1982; Neve and Molinoff, 1986; Winter et al., 1988). From the results with the AS-ODN inhibition, it appears that the half-life of cardiac $\beta_1$-adrenoceptor is approximately 2–4 days to allow for 50% reduction of β-adrenoceptor density within 4 days.

Both tailcuff and telemetry measures of blood pressure showed a significant drop after antisense treatment. SHR responded to $\beta_1$-AS-ODN to a greater degree of hypotension when subjected to tailcuff versus telemetry. In addition, the baseline measured with tailcuff was consistently higher than that with telemetry by 20–30 mmHg in the same rats. Bazil et al. (1993) reported a similar phenomenon. They compared the cardiovascular parameters recorded by telemetry, tailcuff and arterial catheter and observed a more sensitive hypotensive effect of captopril with tailcuff. Tailcuff measurement of blood pressure involves warming and restraint of rats. It is conceivable that $\beta_1$-AS, through the suppression of sympathetic activity, can decrease blood pressure of animals under stress more effectively.

Cationic liposomes are effective vehicles for gene delivery. It has been shown that liposome entrapment not only improves the cellular uptake of DNA, but also protects DNA from degradation and extends its circulation time (Allen, 1997; Liu et al., 1997). Numerous factors influence the efficiency of cationic liposome-mediated intravenous gene delivery, such as DNA/lipid ratio, selection of lipids and preparation procedure (Liu et al., 1997; Yang and Huang, 1998). A widely used lipid formula DOTAP/DOPE was used to deliver $\beta_1$-AS-ODN at four mole ratios (1:0.5, 1:1.5, 1:2.5, and 1:3.5). The optimal ratio 1:2.5 was determined based on the duration and magnitude of the antihypertensive effects. A profound and prolonged fall in blood pressure of 38 mmHg up to 20 days was achieved at this ratio, which followed the reduction in $\beta_1$-adrenoceptor binding to a maximum of 47% at day 4, 33% at day 10, and 29% at day 18. This implies that $\beta_1$-AS-ODN effectively inhibits the functionally active receptors involved in the blood pressure.

The blood-brain barrier formed by capillary endothelia is only permeable to small lipophilic molecules with molecular weight <600 Da (Padridge, 1998). Owing to their high hydrophilicity, ODNs undergo negligible transport through blood-brain barrier and have very limited access to CNS (Agrawal et al., 1991). The cellular and organ distributions of DNA/liposome complexes with fluorescent labeling were previously studied in mice after intravenous injection and the results indicated that the complexes were primarily taken up by capillary endothelial cells in most of the peripheral organs including lung, heart, kidney and spleen, but absent in the brain (McLean et al., 1997). Although the brain retention of liposomes after peripheral administration was observed in some cases, it is due to entrapment within the brain microvasculature (Schackert et al., 1989). In this study, autoradiography in brain revealed no detectable changes in the expression and distribution of β-adrenoceptors after intravenous $\beta_1$-AS-ODN injection. This provided further evidence that an antisense modality does not produce CNS effects.

High specificity based on gene sequence has made antisense an increasingly useful tool in numerous studies and clinical trials. Its success is manifested by the recent approval of the first antisense drug Vitrovene by FDA. In the present study, $\beta_1$-AS-ODN inhibited $\beta_1$-AR expression without changing $\beta_2$-adrenoceptors, demonstrating a specificity of the $\beta_1$-AS-ODN selected sequences.

In patients with chronic heart failure, the severity of the disease closely relates to the decrease in cardiac β-AR density and functional responsiveness (Brown et al., 1992). In SHR treated with $\beta_1$-AS-ODN, a marked attenuation of the $\beta_1$-adrenoceptor-mediated positive inotropic response was observed in vitro and in vivo, concurrent with the diminished cardiac $\beta_1$-AR level. Therefore, these results indicated a positive correlation between cardiac $\beta_1$-AR number and functional sensitivity (correlation coefficiency >0.90, P<0.01).

Despite the large decrease in blood pressure, no reflex tachycardia was observed after antisense treatment. However, the suppressive effect of $\beta_1$-AS-ODN on heart rate was less significant than its negative inotropic response. The reason for this is still under investigation. Several possibilities can be considered. First, $\beta_1$-AS-ODN did not affect $\beta_2$-adrenoceptors, which played an important role in the regulation of heart rate (Kaumann, 1986; Rodefeld et al., 1996), while not involved in the cardiac contraction. Second, antisense inhibition of $\beta_1$-AR expression is gradual and to a lesser extent than β-blockers. It is also possible that $\beta_1$-ARs may have a larger reserve for controlling heart rate than contractility. Finally, evidence suggests that cardiomyocytes preferentially take up AS-ODN while pacemaker cells are less efficient.

The cardiovascular effects of $\beta_1$-AS-ODN were compared with a hydrophilic $\beta_1$-selective antagonist, atenolol. $\beta_1$-AS-ODN showed advantages over atenolol in reducing blood pressure and maintaining normal heart rate. Although the onset of $\beta_1$-AS-ODN action was slower than atenolol, it lasted much longer, 20 days compared to less than 1 day with atenolol. Furthermore, $\beta_1$-AS-ODN did not affect heart. rate, while atenolol caused appreciable bradycardia. Bradycardia is a common complaint by patients taking this drug. Atenolol also reduced resting ventricular contractility and heart rate and thereby reduced resting cardiac output. $\beta_1$-AS-ODN is unlikely to alter resting cardiac performance. The results presented here suggest that $\beta_1$-AS-ODN offer a significant improvement over currently used β-blockers, in both prolonged blood pressure reduction and absence of effects on $\beta_2$-adrenoceptors and CNS.

5.4 Example 4

Protection Against Myocardial Ischemia-Reperfusion-Induced Cardiac Dysfunction by Antisense Compositions Directed at $\beta_1$-AR mRNA Acute myocardial ischemia causes significant increase in plasma catecholamine levels, which leads to exacerbation of the ischemic myocardial injury (Waldenstrom et al., 1978; Rona, 1985). The worsening myocardial ischemia is an important factor in cardiac dysfunction. Acute myocardial ischemia is also characterized by increased sensitivity of $\beta_1$-ARs in the myocardium during acute ischemia (Strassere et al., 1990). β-ARs form the interface between the sympathetic nervous system and the cardiovascular system (Strassere et al., 1990; Mukherjee et al., 1979; Maisel et al., 1985. Importantly, $\beta_1$-AR subtype 1 ($\beta_1$-AR) is by far the predominant β-AR in myocardium (Minneman et al., 1995) and its activity and sensitivity are believed to regulate cardiac function via adenylyl cyclase activity (Mukherjee et al., 1979; Thandroyen et al., 1986; Böhm, 1995). Several studies have shown that density of $\beta_1$-AR increases and the expression of $\beta_1$-AR mRNA is augmented in the myocardium after acute ischemia (Maisel et al., 1985; Karliner et al., 1989; Ihl-Vahl et al., 1995). Experimental and clinical results have also demonstrated that β-AR blockade, especially selective blockade of $\beta_1$-AR, can protect myocardium against ischemic injury and cardiac dysfunction (Schulz et al., 1995; Ablad et al., 1987; Lu et al, 1990), decrease infarct size (Schulz et al., 1995), and reduce the incidence of sudden cardiac death in patients with myocardial infarction (Yusuf et al., 1985).

Although chemical β-AR blockers are commonly used in the treatment of ischemic heart disease, these agents often cause central nervous system side effects and $\beta_2$-AR antagonistic activity is associated with increase in peripheral vascular resistance. Development of antisense-oligodeoxynucleotides (AS-ODNs) against specific receptor mRNA is a novel approach to decrease the synthesis of receptor proteins (Phillips et al., 1996; Dachs et al., 1997). This approach has potential to be of therapeutic benefit in disease states characterized by upregulation of these receptors (Phillips et al., 1996; Dachs et al., 1997; Yang et al., 1998). A recent study indicated that AS-ODNs directed at angiotensin II type 1 receptors ($AT_1$) decrease the synthesis of $AT_1$ receptor protein and protects the ischemic rat heart from the adverse effects of ischemia (Yang et al., 1998). As demonstrated herein, a single intravenous injection of an antisense compositions directed against $\beta_1$-AR mRNA can reduce blood pressure in SHR for periods of at least 20 days (Zhang et al., 1999).

In this example, the effect of AS-ODNs on lipid peroxidation was examined. Also examined were their effects on the expression of $\beta_1$-AR protein and mRNA in the myocardium after ischemia-reperfusion.

5.4.1 Materials and Methods

5.4.1.1 Antisense Compositions and Liposomal Formulations

AS-ODNs and inverted-oligodeoxynucleotides (IN-ODNs) control were 15-mers and targeted to −5 to +10 of rat $\beta_1$-AR mRNA encompassing the AUG start colon. The sequence of AS-ODNs was 5'-CCGCGCCCATGCCGA-3' (SEQ ID NO:1), and the corresponding IN-ODNs was 5'-AGCCGTACCCGCGCC-3' (SEQ ID NO:138) (Zhang et al., 1999). These ODNs were modified by backbone phosphorothioation and synthesized in the DNA Synthesis Core Laboratory of the University of Florida.

Since cationic liposomes enhance the uptake of DNA by cells and also protect DNA from degradation and extend its circulation time, DOTAP/DOPE (mole:mole=1:1) liposomes were used to deliver the antisense compositions to host animals. The average diameter of liposomes was 200–300 nm. ODNs/liposomes complex was prepared on the day of use by mixing desired amount of ODNs with DOTAP/DOPE to final DNA concentration of 300 μg/ml in 5% (wt./wt.) dextrose in water and incubating at room temperature for 60 min (Yang et al., 1998; Zhang et al., 1999).

5.4.1.2 Animals

Male Sprague-Dawley rats weighing 200–250 g were injected intravenously with either AS-ODNs (n=7) or IN-ODNs (n=7) at a dose of 200 μg/rat 4 days before excising the hearts. DOTAP/DOPE liposomes (700 μg/rat) were given along with ODNs. Parallel groups of rats were treated with saline (n=13), or the selective $\beta_1$-AR blocker atenolol 2 mg/kg (n=7) 6 hr before the hearts were excised.

5.4.1.3 Isolated Perfused Heart Model

Four days after administration of AS-ODNs or IN-ODNs or 6 hr after administration of atenolol or saline, rats were anesthetized with sodium pentobarbital (40 mg/kg) intraperioneally. The hearts were excised rapidly and placed in ice-cold Kreb-Henseleit buffer (mmol/L: NaCl 118, KCl 4.7, $KH_2PO_4$ 1.2, $MgSO_4$ 1.2, $CaCl_2$ 1.25, $NaHCO_3$ 25, and glucose 11, pH 7.4). Within one min, the hearts were transferred to an isolated perfusion apparatus and perfused via the aorta with oxygen-saturated (95% $O_2$+5% $CO_2$) Kreb-Henseleit buffer kept at 37° C. with the use of a MasterFlex pump (model 7015-21, Cole-Palmer Instrument Co.) according to the modified Langendroff procedure (Yang et al., 1998; Neely and Rovetto, 1975). The heart was placed in a semi-closed circulating water-warmed (37° C.) air chamber, paced atrially with a Medtronic 5320 pacemaker at a rate of 300 bpm, and perfused at a constant flow (5.5–6.0 ml/per min). Coronary perfusion pressure (CPP) was measured via a catheter placed just proximal to the aorta and connected to a Gould Statham P23ID pressure transducer. A latex balloon filled with water and connected to a Gould Statham P23ID pressure transducer was inserted in the left ventricle through the left atrium to measure left ventricular end-diastolic pressure (LVEDP), left ventricular systolic pressure (LVSP), and developed left ventricular pressure (dLVP) (dLVP=LVSP–LVEDP). LVEDP during equilibration was set at 5 to 7 mmHg. All measurements were continuously recorded on a 4-channel record (Astro-Med).

5.4.1.4 Myocardial Ischemia and Reperfusion

Six hearts from saline-treated rats were continuously perfused with Kreb-Henseleit buffer for 80 min and served as sham control. Hearts from other rats, after 20 min of equilibration, were subjected to 30 min of ischemia followed by 30 min of reperfusion. After completion of the study, hearts were frozen in liquid-nitrogen for $\beta_1$-AR analysis by binding assay, $\beta_1$-AR protein analyses by Western blot, $\beta_1$-AR mRNA analysis by reverse transcription-polymerase chain reaction (RT-PCR™), and measurement of MDA.

5.4.1.5 Determination of $\beta_1$-AR Density in Myocardium

Membrane protein was prepared from left ventricles as previously described (Baker and Pitha, 1982). For saturation studies, 100 $\mu$g membrane protein was incubated in triplicate with $^{125}$I-(–)iodocyanopindolol (I-CYP, NEN Life Science, 6.25–100 pM) in a total volume of 250 $\mu$l containing 50 mM Tris-HCl (pH 7.4), 5 mM MgCl$_2$ at 36° C. for 60 min. The nonspecific and $\beta_2$-adrenoceptor binding were determined in the presence of 1 $\mu$M (±)-alprenolol and 150 mM CGP207ASA (RBI), respectively. Then the reaction mixture was passed through Whatman GF/B glass filter using Brandel harvester and the radioactivity was counted for one min.

5.4.1.6 Quantification of $\beta_1$-AR Protein Expression in Myocardium

Myocardial tissues were homogenized and lysed in boiling lysis buffer (1% SDS, 0.1% Triton X-100®, and 10 mmol/L Tris-HCl, pH 7.4) and centrifuged at 10,000 RPM for 30 minutes at 4° C. The lysate protein from myocardial tissues (20 $\mu$g/lane) was separated by 8% SDS-PAGE using a Bio-Rad Mini-Protean cell, transferred to nitrocellulose membrane (Amersham). After incubation in blocking solution (4% non-fat milk, Sigma), membranes were incubated with 1:1000 dilation primary antibody (polycolonal antibody to $\beta_1$-AR, Santa Cruz Biotechnology) for overnight at 4° C. Membranes were washed and incubated with 1:2000 dilution second antibody (Amersham) for one hr. The membranes were detected with the ECL system, as described previously (Yang et al, 1998; Li et al., 1999).

5.4.1.7 Determination of $\beta_1$-AR mRNA

Total RNA was isolated from rat myocardium with the single step acid-guanidinum thiocyanate-phenol-chloroform method and quantified (Chomcznski and Sacchi, 1987). One $\mu$g of total RNA was reverse transcribed with oligo-dT (Promega) and M-MLV reverse transcriptase (Promega) at 37° C. for one hr. 1.5 $\mu$l of RT material was amplified with Taq DNA polymerase (Promega) using a primer pair specific to $\beta_1$-AR:

Forward primer: 5'-CTCCGAAGCTCGGCATGG-3' (SEQ ID NO:139); and

Reverse primer: 5'-GCACGTCTACCGAAGTCCAGA-3' (SEQ ID NO:140).

PCR™ product was 432 base pairs. For PCR, 35 cycles were used at 95° C. for one minute, 60° C. for one minute, and 72° C. for one min. The RT-PCR™ amplified samples were visualized on 1.8% agarose gels using ethidium bromide. A primer pair of rat GAPDH was used as control:

Forward primer: 5'-ATCAAATGGGGTGCTGGTGCTG-3' (SEQ ID NO:141); and

Reverse primer: 5'-CAGGTTTCTCCAGGCGGCATGTCA-3' (SEQ ID NO:142).

For PCR™, 35 cycles were used at 95° C. for one min, 60° C. for one min, 72° C. for one min. PCR™ product was 504 base pairs. Relative intensity of bands of interest were analyzed by NSF-300G Scanner (Microtek) (Yang et al., 1998; Li et al., 1999).

5.4.1.8 Determination of MDA Levels in Myocardium

Malondialdehyde (MDA) levels in myocardium were measured in duplicate by a modification of the method of Ohkawa et al., (1979). Briefly, the ventricular tissues were homogenized. The assay mixture consisted of 0.1 ml of the tissue homogenate, 0.4 ml of 0.9% NaCl, 0.5 ml of 3% sodium dodecylsulfate, 3 ml of TBA (thiobarbituric acid reagent, containing equal parts of 0.8% aqueous thiobarbituric acid and acetic acid) and was heated for 75 min at 95° C. Thereafter, 1 ml cold 0.9% NaCl was added to the mixture, which was cooled and extracted with 5 ml n-butanol. After centrifugation at 3,000 rpm for 15 min, the butanol phase was assayed spectrophotometrically at 532 nm. Tetramethoxypropane (in amounts of 0, 0.1, 0.2, 0.4, 0.8, 1.0 nmole) served as external standard. MDA levels in myocardium were expressed in $\mu$mol/g tissue.

5.4.1.9 Data Analysis

Data was presented as mean±SD. Statistical significance was determined in multiple comparisons among independent groups of data in which ANOVA and the Student-Newman-Keuls test indicated the presence of significant differences. A P value of $\leq 0.05$ was considered statistically significant.

5.4.2 Results 5.4.2.1 Cardiac Dysfunction During Ischemia-Reperfusion

The basal values of CPP, LVSP, LVEDP, and dLVP were similar in all groups of rat hearts. In the control continuously buffer-perfused hearts observed for 80 min, there were only minimal (~5%) changes in the indexes of cardiac fiction. In the hearts from saline-treated rats, 30 min of ischemia followed by 30 min of reperfusion resulted in marked cardiac dysfunction, indicated by a significant increase in CPP and LVEDP, and a decrease in LVSP and dLVP (all P<0.01, vs. pre-ischemia values).

Treatment of rats with AS-ODNs markedly attenuated the ischemia-reperfusion-induced myocardial dysfunction, indicated by preservation of LVSP and dLVP and minimization of increase in LVEDP and CPP (all P<0.01, vs. saline group). Treatment of rats with atenolol also reduced the increase in CPP and LVEDP induced by ischemia-reperfusion (all P<0.05, vs. saline group, n=7), and modestly attenuated the ischemia-reperfusion-induced change in LVSP and dLVP (P<0.05 vs. saline group, n=7). AS-ODN treatment was more effective than atenolol treatment in preserving dLVP after ischemia-reperfusion (P<0.05). Treatment with IN-ODNs showed no effect on ischemia-reperfusion-induced myocardial dysfunction.

5.4.2.2 MDA Levels in Myocardium

MDA levels in myocardium increased significantly after ischemia-reperfuision (P<0.05 vs. sham control hearts, n=6). Pretreatment of rats with AS-ODNs and atenolol attenuated the increase in MDA levels in the myocardium (both P<0.05 versus saline pretreatment, n=7 each group). As expected, IN-ODNs did not affect MDA levels in myocardium.

5.4.2.3 Change of $\beta_1$-AR Density in Myocardium After Ischemia-Reperfusion

Myocardium from sham control continuously perfused hearts continuously exhibited $\beta_1$-AR and $\beta_2$-AR ($\beta_1$-AR>>$\beta_2$-AR). After ischemia-reperfusion in the saline-treated rat hearts, there was a consistent increase in $\beta_1$-AR density in myocardium ($B_{max}$ 28.7±5.4 vs. 19.6±1.7 fmol/mg in continuously perfused buffer-perfused rat hearts, P<0.05, n=4), while there was no change in $\beta_2$-AR density. Treatment of rats with AS-ODNs resulted in a decrease in $\beta_1$-AR density in the ischemic-reperfused myocardium ($B_{max}$ 15.9±1.3 vs. 28.7±5.4 fmol/mg in saline-treated rat hearts, P<0.05, n=4) while there was no change in $\beta_2$-AR density. Treatment of rats with INV-ODNs or atenolol had no effect on $\beta_1$-AR density in the ischemic-reperfused myocardium.

5.4.2.4 Express of $\beta_1$-AR Protein and mRNA in Myocardium

Western analysis of the control continuously perfused hearts showed a distinct $\beta_1$-AR protein band of 41 kDa. Similar molecular weight band was observed in hearts from saline-, AS-ODNs-, IN-ODNs- and atenolol-treated rat hearts. The $\beta_1$-AR protein band was very dense in the saline-treated rat hearts, including upregulation of the protein during ischemia-reperfusion. Treatment of rats with AS-ODNs abolished the ischemia-reperfusion-mediated increase in $\beta_1$-AR protein expression. Notably, treatment of rats with IN-ODNs or atenolol had no effect on the density of $\beta_1$-AR protein.

Ischemia-reperfusion also resulted in an increase of mRNA for $\beta_1$-AR signal (adjusted for GAPDH signal) by myocardium of saline-treated rats, as determined by RT-PCR. Pretreatment of rats with AS-ODNs attenuated the increase of mRNA for $\beta_1$-AR in myocardium, but mRNA level for $\beta_1$-AR in the myocardium was not significantly affected by treatment of rats with IN-ODNs or atenolol.

5.4.3 Summary

The present example demonstrates the protective role of AS-ODNs directed at $\beta_1$-AR mRNA against cardiac dysfunction after a brief period of ischemia-reperfusion. The study compared the effects of pretreatment of rats with AS-ODNs directed at $\beta_1$-AR mRNA or a selective $\beta_1$-AR blocker atenolol in this process. This study showed that ischemia for 30 min followed by reperfusion for 30 min resulted in a significant cardiac dysfunction and lipid peroxidation in saline-treated rat hearts. Further, ischemia-reperfusion was associated with a marked upregulation of $\beta_1$-AR density and protein and mRNA expression. Pretreatment of rats with atenolol preserved cardiac function, but did not affect the density of $\beta_1$-AR and the expression of $\beta_1$-AR protein and mRNA in the ischemic-reperfused myocardium. Pretreatment of rats with AS-ODNs directed at $\beta_1$-AR mRNA provided almost total preservation of cardiac function and lipid peroxidation following ischemia-reperfusion. AS-ODN treatment also prevented the upregulation of $\beta_1$-AR density, protein and mRNA expression in the ischemic-reperfused myocardium. The effects of AS-ODNs directed at $\beta_1$-AR mRNA on cardiac function were clearly superior to those of the commonly used $\beta_1$-AR blocker atenolol. The effects of AS-ODN on $\beta_1$-AR protein and mRNA expression indicate that its beneficial effects are mediated by inhibition of both transcription and translation of $\beta_1$-AR mRNA.

There is a generalized stimulation of the sympathetic nervous system during ischemia, perhaps a compensatory response designed to preserve cardiac dysfunction. Accordingly, catecholamine levels increase in both plasma and myocardium following myocardial ischemia (Rona, 1985; Richardt et al., 1994; Abrahamsson et al., 1983), but the increased catecholamine concentrations have the potential to contribute to increased excitability of myocardiun resulting in arrhythmia (Strassere et al., 1990; Mukherjee et al., 1979; Maisel et al., 1985; Ohyanahi et al., 1988; Maisel et al., 1987). There is also increase in sensitivity of $\beta_1$-AR during acute myocardial ischemia (Strassere et al., 1990). This coupled with increased circulating and myocardial catecholamine concentrations can exacerbate cardiac injury and dysfunction.

It is generally accepted that activation of $\beta$-AR is the first element in the signal transduction chain mediating sympathetic stimulation of the heart. $\beta_1$-ARs, the dominant $\beta$-AR subtype in the heart (Minneman et al., 1995; Guderman et al., 1995), regulate cardiac function by activating adenylyl cyclase activity (Strassere et al., 1990; Thandroyen et al., 1986; Bohm, 1995). Several experimental studies have indicated an upregulation in $\beta_1$-ARs, but not $\beta_2$-ARs, during acute ischemia-reperfusion (Maisel et al., 1985; Karliner et al., 1989; Persad et al., 1998). Ihl-Vahl et al. (1995) conclusively demonstrated a rapid upregulation of $\beta$-AR mRNA during acute myocardial ischemia; this upregulation is subtype-selective with a specific increase mRNA level for $\beta_1$-ARs, but not for $\beta_2$-ARs. They also showed that the increase of $\beta_1$-AR mRNA is ischemia time-dependent.

Pretreatment of animals with $\beta_1$-AR blockers does not affect the ischemia-reperfusion-induced increase in $\beta_1$-AR mRNA level. This was confirmed in the present study wherein treatment with atenolol did not affect either the $\beta_1$-AR density measured by binding assays or the augmented $\beta_1$-AR protein and mRNA levels measured by Western analysis and RT-PCR, respectively. Other investigators have also shown that $\beta_1$-AR blockers do not block the expression of $\beta_1$-AR protein or mRNA (Aarons and Molinoff, 1982; Heilbrunn et al., 1986; Aarons et al., 1980). In contrast, the present study clearly demonstrates that AS-ODNs directed at $\beta_1$-AR mRNA block the up-regulation of $\beta_1$-AR number, and protein and mRNA levels. The blockade of $\beta_1$-AR at the transcriptional level may be the basis for the superior effect of the AS-ODN approach in the preservation of cardiac function after acute ischemia-reperfusion. Therapy with a single dose of AS-ODNs four days prior to removal of hearts prevented the increase in $\beta_1$-AR protein, which implies sustained inhibitory effects of AS-ODNs at translational levels as well. A previous study in the SHR indeed demonstrated that AS-ODNs against $\beta_1$-AR mRNA decreases $\beta_1$-AR mRNA translation into protein in the hearts for at least up to 18 days (Zhang et al., 1999).

Although chemical $\beta$-AR blockers are effective in the therapy of ischemic heart disease and are widely used in the short- and long-term management of patients with myocardial ischemia, these agents have several undesirable side-effects related to their effects on central nervous system, peripheral vascular resistance, and tracheo-bronchial tree. Even the selective $\beta_1$-AR blockers, such as atenolol, lose their cardio-selectivity at moderate doses. In addition, these agents need to be taken frequently, at least one daily, due to their short half-life. Furthermore, chemical $\beta$-AR blockers do not influence $\beta$-ARs at genomic level. Gene therapy, such as AS-ODNs directed at $\beta_1$-AR mRNA, provides unique benefits. For example, the sequence specific AS-ODNs directed at $\beta_1$-AR mRNA can significantly decrease ventricular $\beta_1$-AR density by 30–50% even after 18 days in the rat after a single intravenous injection (Zhang et al., 1999). The AS-ODNs has no effect on $\beta_2$-AR density. Concurrently, AS-ODN administration is associated with reduction in blood pressure with a 38-mmHg maximum drop without causing bradycardia. Most importantly, there is no effect of AS-ODNs on the distribution of β-ARs in brain. These results demonstrate that a single intravenous injection of AS-ODNs can preserve cardiac dysfunction and protect myocardial injury from ischemia-reperfusion in the rat with specific effects on the expression of mRNA for $β_1$-ARs in myocardium. Importantly, IN-ODNs, used as control for AS-ODNs, did not show any of these effects.

In this study, ischemia-reperfusion-induced cardiac dysfunction was evaluated by the measurement of CPP, LVEDP, LVSP and dLVP. These indices of myocardial dysfunction have been used in several studies in the isolated heart model of global ischemia-reperfusion (Yang et al., 1998; Yang et al., 1993; Yang et al., 1997; Kokita et al., 1998; Ozden et al., 1998). Isolated rat, rabbit or guinea pig heart model provides an inexpensive and reproducible method to evaluate cardiac function and myocardial metabolic alterations during ischemia-reperfusion. This model has been used extensively to study regulation of variety of receptors and modulation of cardiac function by agents acting on different receptors (Lu et al., 1990; Yang et al., 1998; Neely and Rovetto, 1975; Baker and Pitha, 1982; Maisel et al., 1987; Yang et al., 1993; Yang et al., 1997; Kokita et al., 1998; Ozden et al., 1998). In the isolated beating heart, cardiac function can be assessed independent of the influence of circulating blood cells and hormones, which may be considered to provide an important advantage of this model.

MDA, a lipid peroxidation product, has been widely accepted as an index to evaluate myocardial injury after ischemia-reperfuision (Kokita et al., 1998; Ozden et al., 1998). All these parameters were modified by the use of AS-ODNs in the present study. In summary, the present study is the first report on the amelioration of cardiac dysfunction and myocardial injury induced by ischemia-reperfusion in isolated rat heart with a single intra-venous injection of AS-ODNs directed at $β_1$-AR mRNA. This study also provides evidence that the AS-ODNs can block the augmented expression of mRNA for $β_1$-AR in the ischemic myocardium. Lastly, the effects of AS-ODNs directed against $β_1$-AR mRNA appear to be superior to those of atenolol in the isolated rat heart model of ischemia-reperfusion.

5.5 Example 5

Reduction of Cardiac Hypertrophy in Animal Models

Adult spontaneously hypertensive rats (300-350 g) were treated with $β_1$-AS-ODNs for more than 2 months. The blood pressure was reduced by 20–30 mmHg persistently throughout the treatment period (FIG. 11). Control animals receiving saline or INV-ODNs had no change in blood pressure. At the end of a 2-month treatment, the hearts were dissected and weighed. Left ventricular hypertrophy was indicated by the ratio of left ventricle weight to body weight (LV/BW). β1-AS-ODNs significantly reduced left ventricular hypertrophy (P<0.05), compared to controls (FIG. 11).

5.6 Example 6

Attenuation of Cardiac Dysfunction After Myocardial Ischemia-Reperfusion

The protective effects of β1-AS-ODNs were tested in a rat model of myocardial ischemia-reperfusion. Five groups of SD rats were studied. Sham controls (n=6) were injected with saline and perfused continuously for 80 min without ischemia/reperfusion (I/R). In other groups, hearts were perfused for 20 min and subjected to global ischemia (30 min) followed by reperfusion (30 min). Saline+I/R (n=6) or atenolol+I/R (n=7) groups were injected i.v. with saline or 2 mg/kg atenolol 6 hr before the hearts were excised. AS-ODN+I/R (n=7) or INV-ODN+I/R (n=7) were injected iv. with 1 mg/kg $β_1$-AS-ODN or INV-ODN 4 days before the I/R study was performed.

Ischemia-reperfusion resulted in significant cardiac dysfunction, indicated by a significant increase in coronary perfusion pressure (CPP) and left ventricular end-diastolic pressure (LVEDP), and a decrease in developed left ventricular pressure (dLVP) (P<0.01 vs. pre-ischemia values). Treatment with $β_1$-AS-ODN markedly attenuated the ischemia-reperfusion induced ventricular abnormality, manifested by the preservation of dLVP and minimization of increase in CPP and LVEDP (P<0.05 vs. saline group). Overall, AS-ODN treatment appeared to be equivalent to or even better than atenolol in these effects. AS-ODN restored dLVP to a greater extent than atenolol. INV-ODN showed no effect on ischemia-induced dysfunction and cannot be differentiated from saline group. Data on cardiac function parameters from these studies are summarized in FIG. 12.

5.7 Example 7

Safety Profile of Chronic use of $β_1$-AS-ODNs

Safety profiles including liver transaminases, hematology, immune response and tissue pathology were investigated during three repeated injections of $β_1$-AS-ODNs for extended periods of time. The results indicated that long-term treatment with $β_1$-AS-ODNs is safe without causing toxic effects or immune reaction.

5.7.1 Liver Transaminases

Alanine aminotransferase (ALT) and aspartate aminotransferase (AST) are routinely used as a clinical index for liver function. Their levels increase substantially upon liver damage. SHR were treated with three repeated injections of $β_1$-AS-ODN. Plasma concentrations of ALT and AST were measured after each injection, which revealed no significant difference between AS-ODN and control groups (FIG. 13).

5.7.2 Hematology

Hematological parameters were measured after three repeated injections of $β_1$-AS-ODN. There was no change in total leukocyte count (WBC), platelet count, hematocrit and mean platelet volume (MPV) among three groups (Table 6).

TABLE 6

CLINICAL BIOCHEMICAL AND HEMATOLOGICAL PARAMETERS AFTER REPEATED ADMINISTRATION OF $β_1$-AS-ODN

|  | β1-AS-ODN | INV-ODN | Saline |
| --- | --- | --- | --- |
| Liver Enzymes |  |  |  |
| AST (unit/ml) | 74.0 ± 3.7 | 83.0 ± 8.3 | 82.3 ± 3.8 |
| ALT (unit/ml) | 25.7 ± 1.1 | 30.5 ± 3.8 | 30.0 ± 3.2 |
| Hematology |  |  |  |
| hematocrit (%) | 46.2 ± 0.63 | 46.0 ± 0.1 | 46.6 ± 0.33 |
| WBC ($10^3$/mm$^3$) | 5.48 ± 0.41 | 5.75 ± 1.15 | 5.86 ± 1.12 |
| platelet ($10^3$/mm$^3$) | 685 ± 12 | 706 ± 28 | 685 ± 22 |
| MPV (fL) | 6.93 ± 0.08 | 7.2 ± 0.20 | 7.0 ± 0.09 |
| C-Reactive Protein | ND | ND | ND |
| Antibody to ODN | ND | ND | ND | n = 7–9 for each group, ND: non-detectable.

5.7.3 Immune Response

Antibody-antigen reaction was studied by gel immunodiffusion analysis, which revealed no detectable antibody against $β_1$-AS-ODN. C-reactive protein (CRP), a clinical index for immune reaction, was found negative in all animals.

5.7.4 Tissue Histology

Heart, liver, spleen and kidney were subjected to pathological examination after three repeated injections of $\beta_1$-AS-ODN for more than 2 months. No immunopathology or organ damage was found.

5.8 Example 8

DNA Sequences of Known $\beta_1$-AR Genes

Particularly preferred antisense sequences for the practice of the present invention include those sequences that specifically bind at or near the region of the AUG translation initiation codon of the mRNA encoding a mammalian $\beta_1$-AR polypeptide. Thus, those complementary sequences that are centralized around the region of the mRNA corresponding immediately 5' of the AUG translation initiation codon are particularly preferred. Such sequences may be identified using a secondary structure analysis (e.g., the OLIGO computer program) to ensure that the oligonucleotides do not fold or self-anneal. The BLAST computer algorithm program may also be used to check the specificity of the chosen sequence. The ordinarily skilled artisan, having the benefits of the teachings of the present invention, can select other suitable antisense sequences using the OLIGO and BLAST programs in combination with the teachings of the subject invention to prepare both oligonucleotides that comprises at least 9 to about 35 contiguous nucleotides that are complementary to a portion of the mRNA encoding the open reading frames designated in each of the genes disclosed in SEQ ID NO:187, SEQ ID NO:188, SEQ ID NO:189, SEQ ID NO:190, SEQ ID NO:191, SEQ ID NO:192, SEQ ID NO:193, or SEQ ID NO:194.

For the preparation of full-length or substantially full-length antisense polynucleotides, the inventors contemplate the use of sequences corresponding essentially to the entire $\beta_1$-AR-specific mRNA sequence produced from one or more of the following $\beta_1$-AR genes. For example, the open reading frame of the human $\beta_1$-AR gene extends from nucleotide 87 to nucleotide 1520 of SEQ ID NO:187. Therefore, a full-length antisense polynucleotide would consist of an approximately 1.43-knt (kilonucleotide) sequence that is complementary to the region of SEQ ID NO:187 from about position 87 to about position 1520. In order for the complementary sequence to specifically bind to the native $\beta_1$-AR-specific mRNA sequence, the polynucleotide need not be exactly the same size, or exactly the same sequence of the native mRNA. In fact, substantially full-length sequences or slightly larger-than full-length are contemplated by the inventors to be as useful in the inhibition of $\beta_1$-AR-specific mRNA translation in a host cell as full-length antisense polynucleotides. For example, the size of the complementary polynucleotide may vary (e.g., from about 95% to about 105% of the size of the ORF region of the particular $\beta_1$-AR-specific sequence. Thus, for a 1.43-knt full-length mRNA, a sequence of from about 1.36-knt to about 1.43-knt would be considered "substantially full-length" while a sequence of from about 1.44-knt up to and including about 1.50-knt would be considered "slightly larger than full-length," and complementary polynucleotides may be prepared in either of these size ranges that are sufficiently able to specifically bind to native $\beta_1$-AR-specific mRNA sequences in a host cell and inhibit the ability of the host cell's protein synthesis machinery to translate the native $\beta_1$-AR-specific mRNA sequence into functional $\beta_1$-AR polypeptide.

Such sequences, therefore, would be ideally suited for the preparation of the genetic constructs of the present invention, particularly in their exploitation as gene. therapy vectors for the treatment of the cardiac diseases and disorders of the circulatory system described herein. In the preparation of such gene therapy vectors, one would preferably prepare a genetic construct in which a polynucleotide complementary to the mRNA was placed under the control of a suitable promoter, and then introduce the recombinant vector comprising the genetic construct into the host cells of the affected mammal. Expression of the encoded antisense polynucleotide, therefore, would result in the synthesis of a full-length, substantially full-length, or slightly larger-than full-length polynucleotide that is complementary to the native $\beta_1$-AR-specific mRNA produced by the cell. This complementary sequence could then specifically bind to the target mRNA and thereby reduce the availability of native $\beta_1$-AR-specific mRNA for translation into mature polypeptide by the cellular protein synthesis machinery.

For the human $\beta_1$-AR gene shown in SEQ ID NO:187, exemplary antisense polynucleotide sequences include those that are of from about 1.36-knt to about 1.50-knt in length and that comprise a substantially complementary contiguous sequence selected from about nucleotide 60 to about nucleotide 1600 of SEQ ID NO:187. The selection of substantially complementary, substantially full-length antisense polynucleotides capable of inhibiting the translation of native human $\beta_1$-AR mRNA into polypeptide is within the purview of the skilled artisan having the benefit of the present teaching and the selection methods, computer-based complementarity-defining search algorithms, and the assays for $\beta_1$-AR mRNA and $\beta_1$-AR polypeptides described herein.

In each of the following sequences, the AUG initiation codon is indicated as the first triplet in bold of the corresponding open reading frame.

5.8.1 Human $\beta_1$-AR

The polynucleotide sequence encoding human $\beta_1$-AR polypeptide is disclosed in Frielle et al. (1987). The GenBank™ Accession No. for the *Homo sapiens* $\beta_1$-AR gene is NM000684. The Open Reading Frame extends from nucleotide 87 to nucleotide 1520 (shown in bold) (SEQ ID NO:187)

```
  1 TGCTACCCGCGCCCGGGCTTCTGGGGTGTTCCCCAACCACGGCCCAGCCCTGCCACACCC

61 CCCGCCCCCGGCCTCCGCAGCTCGGCATGGGCGCGGGGGTGCTCGTCCTGGGCGCCTCCG

121 AGCCCGGTAACCTGTCGTCGGCCGCACCGCTCCCCGACGGCGCGGCCACCGCGGCGCGGC

181 TGCTGGTGCCCGCGTCGCCGCCCGCCTCGTTGCTGCCTCCCGCCAGCGAAAGCCCCGAGC

241 GCGTGTCTCAGCAGTGGACAGCGGGCATGGGTCTGCTGATGGCGCTCATCGTGCTGCTCA

301 TCGTGGCGGGCAATGTGCTGGTGATCGTGGCCATCGCCAAGACGCCGCGGCTGCAGACGC
```

-continued

```
 361 TCACCAACCTCTTCATCATGTCCCTGGCCAGCGCCGACCTGGTCATGGGGCTGCTGGTGG
 421 TGCCGTTCGGGGCCACCATCGTGGTGTGGGGCCGCTGGGAGTACGGCTCCTTCTTCTGCG
 481 AGCTGTGGACCTCAGTGGACGTGCTGTGCGTGACGGCCAGCATCGAGACCCTGTGTGTCA
 541 TTGCCCTGGACCGCTACCTCGCCATCACCTCGCCCTTCCGCTACCAGAGCCTGCTGACGC
 601 GCGCGCGGGCGCGGGGCCTCGTGTGCACCGTGTGGGCCATCTCGGCCCTGGTGTCCTTCC
 661 TGCCCATCCTCATGCACTGGTGGCGGGCGGAGAGCGACGAGGCGCGCCGCTGCTACAACG
 721 ACCCCAAGTGCTGCGACTTCGTCACCAACCGGGCCTACGCCATCGCCTCGTCCGTAGTCT
 781 CCTTCTACGTGCCCCTGTGCATCATGGCCTTCGTGTACCTGCGGGTGTTCCGCGAGGCCC
 841 AGAAGCAGGTGAAGAAGATCGACAGCTGCGAGCGCCGTTTCCTCGGCGGCCCAGCGCGGC
 901 CGCCCTCGCCCTCGCCCTCGCCCGTCCCCGCGCCCGCGCCGCCGCCCGGACCCCCGCGCC
 961 CCGCCGCCGCCGCCGCCACCGCCCCGCTGGCCAACGGGCGTGCGGGTAAGCGGCGGCCCT
1021 CGCGCCTCGTGGCCCTACGCGAGCAGAAGGCGCTCAAGACGCTGGGCATCATCATGGGCG
1081 TCTTCACGCTCTGCTGGCTGCCCTTCTTCCTGGCCAACGTGGTGAAGGCCTTCCACCGCG
1141 AGCTGGTGCCCGACCGCCTCTTCGTCTTCTTCAACTGGCTGGGCTACGCCAACTCGGCCT
1201 TCAACCCCATCATCTACTGCCGCAGCCCCGACTTCCGCAAGGCCTTCCAGGGACTGCTCT
1261 GCTGCGCGCGCAGGGCTGCCCGCCGGCGCCACGCGACCCACGGACACCGGCCGCGCGCCT
1321 CGGGCTGTCTGGCCCGGCCCGGACCCCCGCCATCGCCCGGGGCCGCCTCGGACGACGACG
1381 ACGACGATGTCGTCGGGGCCACGCCGCCCGCGCGCCTGCTGGAGCCCTGGGCCGGCTGCA
1441 ACGGCGGGGCGGCGGCGGACAGCGACTCGAGCCTGGACGAGCCGTGCCGCCCCGGCTTCG
1501 CCTCGGAATCCAAGGTGTAGGGCCCGGCGCGGGGCGCGGACTCCGGGCACGGCTTCCCAG
1561 GGGAACGAGGAGATCTGTGTTTACTTAAGACCGATAGCAGGTGAACTCGAAGCCCACAAT
1621 CCTCGTCTGAATCATCCGAGGCAAAGAGAAAAGCCACGGACCGTTGCACAAAAAGGAAAG
1681 TTTGGGAAGGGATGGGAGAGTGGCTTGCTGATGTTCCTTGTTG
```

5.8.2 Canine $\beta_1$-AR

The GenBank™ Accession No. for the *Canis familiaris* $\beta_1$-AR gene is U73207. The Open Reading Frame extends from nucleotide 330 to nucleotide 1751 (shown in bold) (SEQ ID NO:188)

```
   1 CCGGGTGCCGGGCCCGCGGGCTCGGCGCGCTCAGAAACATGCTGAGGTCCCGGCGGCTGT
  61 TGCAGCAGCGGCAGCGGCTCCAGCAGCGGCTCCAGCAGCGGCTCCGGCAGCGGCTCCAGC
 121 GGCGGCAACTCCGGCGGCAGCAGCAGCGGCGGCGGCGGCGGCGGCGCACGGCTCCCG
 181 GCGACCTCCGCGCCCCACGTCCCCGGCGTGGTCCCCGGCCACGGCCCCAGCCCGCCACA
 241 GCGACCTCCGCGCCCCACGTCCCCGGCGTGGTCCCCGGCCACGGCCCCAGCCCGCCACA
 301 CCCCCGCCCCGGCCTCCGCAGCTCGGCATGGGCGCGGGGGCGCTGGCCCTGGGCGCCT
 361 CGGAGCCCTGCAACCTGTCGTCGGCCGCGCCGCTCCCCGACGGCGCGGCCACGGCGGCGA
 421 GGCTGCTGGTGCCCGCGTCGCCGTCCGCCTCGCCGCTGGCCCCGACCAGCGAGGGCCCCG
 481 CGCCGCTGTCGCAGCAGTGGACGGCGGGCATCGGGCTGCTGATGGCGCTCATCGTGCTGC
 541 TCATCGTGGCGGGCAACGTGCTGGTGATCGCGGCCATCGCCAAGACGAAGCGGCTGCAGA
 601 CGCTCACCAACCTGTTCATCATGTCCCTGGCCAGCGCCGACCTGGTCATGGGGCTGCTGG
 661 TGGTGCCCTTCGGGGCCACGATCGTCATGCGGGGCCGCTGGGAGTACGGCTCCTTCCTGT
 721 GCGAGCTCTGGACCTCGGTGGACGTGCTGTGCGTGACGGCCAGCATCGAGACCCTGTGTG
```

-continued

```
 781 TCATCGCGCTGGACCGCTACCTGGCCATCACCGCGCCCTTCCGCTACCAGAGCCTGCTGA
 841 CGCGCGCGCGCGCGGGCCCTCGTGTGCACCGTGTGGGCCATCTCGGCGCTCGTGTCCT
 901 TCCTGCCCATCCTCATGCACTGGTGGCGGGCCGGGGCGACGAGGCGCGCCGCTGCTACA
 961 ACGACCCCAAGTGCTGCGACTTCGTCACCAACCGGGCCTACGCCATCGCCTCGTCCGTCG
1021 TCTCCTTCTACGTGCCCCTGTGCATCATGGCCTTCGTGTACCTGCGGGTGTTCCGCGAGG
1081 CGCAGAAGCAGGTGAAGAAGATCGACAGCTGCGAGCGCCGCTTCCTGGGCGGCCCCGCGC
1141 GGCCCCCGCGCCCCGCCCGCGCCCGCGCCCGCGCCCCGCCCGCGCCCGGCTCCCCGC
1201 GCCCCGCCGCGGCCGCCCCGCTGGCCAACGGGCGCGTCGGCAGGCGGCGGCCCTCGCGCC
1261 TCGTGGCGCTGCGCGAGCAGAAGGCGCTCAAGACGCTGGGCATCATCATGGGCGTGTTCA
1321 CGCTGTGCTGGCTGCCCTTCTTCCTGGCCAACGTGGTCAAGGCCTTCCACCGCGACCTGG
1381 TGCCCGACCGCCTCTTCGTCTTCTTCAACTGGCTGGGCTACGCCAACTCGGCCTTCAACC
1441 CCATCATCTACTGCCGCAGCCCCGACTTCCGCAGGGCCTTCCAGCGCCTGCTGTGCTGCG
1501 CGCGCCGCGCCGCCCGCGGGAGCCACGGGGCCGCCGGGGACCCTCCGCGGGCCCGGCCGC
1561 CGCCGTCCCCCGGGGCCGCCTCGGACGACGACGACGACGACGAGGACGACGCCGGGGCCG
1621 GGGCCGGGGCCGCGCCGCCCGCGCGCCTGCTGGAGCCCTGGGCCGGCTGCAACGGCGGGG
1681 CGGCGGCCGACAGCGACTCCAGCCTGGACGGCGCGGGCAGCCCCGCGGGCGCCTCGGAGT
1741 CCCGGGTGTAGGCGCGCGGCCTCCCGGGGGGCGCATCGGTGTTTACTCCAGACCCAGAGC
1801 AGGTGAACCCCGGGCCCGCGCACCCCCNTCGCATTCATCGAGGCA
```

5.8.3 Sheep β₁-AR

The GenBank™ Accession No. for the *Ovis aries* β₁-AR gene is AF072433/S78499. The mRNA extends from nucleotide 1629 to nucleotide 4749 (underlined). The Open Reading Frame extends from nucleotide 2289 to 3692 (shown in bold) (SEQ ID NO:189)

```
   1 TCCAGCCCCTCTTTCTAGCCCTCTCCTTCCCTCATTTCCCCTTCTCAGGCTCCCCAACT
  61 GGCAGAACTAAGCTGACAATCCTAAGCCAGGGATGCAGAAACAAGTAATTCACCCACATC
 121 CACCCACTGATCATCAAGTTTGGGCCTAAAGCAAATTTACATGTTTGGATAAAGAAAAGT
 181 TGGGCTTCCCTAGTAGCTGAGACCCATCTTCAGTCCTTGGATGGGGAAGATCCCCTAGA
 241 GAAGGAGATGGCAACCCACTCTAGTATTCTTGCCTGGAAAATCCCATAGGCAGCGGAGCC
 301 TGGTGGCTACAGCCCATGGGGTTGCAAGAGTCAGACACAACTTAGCTACTAAAACCACCA
 361 CCCATGGCTTATGAATACACATTGCTGTTAGCTCTCGACTTAGGGAGCTCTCTCCAAGGT
 421 AAGAATATGAGTTTGTTCCTTTCAGAAACTATTCTTTTTATTCCAATGCTAGAAGGATGT
 481 GTGAGCATTATGTAACATTTTCATGCACCCTTAAGTGGGTAATTAGAAGCTCTTTATTTC
 541 TCAGGATTCAATTAAAAGCTTTTTATTTTCAAGGCTGAGTTGAGGACCAGTACTGTGGTG
 601 GAATTAGACAAGGGGCTTGCACACCTTTGGCTACATTGTGTGTTGATGGGCCACCTTCCT
 661 GTAGGTACCTCCCCACATATAGTCACACCACTGCAGAGCTAACGACTCACTAATTTTAAA
 721 CCCATTCAGTTGCCAACCCAACAGCCTTTGATATAACTTTACATGCTATTGGATTTTAAT
 781 CTTTTTGAGTATTTATATATGTTTTCTTCTCTCATCCCTCCAAAATTAATCCTAGAGTTT
 841 TGAGAATCTGGGAACTTGGGCAAAGGAGAAGGCAACGCAGCAGACCAAGAAATTTGAAAT
 901 CTCAGTTCACTACTGTGTCACCCAAAGTCAATGTACCTTTTTGTTTGGACCGGCCCAGC
 961 TCAAGTCATACAATCACGTGAGTAACAGACCACAAAATCCAGGTGTTATTACTGAACATG
1021 ACAAGTCTGAAAAGTAATTACACGTGTTCTAGCTTCCGTGGCGGTGTCATTTACTCTAAC
```

-continued

```
1081 ATGCCTGTCCTTAAGCCTCTCTCTCTCTTTACATTACCGGCACACACCGGTGCACCATAC

1141 TCACACATCCATCAGCTGGGACCTGGGAGTGTGTATTATTCCAACTGGTCCTCAGCATTA

1201 GCTGTCAGATGTCACAACCCCCYGCCGTTTTCTGCATCTGCTGCCCCGGGAAGCGAGAAG

1261 AAGCTTGCAAGAATAGCTCCCGGGAACGTTCCTGAAAGATTGGCGCTCTGCTTTAGCAAG

1321 GCGCTCGCTGGAAAGTTTCTTCTAACCGCTCACACCCGCCTCCGATCCGATCCCCGAGCT

1381 GGCAGGACGCGAGCTGGCTGGGACTCCTCTTGACAGAGGAAGGGCTTTACACACCACCCT

1441 CCTAGGCTGCCCAATACAAGAAACAGTCTTGCAGCCAGACTCCTCCACACCCAGCGAACA

1501 GACCGTCCAAGGCGCTCCGGTGTTTCGAGAACACCGAAGTCCCCTCCCTGCTAAAGGGCG

1561 CGTGAGCTCTGCTCTGCAGGAAACCTGGGCACTGGAGGTAGATGGGATGGGTGGCGGCGG

1621 GTAGAGCCGGGGCGCAGCGGAAAGCAAACGCCGGAGGCAAACGGGGCGCAGGAGAGGGGA

1681 GATTGGGTGCCGCCGTAGGGGCCAGGGTGAAAGCCGGGCGCGGACGGGAACCGAGGGGAA

1741 CTGGGCACTGGAGCCAAGCGGGCTCTGGAAGGGACGCGCGGGCAGGAACCCGCGAGCGCT

1801 GGGGAGGGGCTTGCTTGGCGATCTGCCCCGGACTCCCTAGAGCCGCAGAACCGCCGGTGG

1861 AGGCGGGGTGCTAGGAGTTGGCGGGGCCGGGTGGGGGTGGGGGGGAACCAGAGAGGGGCG

1921 TGCCTTCGCCAGGATTGGCTGCAGGAGCCTGACGCGAGNNNCCGGGGGTTGGCTCGGGGG

1981 AGTGGGAGCCGGGTGGGGTGGGTGCTGGGTGCCGGGGCTGCGGGCTCCGCGAGCTCAGAA

2041 ACATGCTGAGGTCCCGGCAGCTGTTCCAGCAGCGACACCACTCCAGCAGCAGCCGCGGCG

2101 GCTGCGGCGGCGACAGGCACCGGCTCCGGCGGGGAAGGCGCCCGGCGCCATGCCTCCGGC

2161 CCCGCGCCGCGCTGCGCTGACCTGGCCGCGACCTCCCTCCGCGCGCCCCGCCGTTCGGGC

2221 CTCTGGGGGGTTCCCCAACCGCGGCCCAACTCCGCCACACCCCTCTCCCCCGGCCTCCGC

2281 AGCTCGGCATGGGCGCGGGGGCGCTCGCCCTGGGCGCCTCCGAGCCCTGCAACCTGTCAT

2341 TCGCCGCGCCGGTCCCCGACGGCGCGGCCACGGCGGCGCGGCTGCTAGTTCCCNCGTCGC

2401 CGCTCCGCCTCGCTGCTGACCTCGGCCAGCGAGGGACCCCGCTGCTGTCGCAGCAGTGGA

2461 CGGTCGGCATGGGCCTGCTGATGGCATTCATTGTGCTGCTCATCGTGGCGGGCAACGTGC

2521 TGGTGATCGTGGCCATCGCCAAGACTCCGCGGCTGCAGACGCTCACCAACCTCTTCATCA

2581 TGTCGCTGGCCAGCGCAGACCTGGTCATGGGTCTGCTGGTAGTGCCGTTTGGAGCCACAA

2641 TCGTGGTGTGGGGCCGCTGGGAGTATGGCTCCTTCTTCTGCGAGCTCTGGACCTCGGTGG

2701 ACGTGCTGTGCGTGACGGCCAGCATCGAGACCCTGTGTGTCATCGCCCTGGACCGCTACC

2761 TCGCCATCACGTCGCCCTTCCGCTACCAGAGCCTGCTGACCCGCGCGCGAGCGCGGGCCC

2821 TCGTGTGCACCGTGTGGGCCATCTCGGCGCTGGTGTCCTTCCTGCCCATCTTCATGCAGT

2881 GGTGGGGGACAAGGACGCCAAGGCGAGCCGGTGCTACAACGACCCCGAGTGCTGCGACT

2941 TCATCATCAACGAGGGCTACGCGATCACCTCTTCCGTCGTCTCCTTCTACGTGCCCCTGT

3001 GCATCATGGCCTTCGTGTACCTGCGGGTGTTCCGCGAGGCCCAGAAGCAGGTGAAGAAGA

3061 TCGACAGCTGCGAGCGCCGCTTCCTCAGCGGCCCCGCGCGGCTGCCCTCGCCCGCGCTCT

3121 CGCCCGGGGCGCCGCTCCCTGCCGCCGCGGTGGCCAACGGGCGCGCCAACAAGCGGCGGC

3181 CCTCGCGCCTCGTGGCCCTGCGCGAGCAAAAGGCCCTCAAGACGCTGGGCATCATCATGG

3241 GCGTGTTCACGCTCTGCTGGCTGCCCTTCTTCCTGGCCAACGTGGTGAAGGCCTTCCACC

3301 GCGACCTGGTGCCCGACCGCCTCTTCGTCTTCTTCAACTGGCTGGGCTACGCCAACTCGG

3361 CCTTCAACCCCATCATCTACTGCCGCAGCCCCGACTTCCGCAAGGCCTTCCAGCGCCTGC

3421 TCTGCTGCGCGCGCCGGGCCGCCTGCGGGAGCCACGGGGCCGCCGGGGACCCGCCGCGCG
```

-continued

```
3481 CCGCGGGCTGCCTGGCGGTGGCCCGGCCGTCGCCGTCTCCCGGGGCCGCCTCGGACGACG
3541 ACGACGACGACGACGAAGACGACGTCGGGGCCGCGCCGCCCGTGCGCCTGCTGCAGCCCT
3601 GGGCTGGCTACAACGGCGGGGCGGCGGCGAACAGCGACTCGAGCCCGGACGAGCCAAGCC
3661 GCCCGGGCTGCGGCTCGGAATCCAAGGTGTAGGGACGGGCGCCCCTCCCCGCCTTCCCCG
3721 GCTTCCCCAGTCCGGGAGCGGGCTGTGCGCTCCAGGAGCAAGAGAACCCGGGCGMCCCTG
3781 AACCGCTTCCCCGGGAAAGAGGTCTGTGTTTACTCGAGACCGTAAAGCAGGTGAACTCGA
3841 AGCCTGCGAACCTCGTCTGCATCATCCAAGGGCAAATAGGAAAGCCACGGACCGTCGCAC
3901 AGAAAGGAAAGTTTGGGGAGAGGTGGGAGAAGTTTGGGGAGGGGTGGAAGAGTGGCTTAC
3961 TGATTGTTCTTGGGGTTCTTTTTCCTGTTTCTGGTCCAGCCTTCTGTGTGTGCGTGTGAT
4021 GCATCTTTAGAGTCCCTCCTCCCCCCGCCCCCCGCGACGTGGCTTTTAACACTTTCTGC
4081 GATGACTGGGAAGGGAAGGGGGAAGCGTTAGGAGGTAAAAGTCTCTCGACTTAGTTTCCA
4141 TCCCATTCCTGGGAACAGAAGCGGTCAGCCAGAGAGAGGAGAGAGAATGACACTTTAT
4201 CAGGACGTTGTTTCCTTTTGCTTTTCAGAGAAATACCATTTTAATTTCTGAGGAATTATT
4261 TCTCCTGTTCTGAAAGCCGAGGGCAAGGATGGATGCAAAAATCGCGTTTCAGGAAGTTTT
4321 ATGCTCTTCTTGGAACAAGCCTCACCTTGCTTCCCTTTCGGAGGGCAAGCGGGCTGTCCC
4381 TGAACGCCTCCTCGGTGGTCAGGCTGAGGGGTTCCTACCTCACTCACACGGTGCACATTG
4441 CACGGCCAGATAGAGAGACTTGTTTATATTAAACAGCTTATTTATGTATCAATACTAGTT
4501 GGCCGGACCAGGCGCTGAGCCTTCGTGACATGTGACTCTGTCCATTGAAGACAGGACAGA
4561 AAAAGGAAAAGAAAAAAGGAAAACAATTCAGATTACTGCACATGTGGTATAGACAAAAA
4621 ATCAAAACAAAAAAGCCGTGATTCAAAGTGGCATTTTTTTGCACAGTATTAGGAACTGT
4681 AAAGTCCACAGAAAATGTTATTTGCACAAAAAGAAATGAAATATTTTTTAATGGGAGTGG
4741 GGTGGGGCA
```

5.8.4 Porcine $\beta_1$-AR

The GenBank™ Accession No. for the *Sus scroffa* $\beta_1$-AR gene is AF042454. The Open Reading Frame extends from nucleotide 456 to nucleotide 1862 (shown in bold) (SEQ ID NO:190)

```
  1 GACTCCCCAGAGCTGCTGAACCGCCGGGGGAGGGGGTGGGGGAGTTGGCGGGGGGG
 61 GGGGGGGAGAACCAGATCGGGGCGTGCTTCCTCGGATTGCTGCAATAGCTGACGCGA
121 GGCCCCGGGGGTTGGCTCCAGGGAGTGGGATGGGAGCGGGTGGGGTGGTGCTGGGTG
181 CCGGGGCTGCGGGTTCCGGCGCTCAGAAACTGCTGAGGTCGCAGCTGTCCAGCAGCG
241 ACACCGCTCCAGCAGCAGCGGCGGCGGCGGGGCGGCGACGCGCACAGCCTGGCGGGG
301 AAGGCGCCCTGCGCCCATGCCTCCGGCCCCCGCCGCGGCGCCCTGACCGGCCGCGAC
361 CTCCCTCGTCGCGCCCCGCCGCCCGGGCCTTGGGGGGTCCCGACCGCGCCCAACTC
421 CGCCACACCCCCGCCCCCGCCTCCGCAGCCGGTATGGGCGGGGCGTCGCCCTGG
481 GTGCCTCCGAGCCCTGCAACCTGTCATCGGCGCGCCGCTCCCGACGGCCGGCCACCG
541 CGGCGCGGCTGCTGGTGCCTGCGTCCCCTCCGCCTCGCTCTGACCCCACCAGCGAGG
601 GATCCGTGCAGCTGTCGCAGCAGTGGACGGTGGCATGGGCTCCTGATGCGCTCATCG
661 TGCAGACGCTCACCAACCTCTTCATCATGTCCTGGCCAGGCCGACCTGTCATGGGC
721 TGCAGACGCTCACCAACCTCTTCATCATGTCCTGGCCAGGCCGACCTGTCATGGGC
781 TGCTGGTGGTGCCATTCGGGGCCACCATCGGGTGTGGGGCGCTGGGAGACGGCTCCT
```

-continued

```
 841 TCTTCTGCGAGCTCTGGACGTCGGTGGACGACTGTGCGTACGGCCAGTTCGAGACCC
 901 TGTGTGTCATCGCCCTGGACCGCTACCTCGCATCACGTCCCCTTTCGCACCAGAGCC
 961 TGCTGACCCGCGCGGCACGGGCCCTCGTGTCACCGTGTGGCCATCTCGCCCTGGTGT
1021 CCTTCCTGCCCATCCTCATGCACTGGTGGCGGACAAGGGGCCGAGGCAGCCGCTGCT
1081 ACAACGACCCCAAGTGCTGCGATTTCGTCACAACAGGGCTACGCCATCCCTCGTCCG
1141 TGGTCTCCTTCTACGTGCCCTTGTGCATCAGGCCTTCGTTACCTGCGGTGTTCCGCG
1201 AGGCCCAGAAGCAGGTGAAGAAGATCGACACTGCGAGCGCGCTTTCTCGCAGCCCCG
1261 CGCGGCCGCCCTCGCCCGCGCCCTCGCCCGGTCCCCGCTCCTGCCGCCCTGCCGCAG
1321 CCCCGGTAGCCAACGGGCGCACCAGCAAGAGCGGCCCTCCGCCTCGTGCCCTGCGAG
1381 AGCAGAAGGCGCTCAAGACGCTGGGCATCACATGGGCGTTTCACGCTCGCTGGCTAC
1441 TCGTCTTCTTCAACTGGCTGGGCTACGCCACTCGGCCTTAACCCCATCTCTACTGCC
1501 TCGTCTTCTTCAACTGGCTGGGCTACGCCACTCGGCCTTAACCCCATCTCTACTGCC
1561 GCAGCCCTGACTTCCGCAAGGCCTTCCAGCCCTGCTCTGTGCGCGCGGGTCGCCC
1621 GCGGGAGCTGCGCGGCCGCCGGGGATGGGCGCGCGCCTCGGCTGCCTGCGGTGGCCC
1681 GGCCGCCGCCGTCGCCCGGGGCCGCCTCGGCGACGACGAGACGAAGAAACGTCGGGG
1741 CCGCCGCCGGCGCCCCTGCTGGAGCCCTGGCCGGATAAACGGCGGGCGGCACGTG
1801 ACAGCGACTCGAGCCTGGACGAGCGGACGCCGGGGCCGGCCTCGGAACCAAGGTGT
1861 AGGGCCCAGCGCTCCCTCCCCACCTCCCAGGGGATGCAGCTCTGCGCGAGAGAAGA
1921 GAACCCGGCGCCCCGAAAGGCTTCCCGGGGATGAGGAGACTGTGTTTATCGAGACCG
1981 AAAGCAGGTGAACTCGCAAACCTCGTCTGCTCATCTAAGCAAACAGAAAGCCGGACC
2041 GCTGCACAGAAAGGAAAGTTTGGGGAGGGTGGAGAGTGGTTGCTCATTTTGTTGAGT
2101 TCTTTTCTCTGTTTGTGGTCCGTCCTCCTTTGTGTGTGCTGTGATGCACTTTAGATT
2161 TTTATTCCCCCAGGTGGTTTTTAACACTTTTGCGAAGACAGGGAAGGGTGGGAGAAG
2221 CAGGAGAGTTTTTAAAAAGGTGTCTCAACTGGCTTCCATCCGTTCCCGGGACGGAGC
2281 AGTC
```

5.8.5 Rat β₁-AR

The rat β₁-AR polypeptide and polynucleotide sequences are disclosed in Machida et al. (1990). The GenBank™ Accession No. for the *Rattus norvegicus* β₁-AR gene is D00634. The Open Reading Frame extends from nucleotide 1257 to nucleotide 2657 (shown in bold) (SEQ ID NO:191)

```
  1 GGTACCAGAGTACAAACGTCGGTGTTAAGGTGTTGGTACTGGAGTCAAAAGTCTGAAG
 61 CGTCATTCTCTGAGTTCTTTTACGCGGGGTGGGGGTTGGGGGTGGGCGTGTCATTTA
121 CTCCGGACTTAATGTTGCCCAAACTTCTCCTTTATACTCAGAACTCATCCATCCTTTT
181 CCTTAGCTGGGATTGGGAACGTGTGTGTCCAACTGGTCCTTGGCGTTGGAGTTACAGC
241 CACAAACCTTCCCTTCCTTCCCCATCCACTGCACTTGAGGGAGAGAGAGACAGCTCTG
301 CGGAAGAACAGCGCCCAGAGGCCTTTCTGACAGATGGCACTCTGCTCCCCAATCCGCC
361 TGGCTGCAAAGTTTCCTCTATAACTAACACCCACTTCCTATTCCCCAAGTGTCATTCT
421 GGCCGGGTCCCCTCGCGATCGGGAAGAGCCAGGCTGCCTGATGGCAGAACAGTCTCAC
481 AGCTAAATTCTCTAATCCCACAGATAGGCTGTCCAAGGCATCTCCGGAAGCCAGCAAG
541 TTTCCCTTCTAGCTACCAGGACCATGCACTAGAGGTAGAAAGGCGAGGGGCTACGGGG
601 CGCCGAAGGGAAACCGGCTCTGCGGGAGGGCAAAATGAGAGCTGGGTGCAGGGCAAGC
```

-continued

```
 661 GGACACCACTTGGGCGGTGGGGTGGGCACAGGAGGCCGGCGGGGCACCCAGAGGGCGC

721 AGCAGACCAGACTCTGGAAGAGCCTGAGCAGGAAAGGGCGCGCTCGCTGAGCCCGTGG

781 GTGCCGGCTGCGTAGTCCACCGCAATCTTTGGAGCCTTTCAATCGCGGTGGAGGGGGT

841 GCTGGGTGTTGGGGGTGGGGCACCATTGTTCGGGGGCGTGCCTTGGACGCGATTGGCT

901 GCGGGAGCCTGACGCGCGGCCCGGGGCTGGCTGGGGGGTAGGGAGCGAGTGGGGGGG

961 AGGTGCTGGGTGTTGGAGCCCCGGCCCCGCGCGCTCAGAAACATGCTGAGTCCCGGCA

1021 ACTCTTCCAGCAGCGACCCGTCCAGCAGCAGCGGCGGCGGCGGCGGGACACGGCT

1081 TGGCTACGGAGGAGAAGGCGCCGGCGTCCATGCCTCCGGCCCCAAGCCGGGCTGCCCT

1141 GACCTGGCCGCGACCTCCCCCGTCCCCGCGCGCCCCCAGCCCCGGCTCTGGGGTGC

1201 TTCCCAGGCGCGGCCCAGTCCGCCACACCCCCGCGCCCGGCCTCCGAATCGGCATGG

1261 GCGCGGGGCGCTCGCCCTGGCGCCTCCGAACCCTGCAACCTGTCGTCGCCGCGCCGC

1321 TGCCCGACGGCGCGGCCACCCGGCACGACTGCTGGTGCTCGCGTCGCCTCCGCCTCGC

1381 TGCTGCCTCCAGCCAGCGAGGCTCAGCGCCGTGTCGCAGCAGTGGACCCGGGTATGG

1441 GCCTACTCCTGGCGCTCATCTGCTGCTCATCGTAGTGGGCAACGTGTTGTGATCGTGG

1501 CCATCGCCAAGACCCCGCGGTGCAGACGCTCACCAACCTCTTCATCATGCCCTGGCCA

1561 GCGCCGATCTGGTCATGGGATGCTGGTGGTGCCTTTCGGGGCCACCATTTGGTGTGGG

1621 GCCGCTGGGAGTACGGCTCCTCTTCTGTGAGCTCTGGACTTCGGTAGACTGCTATGTG

1681 TGACGGCCAGCATCGAGACCTGTGTGTCATCGCCCTGGACCGCTACCTCCCATCACGT

1741 CGCCCTTTCGCTACCAGAGCTGCTGACGCGCGCGCGAGCGCGGGCCCTCTGTGCACAG

1801 TGTGGGCCATCTCCGCGCTGTGTCCTTCCTGCCCATCCTCATGCACTGGGGCGGGCCG

1861 AGAGCGACGAAGCGCGCCGCGCTACAACGACCCCAAGTGCTGCGATTTCTCACCAACC

1921 GGGCCTACGCCATCGCCTCGCCGTCGTCTCCTTCTACGTGCCCCTGTGCTCATGGCCT

1981 TCGTGTACCTCCGGGTGTTCGCGAGGCCCAGAAACAGGTGAAGAAGATCACAGCTGCG

2041 AGCGCCGCTTCCTCAGCGGCCGCCCCGGCCGCCCTCGCCCGCGCCCTCGCATCACCAG

2101 GGCCACCGCGCCCCGCAGACCGCTGGCCAACGGGCGCTCCAGCAAGCGGGGCCGTCGC

2161 GCCTCGTGGCTCTGCGAGAGAGAAGGCGCTCAAGACACTGGGCATCATCTGGGTGTGT

2221 TCACGCTCTGCTGGCTGCCCTCTTCCTGGCCAACGTGGTGAAAGCTTTCACCGCGACC

2281 TGGTGCCGGATCGCCTCTTCTCTTCTTCAACTGGCTGGGCTACGCCAACCGGCCTTCA

2341 ACCCCATCATCTACTGCCGCGCCCCGACTTCCGCAAGGCTTTCCAGCGCTGCTTTGCT

2401 GCGCGCGCCGGGCCGCCTGCGACGCCGCGCAGCCCACGGGGACCGGCCGGCGCCTCGG

2461 GCTGCCTGGCGAGAGCTGGGCGCCGCCGTCCCCGGGGCTCCTTCGGACACGACGACG

2521 ATGACGCCGGGGCCACCCCACCGCGCGCCTGTTGGAGCCCTGGGCCGGCGCAACGGCG

2581 GGACGACCACTGTGGACAGCATTCGAGCCTGGACGAGCCGGACGCCAGGCTTCTCCT

2641 CCGAGTCCAAGGTGTAGAGGCCAGGCTCTCCGGGCGCACGGACGCCGCTCCCATAGTC

2701 CCGGGCTGGACACGGGCTCTCATCCCTAGAGGAAGAGAGAAAGAATGGGCCCTGAGCC

2761 GCTCCCCAGGGGAGAGAGGAATTTCTGTTTACTCAAGACCGAAAGCAGGGAATGCGAA

2821 GCCCACAGATCTTTTGAATCTCCGAGACGTACAGAAAAGCCCCGGACCGGCGTTGCGC

2881 AAAAAGGAAAGTTTGGGAGTGTTGGGAGAGTGTGGCTTAGTGTGGCTTATGGCTTGTC

2941 TTGAGTTCCTTTCTCTCTGAGTTCGGCCTTTCGTGTGTTTAATGCACCTTAGGCACCC

3001 CCCCCCCGTGGGTTTTGACATTTCTGCAAGGACCCGAGTGGAAACTAGGGGGAGGGG
```

```
3061 AAGGGGGAGGGTGGAGTCTACACCTGCCTTCTACTTCACACCTAGGAACTAAGTGTTC

3121 AGCTCTGGTTTGGGGTGGGCCAGGAGCGGTGATAATTAGCCAGGAAGTGTCCTTTTGC

3181 TTTCTAAAGAAATTGCATATAATTCCGGAGTATTGGTGTCTCCTTAAAGAAAGGGGGG

3241 AAAGGTGGCTGAGAAACAGACAATCTGGTTTCGAGAAACTATTTGTGGACACGGTTCA

3301 CCTTGCTTTCTCCTGGAGGGAAACCCTGTCCCTGCGCGCCTCGGTGGTCTGCTGTGGG

3361 TCCTCTACCTCACTCTGTGCTATTGCACAGCAAGATAGAAAGACTTGTTATATTAAAC

3421 AGCTTATTTATGTATCAATATAGTTGGAAGGACCAGGCGCTGAGTCTCTTCTGTGACA

3481 TGTGATTCTGTCAACTAAAGTAGGACAGAACAAAAGGAAACAGTTGGGATATTGCACA

3541 TGTGGCTAAAAACAAAGATGCAAAAAAAAAAGGCAGTGGTTGAAAGGCCTTTTGCGCA

3601 GTGTTAGACATTGTAAAATCATAGAAGTTGTTAACTTGCACAAAAAATTAATATTTTT

3661 AATGGGACGGGGAGGTGGGCGATCT
```

5.8.5 Rhesus Monkey $\beta_1$-AR

The GenBank™ Accession No. for the *Macaca mulatta* $\beta_1$-AR gene is X75540. The Open Reading Frame extends from nucleotide 1425 to nucleotide 2867 (shown in bold) (SEQ ID NO:192)

```
   1 CCAAGGAATCTGAAATCGCAGTTCATGACGTCAGCATAAACCGACAGTACCTTTTGTTT

61 GTATTGACCCAGCTCAAATTATAAAATCACATGAGTAATAAAAACACAAAATACAGGTGTT

121 GTCACTGAAAAGCCTAAAATGTAACTAAACGCGTTTTCCCCCCTCGCGGTGGTATCATTT

181 ACTCTGTATCTCAACGTTTCTGTCTCCCTAAGACTCTCCCTTTATATCGTGAGCACACAT

241 TTTTGCATCATGCTCACACATTCATTAGCTAGGACTGAGGAGTGTGTACGATTCCAACGG

301 GCCCTCAGCGTTAGCTGTTAGATGCACAAACCTTCACTTCCTTTCCACATCTACTGCACT

361 TGAGGTTCAACAGAGGATCCTTGCAAGAACAGTGCCCAGAGAGCATTCTTGACAGATGCG

421 CGCTTAGCTCCAGCAACCCGCTCTGCTGGGAAGTTTCTTCTAACCACTAACACCCACCTC

481 CAATCCCCCAAGCTGTCACGACGCAGGCTGGCTGGGTCCCGTATTGACGGGGGAAGGGTT

541 TTACACACATCCTGCTAGGCTGCCCCACATCACAACCAAGCTCGCAGGGCAAACTCCTCC

601 AAGCCTGGCGGACAAGCTGTCCCAGGCGCTCTGGCGCTTCCTGAACACCAAGGTCCCCTC

661 CGCGCTCAAGGGAGCTAGCGCACTGTTACGCAGGGAACCCCGGCACTGCAGGTCGAGGGG

721 ATGCCGAGGGAGCGGGGCGCAGCAGGCAGCCGACTGCTGTAGGCAAACGGCGCGCAGGA

781 GGCAAACGAGGCGCAGGAGCCGGTGCGAGAGCGAGTGGGCGCTGAGAGAGGGGCGGGGC

841 CCCAGGGGGAGGCGAGCGCGGGAGGGGGCACGGGAGAACAGGGACCAGGAACCAGCGGG

901 CGCAGGAAGGGGTGCGTCCGCAAGAACCCGCGGGCGCACGGGAGGCACTAGCTCCACGAT

961 CAGCTCGGGACTCTCAGGAGCCGCTCAATTGCCAACGGGAGGGGCTGCGGGGAGTTGGA

1021 GGTTGGGGGGCTGACCAGACGGGGCGTGCCTTTGCCCGGATTGGCTGCAGGAGGCTGA

1081 CGCGAGGCCCCGGGGGTTGGCTTGGGGAGTGGGAGCGGGGTGGGGTGGGTGCTGGGTGCC

1141 GGAGCTGCGGGCCCGGCGCGCTCAGAAACATGCTGAGGTCCCGGCGGCTCTTCCAGCAGC

1201 GGCAGCGGCTCCAGCAGCAGCGGCGGCGGCGGCGGCGGCAGCGACAGCGCTCGGCTC

1261 CGGCGGGAAAGGCGCCCGGCGCCCATGCCTCCGGCCCCGGGCCGCGGCTGCCCTGACCCG

1321 GCCGCGACCTCCCTCTGCGCACCCCGCCGTCCAGGCTTCTGGGGTGTTCCCCAACCAAGG

1381 CCCAGCCCTGCCACACCCCCCGCCTCCGGCCTCCGCAACTCGGCATGGGCGCGGGGCGC

1441 TCGTCCTGGGCGCCTCCGAGCCCGGTAACCTGTCGTCGGCCGCACCGCTCCCCGACGGCG
```

-continued

```
1501 TGGCCACCGCGGCGCGGCTGCTGGTGCCCGCGTCGCCGCCCGCCTCGTTGCTGCCTCCCG

1561 CCAGCGAAGGCCCCGAGCCGCTGTCGCAGCAGTGGACGGCGGGCATGGGTCTGCTGATGG

1621 CGCTCATCGTGCTGCTCATCGTGGCGGGCAACGTGCTGGTGATCGTGGCCATCGCCAAGA

1681 CGCCGCGGCTGCAGACGCTCACCAACCTCTTCATCATGTCCCTGGCCAGCGCCGACCTGG

1741 TCATGGGGCTGCTGGTGGTGCCGTTCGGGGCCACCATCGTGGTGTGGGGCCGCTGGGAGT

1801 ACGGCTCCTTCTTCTGCGAGCTGTGGACCTCGGTGGACGTGCTGTGCGTGACGGCCAGCA

1861 TCGAGACCCTGTGTGTCATCGCCCTGGACCGCTACCTCGCCATCACCTCGCCCTTCCGCT

1921 ACCAGAGCCTGCTGACGCGCGCGCGGGCGCGGGGCCTCGTGTGCACCGTGTGGGCCATCT

1981 CAGCCCTGGTGTCCTTCCTGCCCATCCTCATGCATTGGTGGCGGGCGGAGAGCGACGAGG

2041 CGCGCCGCTGCTACAACGACCCCAAGTGCTGCGATTTCGTCACCAACCGGGCCTACGCCA

2101 TCGCCTCGTCCGTGGTCTCCTTCTACGTGCCCCTGTGCATCATGGCCTTCGTGTACCTGC

2161 GGGTGTTCCGCGAGGCCCAGAAGCAGGTGAAGAAGATCGACAGCTGCGAGCGCCGTTTCC

2221 TCGGCGGCCCCGCGCGGCCGCCCTCGCCCTCGCCCTCGCCCTCGCCCTCGCCGGTCCCCG

2281 CGCCGCCGCCCGGACCTCCGCGCCCCGCCGCCGCCGCTGCCACCACCGCCCCGCTGGTCA

2341 ACGGACGTGCGGGTAAGCGGCGGCCCTCGCGCCTCGTGGCCCTGCGCGAGCAGAAGGCGC

2401 TCAAGACGCTGGGCATCATCATGGGCGTGTTCACGCTCTGTTGGCTGCCCTTCTTCCTGG

2461 CCAAACTGGTGAAGGCCTTCCACCGCGAGCTGGTGCCCGACCGCCTCTTCGTCTTCTTCA

2521 ACTGGCTGGGCTACGCCAACTCGGCCTTCAACCCCATCATCTACTGCCGCAGCCCCGACT

2581 TCCGCAACGCCTTCCAGCGACTGCTCTGCTGCGCGCGCAGGGCTGCCCGCCGGCGCCACG

2641 CGGCCCACGGAGACCGGCCGCGCGCCTCGGGCTGTCTGGCCCGGCCCGGACCCCCGCCGT

2701 CGCCCGGGGCCGCCTCGGACGACGACGACGACGATGTCGTCGGGGCCACGCAGCCCGCGC

2761 GCCTGCTGGAGCCCTGGGCCGGCTGCAACGGCGGGCGGCGGCGGACAGCGACTCGAGCC

2821 TGGACGAGCCGTGCCGCCCCGGATTCGCCTCGGAGTCCAAGGTGTAGGGCCCGGCGCCGG

2881 GCGAGGACGCCGGGCACCCCGGGAGGAGGAGAGCCCGGGCGCCCCGGAACGACTTCCCGG

2941 GGGAACGAGGAGATCTGTGTTTACTCAAGACCGAAAGCAGGTGAACTCGAAGCCCACAAT

3001 CCTCGTCTGAATCATCCGAGGCAAACAGAAAAGCCACGGACCATTGCACAAAAAGGAAAG

3061 TTTGGGAGGGATGGGAGAGTGGCTTGCTGATGTTCCTTGGTTTTTTTCTTTCTTTCTT

3121 CCTTTTTTTTTTTTTTTTCTGTTTGTGGTCCGGCCTTCTTTTGTATGTGCGTGTGATGC

3181 ATCTTTAGATTTTTTTCCCCACGTTGGTTTTGACACTCTCTGCGAGGACCGGAGTGG

3241 AAGTTGGGTGGGTTACGGGAAGGAAGAAGCATTAGGAGGGGATTAAAATCGATCAGCGTG

3301 GCTCCTATCCCTTTCCCAGGAACAGGAGCAGTCTACCAGCCAGAGGGAGGAGAATGACAG

3361 TTTGTCAAGACGTATTTCTTTTGCTTTCCAGATAAATTTCATTTTAATTTCTAAGTAATG

3421 AGTTCTGCTGTCATGAAAGCAAAGAGAAAGGATGGAGGCAAAAAAAAAAAAATTCACGTT

3481 TCAAGAAATGTTAAGCTCTTCTTGGAACAAGCCCCACCTTGCTTTCCTTGTGTAGGGCAA

3541 ACCGGCCGTCCCCGCGCGCCTGGGTGGTCAGGCTGAGGGATTTCTACCTCACACTGTGC

3601 GTTTGCACAGCAGATAGAACGACTTGTTTATATTAAACAGCTTATTTATGTATCAATATT

3661 AGTTGGAAGGACCAGGCGCAGAGCCTCTCTCTGTGACATGTGACTCTGTCAATTGAAGAC

3721 AGGACATTAGAGAGAGAGAAACAGTTCAGATTACTGCACATGTGGATAAAAACAAAAACA

3781 ACAAAAAAAGGAGTGGTTCAAAATGCCATTTTTGCACAGTGTTAGGAATTACAAAGTCCA

3841 CAGGAGATGTTACTTGCACAAAAAGAAATTAAATATTTTTTAAAGGGGGAGGGGCTGGGC
```

```
3901 AGATCTTAAAAACTAAAATAAAATTCAAACTCTACTTCTGTTGTCTAGTATGTTATTGAG

3961 CTAATGATTTATTGGGGAAAATACCTTTTTATACTCCTTTATCATGGTACTGTAACTGTA

4021 TCCATATTATAAATATAATTATCTTAAGGATTTTTATTTTTTTTTTTTATGTCCAAGT

4081 GCCCACGTGAATTTGCTGGTGAAAGTTAGCACTTGTGTGTGAACTCTACTTCCTCTTGTG

4141 TGTTTTACCAAGTATTTATACTCTGGTGCAACTAACTACTGTGTGAGGAATTGGTCCATG

4201 TGCAATAAATACCAATGAAGCACAATCAAGATTATGTACTGTGTGTCTGTAAAGGGTCAG

4261 TGATAATGAAAAAGACAGTTTGTTTTGTTCAAAATATAGACTGGATTTCCCATAGAGCTC

4321 TTTTAATAGACTTTCATGACTCAATAACATAGCAAAATGCCTCCAGACCTAAATAAGGTG

4381 TTTACCTACTGAGAGCTGCAG
```

5.8.6 Mouse $\beta_1$-AR

The GenBank™ Accession No. for the *Mus musculus* $\beta_1$-AR gene is L10084. The Open Reading Frame extends from nucleotide 100 to nucleotide 1500 (shown in bold) (SEQ ID NO:193)

```
   1 GACCTCCCCGCGCGGGCCCCGCAGCCCCGGCTCCTGGGGTGCTCCCCAGGCGCGGCCCAG

61 CCCCGCCACACCCCCCGCCCCCGGCCTCCGCAGCTCGGCATGGGCGCGGGGGCGCTCGCC

121 CTGGGCGCCTCCGAACCCTGCAACCTGTCGTCCGCCGCGCCGCTGCCCGACGGTGCGGCC

181 ACCGCGGCGCGGCTGCTGGTGCTCGCGTCGCCTCCCGCCTCGCTGCTGCCTCCAGCCAGC

241 GAGGGCTCAGCGCCGCTGTCGCAGCAGTGGACCGCGGGTATGGGCCTACTCGTGGCGCTC

301 ATCGTTCTGCTCATCGTGGTGGGTAACGTGCTGGTGATCGTGGCCATCGCCAAGACCCCG

361 CGGCTGCAGACGCTCACCAACCTCTTCATCATGTCCCTGGCCAGCGCTGATCTGGTCATG

421 GGATTGCTGGTGGTGCCTTTCGGGGCCACCATCGTGGTGTGGGGCCGCTGGGAGTACGGC

481 TCCTTCTTCTGCGAGCTCTGGACTTCGGTAGATGTGCTGTGTGTGACGGCCAGCATTGAG

541 ACCCTGTGTGTCATCGCCCTGGACCGCTACCTCGCCATCACGTCGCCCTTTCGCTACCAG

601 AGTTTGCTGACGCGCGCGCGAGCGCGGGCCCTCGTGTGCACAGTGTGGGCCATCTCGGCG

661 TTGGTGTCCTTCCTGCCCATCCTCATGCACTGGTGGCGGGCCGAGAGCGACGAAGCGCGC

721 CGCTGCTACAACGACCCCAAGTGCTGCGATTTCGTCACCAACAGGGCCTACGCCATCGCC

781 TCGTCCGTCGTCTCCTTCTACGTGCCCCTGTGCATCATGGCCTTCGTGTACCTGCGGGTG

841 TTCCGCGAGGCCCAAAAACAGGTAAAGAAGATCGACAGCTGCGAGCGCCGCTTCCTCGGC

901 GGCCCAGCCCGGCCGCCCTCGCCTGAGCCCTCGCCGTCACCTGGGCCACCGCGCCCCGCA

961 GACTCGCTGGCCAACGGGCGCTCCAGCAAGCGGCGGCCGTCGCGCCTCGTGGCTCTGCGC

1021 GAGCAGAAGGCGCTCAAGACACTGGGCATCATCATGGGTGTGTTCACGCTCTGCTGGCTG

1081 CCCTTCTTCCTGGCCAACGTGGTGAAGGCTTTCCACCGCGACCTGGTGCCGGATCGCCTC

1141 TTCGTCTTCTTCAACTGGCTGGGCTACGCCAACTCGGCCTTCAACCCCATCATGTACTGC

1201 CGCAGCCCCGACTTCCGCAAGGCTTTCCAGCGCCTGCTCTGCTGCGCGCGCCGGGCCGCC

1261 TGCAGACGCCGCGCAGCCCACGGGGACCGGCCGCGCGCCTCCGGCTGCCTGGCGAGAGCT

1321 GGGCCGCCGCCGTCCCCCGGAGCTCCCTCGGACGACGACGACGACGACGCCGGGACCACC

1381 CCACCGGCGCGCCTGCTGGAGCCCTGGACCGGCTGCAACGGCGGGACAACCACTGTGGAC

1441 AGCGATTCGAGCCTGGACGAGCCGGGGCGCCAGGGCTTCTCCTCGGAGTCCAAGGTGTAG

1501 AGAGCCAGGCTCTCTGGGCGCACGG
```

5.8.7 Frog β₁-AR

The GenBank™ Accession No. for the *Xenopus laevis* β₁-AR Gene is Y09213. The Open Reading Frame extends from nucleotide 301 to nucleotide 1458 (shown in bold) (SEQ ID NO:194)

```
   1 ACCACCAACGTGGCACCTGCAGCTGAGGGACTAGAAAACTCCATAGCCCAGAGGAGTCAC

61 TGGCAGCCACAACTGTACTGAAAGTGTAGCAGCTCACAAGCCCCCGGCTTATTCATCCAG

121 GAGACAGAGAGACTGGCACAGTCCAGCCCAGTGGCACGAGAGTCTGCACCAACCAGGGGG

181 AGTTATAGTTTCTGGACACAAGAGACTACCTGGCATCCCGCTGGCACCGACACTTTCTTT

241 CTGTTCTGATATTCTGTTGCCCAAATGATCTGAGGCTCCAGGCTAGGACCTATGCCCATC

301 ATGGGAGACGGTTGGGGGCCTATGGAGTGCAGGAACAGGTCTGGTACCCCTACAACAGTG

361 CCCAGCCCTATGCACCCCCTGCCCGAGCTCACTCACCAGTGGACTATGGGAATGACTATG

421 TTCATGGCGGCCATCATCCTCCTCATCGTCATGGGCAACATCATGGTCATTGTGGCCATT

481 GGGAGGAACCAGAGGCTCCAGACCTTGACCAACGTCTTCATCACGTCCTTGGCTTGTGCC

541 GACCTCATTATGGGTTTGTTTGTTGTGCCCCTTGGTGCCACGTTGGTGGTGAGTGGCAGG

601 TGGCTGTACGGGTCGATATTCTGTGAGTTCTGGACGTCAGTGGACGTATTGTGCGTCACG

661 GCGAGTATAGAGACCCTGTGCGTCATCTCCATCGACCGCTACATCGCCATCACCTCACCC

721 TTCCGCTACCAGAGTCTCCTGACCAAGGGCCGTGCCAAGGGAATCGTGTGCAGCGTGTGG

781 GGCATCTCAGCCCTGGTCTCGTTCCTGCCCATCATGATGCACTGGTGGAGGGACACTGGC

841 GACCCCCTGGCCATGAAATGTTACGAGGATCCTGGGTGCTGTGATTTTGTCACCAACAGA

901 GCTTACGCCATCGCCTCGTCCATCATCTCCTTCTATTTCCCACTCATCATCATGATCTTC

961 GTCTACATCAGGGTCTTCAAGGAGGCGCAGAAGCAGATGAAGAAGATTGACAAGTGCGAG

1021 GGCAGGTTCTCCCATAGCCACGTCCTGAGCCACGGCAGGTCCAGCCGGAGGATCCTCTCC

1081 AAAATCCTGGTGGCCAAAGAGCAGAAAGCCTTGAAGACCCTCGGGATTATCATGGGCACC

1141 TTCACCCTGTGCTGGTTGCCCTTCTTCTTGGCCAACGTGGTCAATGTCTTCTACAGGAAC

1201 CTGATCCCAGACAAACTCTTCCTCTTCCTCAACTGGCTGGGCTACGCCAACTCCGCGTTT

1261 AACCCCATCATCTACTGCAGGAGCCCAGACTTCAGGAAGGCTTTCAAGAGACTCCTGTGT

1321 TGCCCCAAAAAGGCAGATCGGCACCTCCACACTACTGGGGAGCTCTCCCGATACTCGGGG

1381 GGCTTTGTTAACTCTTTAGACACCAATGCTTTGGGTATGTGTTCTGAATGTAATGGGGTG

1441 CGGACGTCATTGGACTGAAATTAATTATTTATTGTGGGTCGGAGGGAGATTGAATAAGTG

1501 GGTGCGGGGCCCCAAATAACAGGTAGGTTCCAGGCAACCTCACTGCAGATTCTTGGAATG

1561 TAGAGGGTTCCCCAGGATAGGAGT
```

6.0 REFERENCES

The references listed below and all references cited herein are each specifically incorporated herein by reference in its entirety to the extent that they supplement, explain, provide a background for, or teach methodology, techniques, and/or compositions employed herein.

U.S. Pat. No. 4,216,209, issued Aug. 5, 1980.
U.S. Pat. No. 5,098,887, issued Mar. 24, 1992.
U.S. Pat. No. 5,145,684, issued Sep. 8, 1992.
U.S. Pat. No. 5,238,921, issued Aug. 24, 1993.
U.S. Pat. No. 5,348,978, issued Sep. 20, 1994.
U.S. Pat. No. 5,399,346, issued Mar. 21, 1995.
U.S. Pat. No. 5,399,363, issued Mar. 21, 1995.
U.S. Pat. No. 5,449,661, issued Sep. 12, 1995.
U.S. Pat. No. 5,466,468, issued Nov. 14, 1995.
U.S. Pat. No. 5,543,158, issued Apr. 6, 1996.
U.S. Pat. No. 5,552,157, issued Sep. 3, 1996.
U.S. Pat. No. 5,552,397, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,641,515, issued Jun. 24, 1997.
U.S. Pat. No. 5,738,868, issued Apr. 14, 1998.
U.S. Pat. No. 5,741,516, issued Apr. 21, 1998.
U.S. Pat. No. 5,795,587, issued Aug. 18, 1998.
Eur. Pat. Appl. Publ. No. EP0273085.
Aarons and Molinoff, "Changes in the density of β-adrenergic receptors in rat lymphocytes, heart and lung after chronic treatment with propranolol," *J. Pharmacol. Exper. Ther.*, 221:439–443, 1982.
Aarons, Nies, Gal, et al., "Elevation of β-adrenergic receptor density in human lymphocytes after propranolol administration," *J. Clin. Invest.*, 65:949–957, 1980.
Ablad, Abrahamsson, Adler, et al., "Cardiac anti-ischemic effect of metoprolol: Role of β-blocker within the ischemic region," *J. Cardiovascular Pharmacol.*, 10(Suppl. 2):S117–S125, 1987.
Abrahamsson, Almgren and Carlsson, "Ischemia-induced noradrenaline release in the isolated rat heart: Influence of perfusion substrate and duration of ischemia," *J. Mol. Cell Cardiol.*, 15:821–830, 1983.

Agarwal and Riftina, "Synthesis and enzymatic properties of deoxyribooligonucleotides containing methyl and phenylphosphonates linkages," *Nucl. Acids Res.*, 6(9):3009–3023, 1979.

Agodoa, "African American study of kidney disease and hypertension (AASK)—clinical trial update," *Ethn. Dis.*, 8(2):249–253, 1998.

Agrawal, Temsamani and Tang, "Pharmacokinetics, biodistribution, and stability of oligo-deoxynucleotide phosphorothioates in mice," *Proc. Nat'l Acad. Sci. USA*, 88:7595–7599, 1991.

Akhtar and Rossi, "Anti-HIV therapy with antisense oligonucleotides and ribozymes: realistic approaches or expensive myths?," *J. Antimicrob. Chemother.*, 38:159–165, 1996.

Allen and Choun, "Large unilamellar liposomes with low uptake into the reticuloendothelial system," *FEBS Lett.*, 223:42–46, 1987.

Allen, "Liposomes: Opportunities in drug delivery," *Drugs*, 54(Suppl. 4):8–14, 1997.

Altschul et al., "Gapped BLAST and PSI-BLAST: a new generation of protein database search programs," *Nucl. Acids Res.*, 25:3389–3402, 1997.

Asseline and Thuong, *Tetrahedron Lett.*, 30(19):2521–2524, 1989.

Baker and Pitha, "Irreversible blockade of beta adrenoceptors and their recovery in the rat heart and lung in vivo," *J. Pharmacol. Exp. Ther.*, 220:247–251, 1982.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Bazil, Krulan and Webb, "Telemetric monitoring of cardiovascular parameters in conscious spontaneously hypertensive rats," *J. Cardiovasc. Pharmacol.*, 22:897–905, 1993.

Benvenisty and Reshef, "Direct introduction of genes into rats and expression of the genes," *Proc. Natl. Acad. Sci. USA*; 83(24): 9551–9555, 1986.

Blumenfeld, J. D., Sealey, J. E., Mann, S. J., Bragat, A., Marion, R., Pecker, M. S., Sotelo, J., August, P., Pickering, T. G. and Laragh, J. H., "Beta-adrenergic receptor blockade as a therapeutic approach for suppressing the renin-angiotensin-aldosterone system in normotensive and hypertensive subjects," *Am. J. Hypertens.*, 12:451–459, 1999.

Böhm, "Alterations of β-adrenoceptor-G-Protein regulated adenylyl cyclase in hearts failure," *Mol. Cell Biochem.*, 147:147–160, 1995.

Bonham et al., "An assessment of the antisense properties of RNase H-competent and steric-blocking oligomers," *Nucleic Acids Res* 1995 April 11;23(7): 1197–203, 1995.

Brown, Deighton, Bals, Sohlmann, Zerkowski, Michel and Brodde, "Spare receptors for beta-adrenoceptor-mediated positive inotropic effects of catecholamines in the human heart," *J. Cardiovasc. Pharmacol.*, 19:222–232, 1992.

Buhler, F. R., "Antihypertensive treatment according to age, plasma renin and race," *Drugs.*, 35:495–503, 1988.

Capecchi, "High efficiency transformation by direct microinjection of DNA into cultured mammalian cells," *Cell*, 22(2):479–488, 1980.

Chamorro, Vila, Ascaso, Elices, Schonewille, Blanc, "Blood pressure and functional recovery in acute ischemic stroke," *Stroke*, 29(9):1850–1853, 1998.

Chandran, Roy, Mishra, "Recent trends in drug delivery systems: liposomal drug delivery system—preparation and characterisation," *Indian J. Exp. Biol.*, 35(8):801–809, 1997.

Chang, Yu, Shinozuka, Zon, Wilson and Strekowska, "Comparative inhibition of ras p21 protein synthesis with phosphorus-modified antisense oligonucleotides," *Anticancer Drug Des.*, 4:221–232, 1989.

Chen and Okayama, "High-efficiency transformation of mammalian cells by plasmid DNA," *Mol. Cell. Biol.*, 7:2745–2752, 1987.

Chen, M., Schnermann, J., Smart, A. M., Brosius, F. C., Killen, P. D., and Briggs, J. P., "Cyclic AMP selectively increases renin mRNA stability in cultured juxtaglomerular granular cells," *J. Biol. Chem.*, 268:24138–24144, 1993.

Chomczynski and Sacchi, "Single step method of RNA isolation by acid guanidinium thio-cyanate-phenol-chloroform extraction," *Anal. Biochem.*, 162:156–159, 1987.

Christensen, Johansen, Marker, Thomsen, "Circulating intracellular adhesion molecule-1 (ICAM-1) as an early and sensitive marker for virus-induced T cell activation," *Clin. Exp. Immunol.*, 102(2):268–273, 1995.

Coffin, "Retroviridae and their replication," In: *Virology*, Fields et al., Eds., New York, Raven Press, pp. 1437–1500, 1990.

Corey, "Peptide nucleic acids: expanding the scope of nucleic acid recognition," *Trends Biotechnol.*, 15(6):224–229, 1997.

Coune, "Liposomes as drug delivery system in the treatment of infectious diseases: potential applications and clinical experience," *Infection*, 16(3):141–147, 1988.

Coupar et al., "A general method for the construction of recombinant vaccinia virus expressing multiple foreign genes," *Gene*, 68:1–10, 1988.

Couvreur et al., "Nanocapsules, a new lysosomotropic carrier," *FEBS Lett.*, 84:323–326, 1977.

Couvreur et al., "Tissue distribution of antitumor drugs associated with polyalkylcyanoacrylate nanoparticles," *J. Pharm. Sci.*, 69(2): 199–202, 1980.

Couvreur, "Polyalkyleyanoacrylates as colloidal drug carriers," *Crit. Rev. Ther. Drug Carrier Syst.*, 5:1–20, 1988.

Curiel, Agarwal, Wagner, Cotten, "Adenovirus enhancement of transferrin-polylysine-mediated gene delivery," *Proc. Natl. Acad Sci. USA*, 88(19):8850–8854, 1991.

Dachs, Dougherty, Stratford and Chaplin, "Targeting gene therapy to cancer: a review," *Oncol. Res.*, 9:313–325, 1997.

Douglas, Davis, Illum, "Nanoparticles in drug delivery," *Crit. Rev. Ther. Drug Carrier Syst.*, 3(3):233–261, 1987.

Dubensky et al., "Direct transfection of viral and plasmid DNA into the liver or spleen of mice," *Proc. Nat. Acad. Sci. USA*, 81:7529–7533, 1984.

Dueholm, Motawia, Pedersen, Nielsen, Lundt, "Synthesis of 3'-alkylthio-2',3'-dideoxy nucleosides with potential anti-HIV activity from 2-deoxy-D-ribose, using a phosphorus pentoxide reagent," *Arch. Pharm. (Weinheim)*, 325(9):597–601, 1992.

Eglitis and Anderson, "Retroviral vectors for introduction of genes into mammalian cells," *Biotechniques* 6(7):608–614, 1988.

Eglitis, Kantoff, Kohn, Karson, Moen, Lothrop, Blaese, Anderson, "Retroviral-mediated gene transfer into hemopoietic cells," *Avd. Exp. Med Biol.*, 241:19–27, 1988.

Faller and Baltimore, "Liposome encapsulation of retrovirus allows efficient super infection of resistant cell lines," *J. Virol.*, 49(1):269–272, 1984.

Fechheimer et al., "Transfection of mammalian cells with plasmid DNA by scrape loading and sonication loading," *Proc. Natl. Acad. Sci. USA*, 84:8463–8467, 1987.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," *FASEB J*, 7(11):1081–1091, 1993.

Fraley et al., "Entrapment of a bacterial plasmid in phospholipid vesicles: Potential for gene transfer," *Proc. Natl. Acad Sci. USA*, 76:3348–3352, 1979.

Fresta and Puglisi, "Application of liposomes as potential cutaneous drug delivery systems. In vitro and in vivo investigation with radioactively labelled vesicles," *J. Drug Target*, 4(2):95–101, 1996.

Friedmann, "Progress toward human gene therapy," *Science*, 244:1275–1281, 1989.

Frielle et al., *Proc. Nat'l Acad. Sci. USA*, 84(22):7920–7924, 1987.

Fromm, Taylor, Walbot, "Expression of genes transferred into monocot and dicot plant cells by electroporation," *Proc. Natl. Acad. Sci. USA*, 82(17):5824–5828, 1985.

Gabizon and Papahadjopoulos, "Liposomes formulations with prolonged circulation time in blood and enhanced uptake by tumors," *Proc. Natl. Acad. Sci. USA*, 85:6949–6953, 1988.

Ghosh and Bachhawat, "Targeting of liposomes to hepatocytes," In: *Liver diseases, targeted diagnosis and therapy using specific receptors and ligands*, Wu and Wu Eds., New York, Marcel Dekker, pp. 87–104, 1991.

Goldstein and Doi, "Prokaryotic promoters in biotechnology," *Biotechnol. Annu. Rev.*, 1:105–128, 1995.

Gomez-Foix et al., "Adenovirus-mediated tranfer of the muscle glycogen phosphorylase gene into hepatocytes confers altered regulation of glycogen metabolism," *J. Biol. Chem.*, 267(35):25129–25134, 1992.

Good and Nielsen, "Progress in developing PNA as a gene-targeted drug," *Antisense Nucl. Acid Drug Dev.*, 7(4):431–437, 1997.

Gopal, "Gene transfer method for transient gene expression, stable transfection, and cotransfection of suspension cell cultures," *Mol. Cell Biol.*, 5:1188–1190, 1985.

Graham and Prevec, "Adenovirus-based expression vectors and recombinant vaccines," *Biotechnology*, 20:363–390, 1992.

Graham and van der Eb, "Transformation of rat cells by DNA of human adenovirus 5," *Virology*, 54(2):536–539, 1973.

Gribskov and Burgess, *Nucl. Acids Res.* 14:6745, 1986, as described by Schwartz and Dayhoff, eds., In: *Atlas of Protein Sequence and Structure*, National Biomedical Research Foundation, pp. 353–358, 1979.

Grunhaus and Horwitz, "Adenovirus as cloning vector," *Sem. in Virol.*, 3:237–252, 1992.

Guderman, Nuenberg and Schultz, "Receptors and G protein as primary components of transmembrane signal transduction," *J. Mol. Med.*, 73:51–63, 1995.

Gyurko, Tran and Phillips, "Time course of inhibition of hypertension by antisense oligonucleotides targeted to ATl angiotensin receptor mRNA in spontaneously hypertensive rats," *Am. J. Hypertens.*, 10(5 Pt. 2):56S–62S, 1997.

Hanvey, Peffer, Bisi, Thomson, Cadilla, Josey, Ricca, Hassman, Bonham, Au, et al., "Antisense and antigene properties of peptide nucleic acids," *Science*, 258(5087):1481–1485, 1992.

Harland and Weintraub, "Translation of mammalian mRNA injected into Xenopus oocytes is specifically inhibited by antisense RNA," *J. Cell Biol.*, 101:1094–1099, 1985.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Heilbrunn, Shah, Valentine, et al., "Increased beta-receptor density and improved hemody-namic response to catecholamine stimulation during chronic metoprolol therapy," *Circulation*, 74(Suppl. II):310, Abstract, 1986.

Henry-Michelland et al., "Attachment of antibiotics to nanoparticles; Preparation, drug-release and antimicrobial activity in vitro," *Int. J. Pharm.*, 35:121–127, 1987.

Hermonat and Muzyczka, "Use of adenoassociated virus as a mammalian DNA cloning vector: Transduction of neomycin resistance into mammalian tissue culture cells," *Proc. Natl. Acad Sci. USA*, 81:6466–6470, 1984.

Herz and Gerard, "Adenovirus-mediated transfer of low density lipoprotein receptor gene acutely accelerates cholesterol clearance in normal mice," *Proc. Natl. Acad Sci. USA* 90:2812–2816, 1993.

Holmer, S., Rinne, B., Eckardt, K. U., Le, H. M., Schricker, K., Kaissling, B., Riegger, G. and Kurtz, A., "Role of renal nerves for the expression of renin in adult rat kidney," *Am. J Physiol.*, 266:F783–F745, 1994.

Holmer, S. R., Kaissling, B., Putnik, K., Pfeifer, M., Kramer, B. K., Riegger, G. A., Kurtz, A., "Beta-adrenergic stimulation of renin expression in vivo," *J. Hypertens.*, 15:1471–1479, 1997.

Hoover et al., Eds., "Remington's Pharmaceutical Sciences," 15th Edition, Mack Publishing Co., Easton, Pa., 1975.

Horwich et al. "Synthesis of hepadenovirus particles that contain replication-defective duck hepatitis B virus genomes in cultured HuH7 cells," *J. Virol.*, 64:642–650, 1990.

Hyrup and Nielsen, "Peptide nucleic acids (PNA): synthesis, properties and potential applications," *Bioorg. Med. Chem.*, 4(1):5–23, 1996.

Ihl-Vahl, Marquetan, Bremerich, et al, "Regulation of β-adrenergic receptors in acute myocardial ischemia: Subtype selective increase of mRNA specific for $\beta_1$-adrenergic receptors," *J. Mol. Cell Cardiol.*, 27:437–452, 1995.

Imaizumi et al., "Liposome-entrapped superoxide dismutase ameliorates infarct volume in focal cerebral ischemia," *Acta. Neurochirurgica Suppl.*, 51:236–238, 1990b.

Imaizumi et al., "Liposome-entrapped superoxide dismutase reduces cerebral infarction in cerebral ischemia in rats," *Stroke*, 21(9):1312–1317, 1990a.

Iversen, P., "In vivo studies with phosphorothioate oligonucleotides:pharmacokinetics prologue," *Anticancer Drug Des.*, 6:531–538, 1991.

Jo, H. Yang, E. K., Lee, W. J., Park, K. Y., Kim, H. J. and Park, J. S., "Gene expression of central and peripheral renin-angiotensin system components upon dietary sodium intake in rats," *Regul. Pept.*, 67:115–121, 1996.

Kaneda, Iwai, Uchida, "Introduction and expression of the human insulin gene in adult rat liver," *J. Biol. Chem.*, 264(21):12126–12129, 1989.

Karliner, Stevens, Honbo, et al., "Effects of acute ischemia in the dog on myocardial blood flow, beta receptors, and adenylate cyclase activity with and without chronic beta blockade," *J. Clin. Invest.*, 83:474–481, 1989.

Kato et al., "Expression of hepatitis β virus surface antigen in adult rat liver," *J. Biol. Chem.*, 266:3361–3364, 1991.

Kaumann, "The beta 1-adrenoceptor antagonist CGP 20712 A unmasks beta 2-adrenoceptors activated by (-)-adrenaline in rat sinoatrial node," *Naunyn Schmiedebergs Arch. Pharmacol.*, 332:406–409, 1986.

Klein, Kornstein, Sanford, Fromm, *Nature*, 327:70–73, 1987.

Klein, Wolf, Wu, Sanford, "High-velocity microprojectiles for delivering nucleic acids into living cells. 1987," *Biotechnology*, 24:384–386, 1992.

Kokita, Hara, Abiko, et al., "Propofol improves functional and metabolic recovery in ischemia reperfused isolated rat hearts," *Anesth. Analg.*, 86:252–258, 1998 .

Lasic, "Novel applications of liposomes," *Trends Biotechnol.*, 16(7):307–321, 1998.

Le Gal La Salle et al., "An adenovirus vector for gene transfer into neurons and glia in the brain," *Science*, 259:988–990, 1993.

Levrero et al., "Significance of anti-HBx antibodies in hepatitis B virus infection," *Hepatology*, 13(1):143–149, 1991.

Li, Tomson, Yang, et al, "Modulation of constitutive nitric oxide synthase, bcl-2 and Fas expression in cultured human coronary endothelial cells exposed to anoxiareoxygenation and angiotensin II: Role of $AT_1$ receptor activation," *Cardiovasc. Res.*, 41:109–115, 1999.

Liu, Mounkes, Liggitt, Brown, Solodin, Heath and Debs, "Factors influencing the efficiency of cationic liposome-mediated intravenous gene delivery," *Nat. Biotechnol.*, 15:167–173, 1997.

Lopez-Berestein et at, "Liposomal amphotericin B for the treatment of systemic fungal infections in patients with cancer: a preliminary study" *J. Infect. Dis.*, 2151:704, 1985a.

Lopez-Berestein et al., "Protective effect of liposomal-amphotericin B against C. albicans infection in mice," *Cancer Drug Delivery*, 2:183, 1985b.

Lu, Vandeplassche, Wouters, et al., "Effects of beta-adrenoceptor antagonists on cardiac function in ischemia-reperfused myocardium of the isolated working rabbit heart," *Eur. J. Pharmacol.*, 184:65–74, 1990.

Lu, Xiao, Clapp, Li, Broxmeyer, "High efficiency retroviral mediated gene transducion into single isolated immature and replatable CD34(3+) hematopoietic stem/progenitor cells from human umbilical cord blood," *J Exp. Med.*, 178(6):2089–2096, 1993.

Machida, Bunzow, Searles, Van, Tester, Neve, Teal, Nipper and Civelli, "Molecular cloning and expression of the rat beta-1-adrenergic receptor," *J. Biol. Chem.*, 265:12960–12965, 1990.

Maisel, Motulsky and Insel, "Externalization of β-adrenergic receptors promoted by myocardial ischemia," *Science*, 230:183–186, 1985.

Maisel, Motulsky, Ziegler, et at, "Ischemia and agonist induced changes in alpha and beta adrenergic receptor traffic in guinea pig hearts," *Am. J Physiol*, 253:H1159–H1166, 1987.

Man in't Veld, A. J. and Schalekamp, M. A., "Haemodynamic consequences of intrinsic sympathomimetic activity in relation to changes in plasma renin activity and noradrenaline during beta-blocker therapy for hypertension," *Postgrad. Med. J.*, 59(suppl 3):140–158, 1983.

Man in't Veld, A. J., van den Meiracker, A. H. and Schalekamp, M. A., "Do beta-blockers really increase peripheral vasculare resistance? Review of the literature and new observations under basal conditions," *Am. J. Hypertens.*, 1:91–96, 1988.

Margalit, "Liposome-mediated drug targeting in topical and regional therapies," *Crit. Rev. Ther. Drug Carrier Syst.*, 12(2–3):233–261, 1995.

Matthews, Molenaar and Summers, "Beta-adrenoceptor subtypes in the atrioventricular conducting system and myocardium of spontaneously hypertensive rats: effects of angiotensin-converting enzyme inhibition by perindopril," *J. Cardiovasc. Pharmacol.*, 23:691–697, 1994.

McLean, Fox, Baluk, Bolton, Haskell, Pearlman, Thurston, Umemoto and McDonald, "Organ-specific endothelial cell uptake of cationic liposome-DNA complexes in mice," *Am. J. Physiol.*, 273:H387–H404, 1997.

Minneman, Hegstrand and Molinoff, "The pharmacological specificity of $β_1$- and $β_2$-adrenergic receptors in rat heart and lung in vitro," *Mol. Pharmacol.*, 27:437–452, 1995.

Mori and Fukatsu, "Anticonvulsant effect of DN-1417 a derivative of thyrotropin-releasing hormone and liposome-entrapped DN-1417 on amygdaloid-kindled rats," *Epilepsia*, 33(6):994–1000, 1992.

Moser, "Why are physicians not prescribing diuretics more frequently in the management of hypertension?," *JAM*, 279(22):1813–1816, 1998.

Mukherjee, Wong, Juja, et al., "Beta adrenergic and muscurinic cholinergic receptors in canine myocardium," *J. Clin. Invest.*, 64:1423–1428, 1979.

Muller et al, "Efficient transfection and expression of heterologous genes in PC12 cells," *Cell, Biol.*, 9(3):221–229, 1990.

Muzyczka and McLaughlin, "Use of adeno-associated virus as a mamalian transduction vector," In: *Current Communications in Molecular Biology: Viral Vectors*, Glzman and Hughes, Eds., Cold Spring Harbor Laboratory Press, Cold Spring Harbor, N.Y., pp. 39–44, 1988.

Needleman and Wunsch, *J. Mol. Biol.*, 48:443, 1970, as revised by Smith and Waterman, *Adv. Appl. Math.* 2:482, 1981.

Neely and Rovetto, "Techniques for perfusing isolated rat hearts," *Methods Enzymol.*, 39:43–60, 1975.

Neve and Molinoff, "Turnover of beta 1- and beta 2-adrenergic receptors after down-regulation or irreversible blockade," *Mol. Pharmacol.*, 30:104–111, 1986.

Nicholls, Richards, Agarwal, "The importance of the renin-angiotensin system in cardiovascular disease," *J. Hum. Hypertens*, 12(5):295–299, 1998.

Nicolau and Gersonde, "Incorporation of inositol hexaphosphate into intact red blood cells, I. fusion of effector-containing lipid vesicles with erythrocytes," *Naturwissenschaften* (Germany), 66(11):563–566, 1979.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Nielsen et al., "DNA analogues with nonphosphodiester backbones," *Annu. Rev. Biophys. Biomol. Struct.*, 24:167–183, 1995.

Nielsen, DiGiovanni, Christensen, Knepper, Harris, "Cellular and subcellular immunolocalization of vasopressin-regulated water channel in rat kidney," *Proc. Natl. Acad. Sci. USA*, 90(24): 11663–11667, 1993.

Norton, Waggenspack, Varnum, Corey, "Targeting peptide nucleic acid-protein conjugates to structural features within duplex DNA," *Bioorg. Med. Chem.*, 3(4):437–445, 1995.

Ohkawa, Ohishi and Yahi, "Assay for lipid peroxides in animal tissues by thiobarbituric acid reaction," *Anal. Biochem.*, 95:351–358, 1979.

Ohyanahi, Matsumori and Iwasaki, "Beta-adrenergic receptors in ischemic and nonischemic canine myocardium: Relation to ventricular fibrillation and effects of pretreatment with propranolol and hexamethonium," *J. Cardiovasc. Pharmacol.*, 11:107–114, 1988.

Ozden, Aybek, Saydam, et al., "Cytoprotective effect of trimentazidine on 75 min renal ischemia-reperfusion injury in rats," *Eur. Surg. Res.*, 30:227–234, 1998.

Pardridge, "CNS drug design based on principles of blood-brain barrier transport," *J. Neurochem.*, 70:1781–1792, 1998.

Perales et al., *Proc. Natl. Acad. Sci. USA*, 91:4086–4090, 1994.

Persad, Panagia and Dhalla, "Role of $H_2O_2$ in changing β-adrenoceptor and adenylyl cyclase in ischemia-reperfused hearts," *Mol. and Cel. Biochem.*, 186:99–106, 1998.

Phillips et al., "Antisense inhibition and adeno-associated viral vector delivery for reducing hypertension," *Hypertension*, 29(2):177–187, 1997.

Phillips, Ambuhl and Gyurko, "Antisense oligonucleotides for in vivo studies of angiotensin receptors," *Adv. Exp. Med. Biol.*, 396:79–92, 1996.

Phillips and Kimura, "Brain angiotensin in the developing spontaneously hypertensive rat," *J. Hypertens.*, 6:607–612, 1988.

Phillips, Wielbo, Gyurko, "Anitsense inhibiiton of hypertension: a new strategy for renin-angiotensin candidate genes," *Kidney International*, 46:1554–1556, 1994.

Pikul et al., "In vitro killing of melanoma by liposome-delivered intracellular irradiation", *Arch. Surg.*, 122(12):1417–1420, 1987.

Pinto-Alphandary, Balland, Couvreur, "A new method to isolate polyalkylcyanoacrylate nanoparticle preparations," *J. Drug Target*, 3(2):167–169, 1995.

Potter et al., "Enhancer-dependent expression of human κ immunoglobulin genes introduced into mouse pre-B lymphocytes by electroporation," *Proc. Natl. Acad Sci. USA*, 81:7161–7165, 1984.

Quintanar-Guerrero, Allemann, Doelker, Fessi, "Preparation and characterization of nanocapsules from preformed polymers by a new process based on emulsification-diffusion techinque," *Phamr. Res.*, 15(7):1056–1062, 1998.

Ragot et al., "Efficient adenovirus-mediated transfer of a human minidystrophin gene to skeletal muscle of mdx mice," *Nature*, 361:647–650, 1993.

Renneisen et al., "Inhibition of expression of human immunodeficiency virus-1 in vitro by antibody-targeted liposomes containing antisense RNA to the env region," *J. Biol. Chem.*, 265(27):16337–16342, 1990.

Rich et al., "Development and analysis of recombinant adenoviruses for gene therapy of cystic fibrosis," *Hum. Gene Ther.*, 4:461–476, 1993.

Richardt, Blessing and Schomig, "Cardiac noradrenaline release accelerates adenosine formation in the ischemia rat heart: Role of neuronal noradrenaline carrier and adrenergic receptors," *J. Mol. Cell Cardiol.*, 26:1321–1328, 1994.

Ridgeway, "Mammalian expression vectors," In: *Vectors: A survey of molecular cloning vectors and their uses*, Rodriguez RL, Denhardt DT, ed., Stoneham: Butterworth, pp. 467–492, 1988.

Rippe et al, "DNA-mediated gene transfer into adult rat hepatocytes in primary culture," *Mol. Cell Biol.*, 10:689–695, 1990.

Rodefeld, Beau, Schuessler, Boineau and Saffitz, "Beta-adrenergic and muscarinic cholinergic receptor densities in the human sinoatrial node: identification of a high beta 2-adrenergic receptor density," *J. Cardiovasc. Electrophysiol.*, 7:1039–1049, 1996.

Rodgers, "Combination drug therapy in hypertension: a rational approach for the pharmacist," *J. Am. Pharm. Assoc.*, 38(4):469–479, 1998.

Rona, "Catecholamine cardiotoxicity," *J. Mol. Cell Cardiol.*, 17:291–306, 1985.

Rosenfeld et al., "Adenovirus-mediated transfer of a recombinant al-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Rosenthal, "Drug therapy of renovascular hypertension," *Drugs*, 45(6):895–909, 1993.

Schackert, Fran, Nayar and Fidler, "Arrest and retention of multilamellar liposomes in the brain of normal mice or mice bearing experimental brain metastases," *Sel. Cancer Ther.*, 5:73–79, 1989.

Schulz, Rose, Skyschally, et al., "Bradycardiac agent UL FS 49 attenuates ischemia regional myocardial dysfunction and reduces infarct size in swine: Comparison with the β-blocker atenolol," *J. Cardiovascular Pharmacol.*, 25:216–228, 1995.

Schwab, Chavany, Duroux, Goubin, Lebeau, Helene, Saison-Behmoaras, "Antisense oligonucleotides adsorbed to polyalkylcyanoacrylate nanoparticles specifically inhibit mutated Ha-ras-mediated cell proliferation and tumorigenicity in nude mice," *Proc. Natl. Acad. Sci. USA*, 91(22):10460–10464, 1994.

Sculier et al., "Pilot study of amphotericin B entrapped in sonicated liposomes in cancer patients with fungal infections," *J. Cancer Clin. Oncol.*, 24(3):527–538, 1988.

Sproat and Lopez, "Around the beta-blockers, one more time," *DICP*, 25:962–971, 1991.

Sproat, T. T. and Lopez, L. M., "Around the beta-blockers, one more time," *DICP*, 25:962–971, 1991.

Stallworth and Waldron, "Cortical blindness as a complication of acute glomerulonephritis," *J.S.C. Med Assoc.*, 93(3):99–101, 1997.

Stein et al., *Gene*, 72:333≤341, 1988.

Strassere, Marquetant and Kubler, "Independent sensitization of β-adrenoceptors and adenylate cyclase in acute myocardial ischemia," *Br. J. Clin. Pharmacol.*, 30:27S–35S, 1990.

Stratford-Perricaudet and Perricaudet, "Gene transfer into animals: the promise of adenovirus," p. 51–61, In: *Human Gene Transfer*, Cohen-Haguenauer and Boiron, Eds., Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Summers, R. J., Stephenson, J. A., and Kuhar, M. J., "Localization of beta adrenoceptor subtypes in rat kidney by light microscopic autoradiography," *J. Pharmacol. Exp. Ther.*, 232:561–569, 1985.

Suzuki, Shin, Fjuikura, Matsuzaki, Takata, "Direct gene transfer into rat liver cells by in vivo electroporation," *FEBS Lett.*, 425(3):436–440, 1998.

Takakura, "Drug delivery systems in gene therapy," *Nippon Rinsho*, 56(3):691–695, 1998.

Tang and Hughes, "Introduction of a disulfide bond into a cationic lipid enhances transgene expression of plasmid DNA," *Biochem. Biophys. Res. Commun.*, 242:141–145, 1998.

Templeton, N. S., Lasic, D. D., Frederik, P. M., Strey, H. H., Roberts, D. D. and Pavlakis, G. N., "Improved DNA: liposome complexes for increased systemic delivery and gene expression," *Nat. Biotechnol.*, 15:647–652, 1997.

Thandroyen, Muntz, Rosenbaum, et al., "Influence of hypoxia on beta adrenergic receptor density and adenylate cyclase activity in isolated neonatal ventricular myocytes," *Circulation*, 74:324, 1986.

Truong-Le, August, Leong, "Controlled gene delivery by DNA-gelatin nanopspheres," *Hum. Gene Ther.*, 9(12):1709–1717, 1998.

Tur-Kaspa et al., "Use of electroporation to introduce biologically active foreign genes into primary rat hepatocytes," *Mol. Cell Biol.*, 6:716–718, 1986.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.*, 11(l):23–34, 1998.

Wagner, Matteucci, Lewis, Gutierrez, Moulds, Froehler, "Antisense gene inhibition by oligonucleotides containing C-5 propyne pyrimidines," *Science*, 260(5113):1510–1513, 1993.

Wagner, Zatloukal, Cotten, Kirlappos, Mechtler, Curiel, Bimstiel, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.

Waldenstrom, Hjalmarson and Thornell, "A possible role of noradrenaline in the development of myocardial infarction: an experimental study in the isolated rat heart," *Am. Heart J.*, 95:43–51, 1978.

Winter, Inkpen, Dickinson, Rudd and Sever, "De novo cardiac beta adrenoceptor synthesis in adult rats under normoxic and hypoxic conditions," *Cardiovasc. Res.*, 22:159–162, 1988.

Wong and Neumann, "Electric field mediated gene transfer," *Biochim. Biophys. Res. Commun.*, 107(2):584–587, 1982.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Yang and Huang, "Time-dependent maturation of cationic liposome-DNA complex for serum resistance," *Gene Ther.*, 5:380–387, 1998.

Yang et al., "In vivo and in vitro gene transfer to mammalian somatic cells by particle bombardment," *Proc. Natl. Acad Sci. USA*, 87:9568–9572, 1990.

Yang, Chen, Saldeen, et al., "Reperfusion injury in the endotoxin-treated rat-heart: reevaluation of the role of nitric oxide," *Br. J. Pharmacol.*, 120:305–311, 1997.

Yang, Phillips, Zhang, et al., "Critical role of $AT_1$ receptor expression after ischemia/reperfusion in isolated rat hearts. Beneficial effect of antisense oligodeoxynucleotides directed at $AT_1$ receptor mRNA," *Circ. Res.*, 83:552–559, 1998.

Yang, Virmani, Nichols, et al., "Platelets protect against myocardial dysfunction and injury induced by ischemia and reperfusion in isolated rat hearts," *Circ. Res.*, 72:1181–1190, 1993.

Yang and Huang, "Overcoming the inhibitory effect of serum on lipofection by increasing the charge ratio of cationic liposome to DNA," *Gene Ther.*, 4:950–960, 1997.

Yla, "Vascular gene transfer," *Curr. Opin. Lipidol.*, 8:72–76, 1997.

Yusof, Peto, Lewis, et al., "Beta blockade during and after myocardial infarction: An overview of the randomized trials," *Prog. Cardiovasc. Dis.*, 27:335–371, 1985.

Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release*, 50(1–3):31–40, 1998.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zhang, Bui and Phillips, "Antisense inhibition of $β_1$-adrenoceptor mRNA in a single dose produces a profound and prolonged reduction in high blood pressure in spontaneously hypertensive rats," *Circulation* 101(6):682–88, 200, 1999.

Zhang, Diasio, Lu, Liu, Jiang, Galbraith and Agrawal, "Pharnacokinetics and tissue distribution in rats of an oligodeoxynucleotide phosphorothioate (GEM 91) developed as a therapeutic agent for human immunodeficiency virus type-1," *Biochem. Pharmacol.*, 49:929–939, 1995.

zur Muhlen, Schwarz, Mehnert, "Solid lipid nanoparticles (SLN) for controlled drug delivery—drug release and release mechanism," *Eur. J Pharm. Biopharm.*, 45(2):149–155, 1998.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. ore specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated antisense oligonucleotide at least 9 to about 35 nucleotides in length, wherein said oligonucleotide specifically binds to a portion of an mRNA expressed from a gene encoding a mammalian $\beta_1$-adrenoceptor polypeptide, and further wherein binding of said oligonucleotide to said mRNA is effective in altering the translation of said mRNA into said $\beta_1$-adrenoceptor polypeptide in a host cell expressing said mRNA.

2. The oligonucleotide of claim 1, comprising deoxyribonucleic acid, ribonucleic acid, or peptide-nucleic acid.

3. The oligonucleotide of claim 2, comprising a derivatized deoxyribonucleic acid, ribonucleic acid, or peptide-nucleic acid.

4. The oligonucleotide of claim 3, comprising a phosphorothioated deoxyribonucleic acid, ribonucleic acid, or peptide-nucleic acid derivative.

5. The oligonucleotide of claim 1, comprising a sequence of at least nine contiguous bases from any one of SEQ ID NO:4 through SEQ ID NO:186.

6. The oligonucleotide of claim 5, comprising a sequence of at least ten contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:93 through SEQ ID NO:186.

7. The oligonucleotide of claim 6, comprising a sequence of at least thirteen contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:93 through SEQ ID NO:186.

8. The oligonucleotide of claim 7, comprising a sequence of at least sixteen contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:111 through SEQ ID NO:186.

9. The oligonucleotide of claim 8, comprising a sequence of at least eighteen contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:127 through SEQ ID NO:186.

10. The oligonucleotide of claim 9, comprising a sequence of at least twenty contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:147 through SEQ ID NO:186.

11. The oligonucleotide of claim 10, comprising a sequence of at least twenty-two contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or any one of SEQ ID NO:166 through SEQ ID NO:186.

12. The oligonucleotide of claim 11, comprising a sequence of at least twenty-four contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:181, SEQ ID NO:182, SEQ ID NO:183, SEQ ID NO:184, SEQ ID NO:185 or SEQ ID NO:186.

13. The oligonucleotide of claim 12, comprising a sequence of at least twenty-seven contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28.

14. The oligonucleotide of claim 13, comprising a sequence of at least thirty contiguous bases from any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28.

15. The oligonucleotide of claim 14, comprising the sequence of any one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

16. The oligonucleotide of claim 14, comprising the sequence of any one of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

17. The oligonucleotide of claim 14, comprising the sequence of any one of SEQ ID NO:24, SEQ ID NO:25, SEQ ID NO:26, SEQ ID NO:27, or SEQ ID NO:28.

18. The oligonucleotide of claim 1, wherein said oligonucleotide is at least 90% complementary to the portion of the mRNA sequence to which it specifically binds.

19. The oligonucleotide of claim 18, wherein said oligonucleotide is at least 95% complementary to the portion of the mRNA sequence to which it specifically binds.

20. The oligonucleotide of claim 19, wherein said oligonucleotide is at least 98% complementary to the portion of the mRNA sequence to which it specifically binds.

21. The oligonucleotide of claim 1, wherein said oligonucleotide has no more than one nucleotide for every nine contiguous nucleotides that is non-complementary to the portion of the mRNA sequence to which it specifically binds.

22. The oligonucleotide of claim 21, wherein said oligonucleotide has no more than one nucleotide for every ten contiguous nucleotides that is non-complementary to the portion of the mRNA sequence to which it specifically binds.

23. The oligonucleotide of claim 22, wherein said oligonucleotide has no more than one nucleotide for every eleven contiguous nucleotides that is non-complementary to the portion of the mRNA sequence to which it specifically binds.

24. The oligonucleotide of claim 23, wherein said oligonucleotide has no more than one nucleotide for every twelve contiguous nucleotides that is non-complementary to the portion of the mRNA sequence to which it specifically binds.

25. The oligonucleotide of claim 1, wherein said host cell is a mammalian host cell.

26. The oligonucleotide of claim 25, wherein said host cell is a human cell.

27. The oligonucleotide of claim 1, wherein said host cell is comprised within a human.

28. The oligonucleotide of claim 1, wherein said oligonucleotide is at least 9 to about 30 bases in length.

29. The oligonucleotide of claim 28, wherein said oligonucleotide is at least 9 to about 25 bases in length.

30. The oligonucleotide of claim 29, wherein said oligonucleotide is at least 9 to about 20 bases in length.

31. The oligonucleotide of claim 30, wherein said oligonucleotide is at least 9 to about 15 bases in length.

32. The oligonucleotide of claim 31, wherein said oligonucleotide is at least 9 to about 12 bases in length.

33. The oligonucleotide of claim 1, wherein said oligonucleotide comprises the sequence of any one of SEQ ID NO:29 to SEQ ID NO:186.

34. The oligonucleotide of claim 33, wherein said oligonucleotide comprises the sequence of any one of SEQ ID NO:93 to SEQ ID NO:186.

35. The oligonucleotide of claim 34, wherein said oligonucleotide comprises the sequence of any one of SEQ ID NO:93 to SEQ ID NO:166.

36. The oligonucleotide of claim 35, wherein said oligonucleotide comprises the sequence of any one of SEQ ID NO:93 to SEQ ID NO:146.

37. The oligonucleotide of claim 36, wherein said oligonucleotide comprises the sequence of any one of SEQ ID NO:93 to SEQ ID NO:126.

38. The oligonucleotide of claim 36, wherein said oligonucleotide comprises the sequence of any one of SEQ ID NO:96 to SEQ ID NO:112.

39. A recombinant vector comprising a nucleic acid which expresses (a) the isolated oligonucleotide of claim 1, or (b) an isolated antisense polynucleotide that consists essentially of a sequence that is complementary to the sequence of from about position 87 to position 1520 of SEQ ID NO:187.

40. The recombinant vector of claim 39, wherein said vector is a viral, retroviral, adenoviral, or adenoassociated viral vector.

41. A host cell comprising the oligonucleotide of claim 1 or the recombinant vector of claim 39.

42. A composition comprising the oligonucleotide of claim 1.

43. A kit comprising the oligonucleotide of claim 1 or the composition of claim 42.

44. The composition of claim 42, further comprising a pharmaceutical excipient.

45. The composition of claim 44, further comprising a liposome, a lipid particle, a lipid vesicle, a nanoparticle, a microparticle, a nanocapsule, a nanosphere, or a sphingosome.

46. The composition of claim 42, further comprising at least a second oligonucleotide of at least 9 to about 35 nucleotides in length, wherein said second oligonucleotide also specifically binds to a portion of an mRNA that encodes a $\beta_1$-adrenoceptor polypeptide, and further wherein the nucleotide sequence of said second oligonucleotide is different from the nucleotide sequence of the first oligonucleotide in said composition.

47. The composition of claim 46, wherein said second oligonucleotide is any one of SEQ ID NO:4 through SEQ ID NO:186.

48. The composition of claim 42, further comprising at least a first anti-hypertensive agent.

49. The composition of claim 48, wherein said anti-hypertensive agent is selected from the group consisting of captopril, enalapril, ramipril, cilazapril, fosinopril, and lisinopril.

50. The composition of claim 42, further comprising at least a second antisense oligonucleotide specific for a mammalian transcription factor mRNA, a renin-specific mRNA, an angiotensin-specific mRNA, an angiotensinogen-specific mRNA, an AT-1 receptor-specific mRNA, or an angiotensin converting enzyme.

51. The composition of claim 50, wherein said second antisense oligonucleotide is specific for a mammalian angiotensin converting enzyme mRNA.

52. A method for reducing the level of $\beta_1$-adrenoceptor polypeptide in a mammalian host cell, said method comprising providing to said cell, an amount of the oligonucleotide of claim 1, or the composition of claim 42, and for a time effective to reduce the level of said polypeptide in said host cell.

53. A method for reducing the level of transcription of a $\beta_1$-adrenoceptor polypeptide-specific mRNA in a mammalian host cell, said method comprising providing to said cell, an amount of the oligonucleotide of claim 1, or the composition of claim 42, and for a time effective to reduce the level of transcription of said mRNA in said host cell.

54. The method of claim 52 or 53, wherein said host cell is comprised within a mammal.

55. The method of claim 54, wherein said mammal is a human.

56. A method for decreasing hypertension in a mammal, said method comprising administering to said mammal, an amount of the oligonucleotide of claim 1 or the composition of claim 42, and for a time effective to decrease hypertension in said mammal.

57. A method for reducing the symptoms of a disease or disorder associated with an elevated $\beta_1$-adrenoceptor polypeptide level in a mammal, said method comprising administering to said mammal a therapeutically effective amount of the oligonucleotide of claim 1, SEQ ID NO:1, SEQ ID NO:2, or SEQ ID NO:3, or the composition of claim 42, for a time sufficient to decrease the level of said polypeptide in said mammal, thereby reducing the symptoms of said disease or disorder in said mammal.

58. A method for treating myocardial ischemia or cardiac hypertrophy in an affected mammal, said method comprising administering to said mammal, a therapeutically effective amount of the oligonucleotide of claim 1, SEQ ID NO:1, SEQ ID NO:2, or SEQ ID NO:3, or the composition of claim 42, for a time sufficient to treat said ischemia or said hypertrophy in said mammal.

59. A method for reducing the level of $\beta_1$-adrenoceptor polypeptide in a mammalian host cell, said method comprising expressing in said host cell, a selected genetic construct that comprises a full-length, or substantially full-length $\beta_1$-adrenoceptor antisense polynucleotide operably linked to a promoter capable of expressing said polynucleotide in said cell.

60. The recombinant vector of claim 39, comprising the isolated oligonucleotide of claim 1.

61. The recombinant vector of claim 39, comprising an isolated antisense polynucleotide that consists essentially of a sequence that is complementary to the sequence of from about position 87 to position 1520 of SEQ ID NO:187.

62. The recombinant vector of claim 39, comprising an isolated antisense polynucleotide that consists of a sequence that is complementary to the sequence of from about position 87 to position 1520 of SEQ ID NO:187.

63. The method of claim 52, wherein said method comprises providing to said cell, an amount of the composition of claim 42, and for a time effective to reduce the level of said polypeptide in said host cell.

64. The method of claim 53, wherein said method comprises providing to said cell, an amount of the composition of claim 42, and for a time effective to reduce said level of transcription of said mRNA in said host cell.

65. The method of claim 55, wherein said human has, is suspected of having, or is at risk for developing, hypertension, myocardial ischemia or cardiac hypertrophy.

* * * * *